United States Patent
Flores et al.

(10) Patent No.: US 10,195,229 B2
(45) Date of Patent: Feb. 5, 2019

(54) GENERATION OF HUMAN INDUCED PLURIPOTENT STEM CELLS USING NUCLEIC ACID SEQUENCES THAT INHIBIT Δ-NP63 AND DGCR8

(71) Applicants: Elsa R. Flores, Lutz, FL (US); Deepavali Chakravarti, Pearland, TX (US)

(72) Inventors: Elsa R. Flores, Lutz, FL (US); Deepavali Chakravarti, Pearland, TX (US)

(73) Assignees: Elsa R. Flores, Lutz, FL (US); Deepavali Chakravarti, Pearland, TX (US)

( * ) Notice: Subject to any disclaimer, the term of this patent is extended or adjusted under 35 U.S.C. 154(b) by 0 days.

(21) Appl. No.: 14/394,882

(22) PCT Filed: Apr. 18, 2013

(86) PCT No.: PCT/US2013/037186
§ 371 (c)(1),
(2) Date: Oct. 16, 2014

(87) PCT Pub. No.: WO2013/158890
PCT Pub. Date: Oct. 24, 2013

(65) Prior Publication Data
US 2015/0157662 A1 Jun. 11, 2015

Related U.S. Application Data

(60) Provisional application No. 61/635,491, filed on Apr. 19, 2012.

(51) Int. Cl.
| | |
|---|---|
| *A61K 35/12* | (2015.01) |
| *C12N 5/074* | (2010.01) |
| *C12N 15/113* | (2010.01) |

(52) U.S. Cl.
CPC ............ *A61K 35/12* (2013.01); *C12N 5/0696* (2013.01); *C12N 15/113* (2013.01); *C12N 2310/14* (2013.01); *C12N 2320/30* (2013.01); *C12N 2501/40* (2013.01); *C12N 2501/998* (2013.01); *C12N 2506/094* (2013.01); *C12N 2510/00* (2013.01)

(58) Field of Classification Search
USPC .......................... 435/325, 455; 800/8, 18, 21
See application file for complete search history.

(56) References Cited

U.S. PATENT DOCUMENTS

| | | |
|---|---|---|
| 7,294,459 B1 | 11/2007 | Yang et al. |
| 9,080,172 B2 | 7/2015 | Schwob et al. |
| 2011/0129928 A1 | 6/2011 | Park et al. |

FOREIGN PATENT DOCUMENTS

| | | |
|---|---|---|
| EP | 1970446 | * 12/2006 |
| WO | WO 2011-050470 | 5/2011 |

OTHER PUBLICATIONS

Takahashi (Cell, 2006, vol. 126:663-676).*
Yu (Science, 2007, vol. 318, p. 1917-1920).*
Park (Nature, Jan. 2008, vol. 451, p. 141-146).*
Aoi (Science, Aug. 1, 2008, vol. 321, No. 5889, p. 699-702, available online Feb. 14, 2008).*
Nakagawa (Nat Biotechnol, Jan. 2008, vol. 26: 101-106).*
Feng (Cell Stem Cell, Apr. 3, 2009, vol. 4, p. 301-312).*
Gonzalez (PNAS, Jun. 2, 2009, vol. 106, No. 22, p. 8918-8922).*
Yamanaka (Nature, Jul. 2, 2009, vol. 460, No. 7251, p. 12759-12764).*
Hotta (J. Cell. Biochem., Sep. 2008, vol. 105, p. 940-948).*
Papapetrou (PNAS, Aug. 4, 2009, vol. 106, No. 31, p. 12759-12764).*
Ramirez (Unexpected failure rates for modular assembly of engineered zinc fingers. Nature Methods, 2008, 5(5): 374-375).*
Christian (Genetics, available online Jul. 26, 2008, vol. 186, p. 757-761).*
Ellis (Cancer Therapy Res., 2008, vol. 14, No. 14, p. 4500-4510).*
Napoli (Cancer Cell, Jun. 13, 2016, vol. 29, p. 874-888.*
Ramano (Development, published online Jan. 24, 2012, vol. 139, p. 772-782).*
Leonard (Cell Differentiation, published online Jun. 3, 2011, vol. 18, p. 1924-1933.*
Cho (Cell Cycle, Jun. 15, 2010, vol. 9, No. 12, p. 2434-2441).*
Lang (Cell, 2004, vol. 119, p. 861-872).*
Cho (UT GSBS Dissertations and Theses (Open Access), Paper 128, May 2011).*
Sullivan (Jan. 2010, vol. 51, No. 1, p. 329-335).*
Murry (Cell, Feb. 22, 2008, vol. 132, p. 661-680).*
Chakravarti (PNAS, Jan. 21, 2014, E572-E581).*
Robintson (Nature, May 2013, vol. 481, No. 7381, p. 295-305).*
Anokye-Danso et al., "Highly efficient miRNA-mediated reprogramming of mouse and human somatic cells to pluripotency," *Cell Stem Cell*, 8:376-388, 2011.
Boominathan, "The tumor suppressors p53, p63, and p73 are regulators of microRNA processing complex," *PLoS One*, 5(5):e10615, 2010.
Chakravarti et al., "Induced multipotency in adult keratinocytes through down-regulation of ΔNp63 or DGCR8," *Proc Natl Acad Sci USA*, 111(5):E572-581, 2014.
Cho et al., "ΔNp63 transcriptionally regulates brachyury, a gene with diverse roles in limb development, tumorigenesis and metastasis," *Cell Cycle*, 9(12):2434-2441, 2010.
Cho, "ΔNp63 regulates a complex network of target genes in limb and epidermal development," *UT GSBS Dissertations and Theses (Open Access)*, Paper 128, 2011.

(Continued)

*Primary Examiner* — Michael C Wilson
(74) *Attorney, Agent, or Firm* — Parker Highlander PLLC

(57) ABSTRACT

The present invention generally concerns particular methods and compositions for generation of induced pluripotent stem cells. In particular aspects, induced pluripotent stem cells are generated from adult somatic cells following downregulation of a particular gene of interest. In some embodiments, induced pluripotent stem cells are generated from keratinocytes upon downregulation of ΔNp63 or DGCR8.

11 Claims, 39 Drawing Sheets
Specification includes a Sequence Listing.

(56) References Cited

OTHER PUBLICATIONS

Flores, "Unraveling the complexities of p63 in cancer and stem cells," *Proceedings of the AACR Special Conference on Noncoding RNAs and Cancer*, Abstract IA7, 2012.
Hong et al., "Suppression of induced pluripotent stem cell generation by the p53-p21 pathway," *Nature*, 460:1132-1135, 2009.
Kawamura et al., "Linking the p53 tumour suppressor pathway to somatic cell reprogramming," *Nature*, 460:1140-1144, 2009.
Koster et al., "p63 induces key target genes required for epidermal morphogenesis," *Proc Natl Acad Sci U S A*, 104:3255-3260, 2007.
Li et al., "Small RNA-mediated regulation of iPS cell generation," *EMBO J*, 30:823-834, 2011.
Lin et al., "Mir-302 reprograms human skin cancer cells into a pluripotent ES-cell-like state," *RNA*, 14:2115-2124, 2008.
Lin et al., "p63 and p73 transcriptionally regulate genes involved in DNA repair," *PLoS Genet*, 5:e1000680, 2009.
McDade et al., "p63 maintains keratinocyte proliferative capacity through regulation of Skp2-p130 levels," *Journal of Cell Science*, 124:1635-1643, 2011.
Oh et al., "ΔNp63α protein triggers epithelial-mesenchymal transition and confers stem cell properties in normal human keratinocytes," *The Journal of Biologcial Chemistry*, 286(44):38757-38767, 2011.
PCT International Search Report and Written Opinion issued in International Application No. PCT/US2013/037186, dated Jul. 29, 2013.

Romano et al., "ΔNp63 knockout mice reveal its indispensable role as a master regulator of epithelial development and differentiation," *Development*, 139:772-782, 2012
Senoo et al., "p63 is essential for the proliferative potential of stem cells in stratified epithelia," *Cell*, 129:523-536, 2007.
Su et al., "TAp63 prevents premature aging by promoting adult stem cell maintenance," *Cell Stem Cell*, 5:64-75, 2009.
Takahashi and Yamanaka, "Induction of pluripotent stem cells from mouse embryonic and adult fibroblast cultures by defined factors," *Cell*, 126:663-676, 2006.
Tay et al., "MicroRNAs to Nanog, Oct4 and Sox2 coding regions modulate embryonic stem cell differentiation," *Nature*, 455:1124-1128, 2008.
Truong et al., "p63 regulates proliferation and differentiation of developmentally mature keratinocytes," *Genes & Development*, 20:3185-3197, 2006.
Wang et al., "DGCR8 is essential for microRNA biogenesis and silencing of embryonic stem cell self-renewal," *Nature Genetics*, 39(3):380-385, 2007.
Yi et al., "DGCR8-dependent microRNA biogenesis is essential for skin development," *PNAS*, 106(2):498-502, 2009.
Yi et al., "Morphogenesis in skin is governed by discrete sets of differentially expressed microRNAs," *Nature Genetics*, 38(3):356-362, 2006.

* cited by examiner

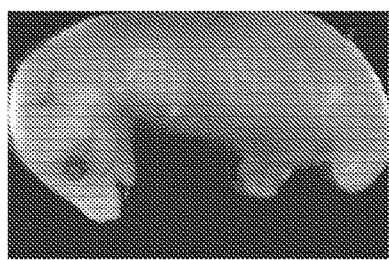 FIG.1G WT
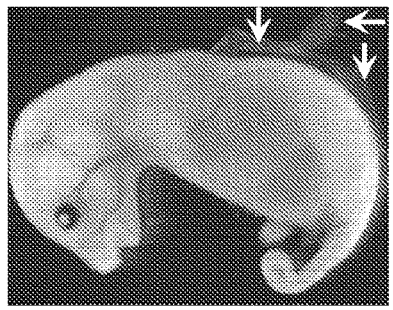 FIG.1H ΔNp63+/-
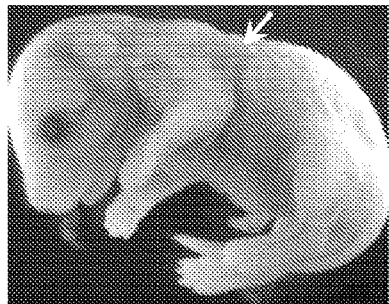 FIG.1I ΔNp63-/-
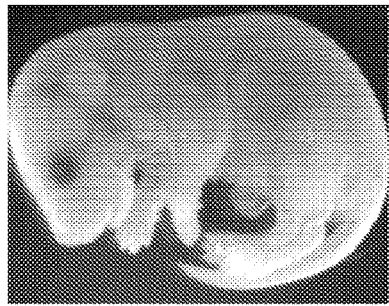 FIG.1J p63-/-
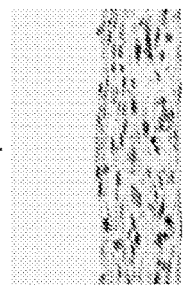 FIG.1K WT H&E
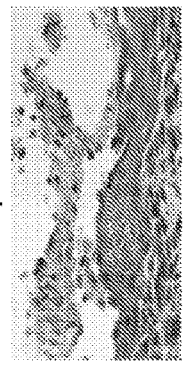 FIG.1L ΔNp63+/- H&E
 FIG.1M ΔNp63-/- H&E
 FIG.1N p63-/- H&E

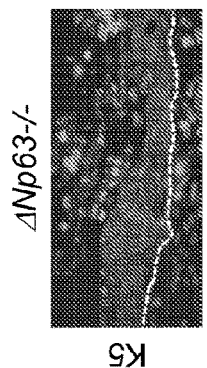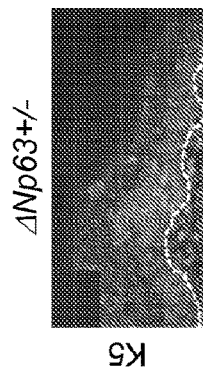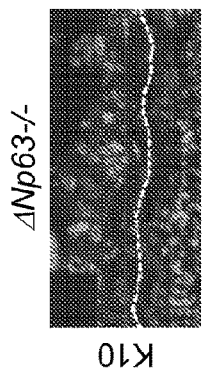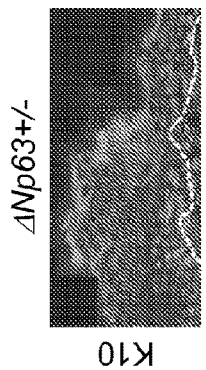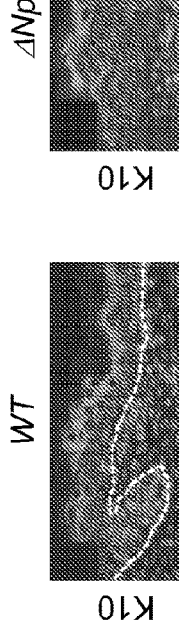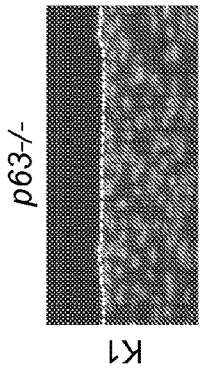

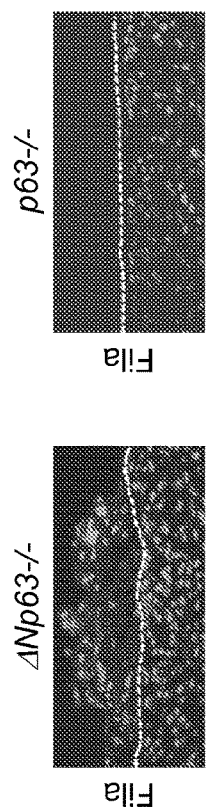  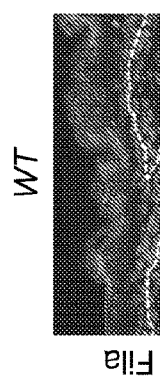
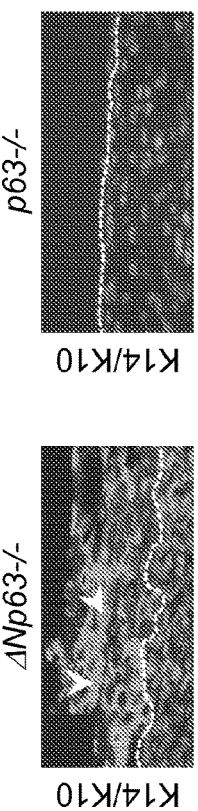 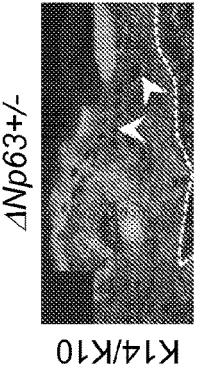 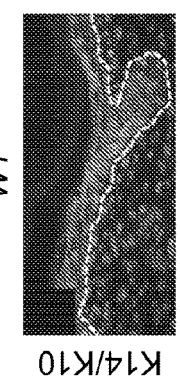
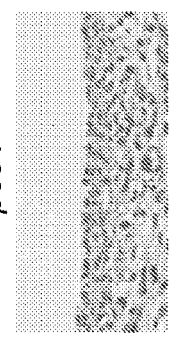 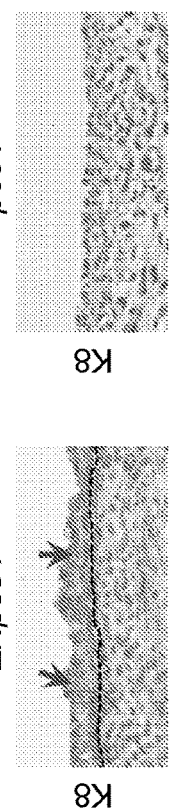 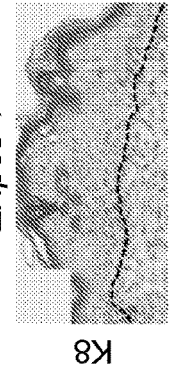 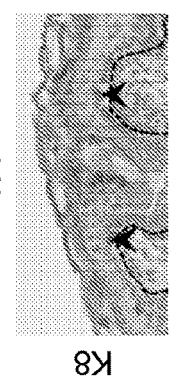

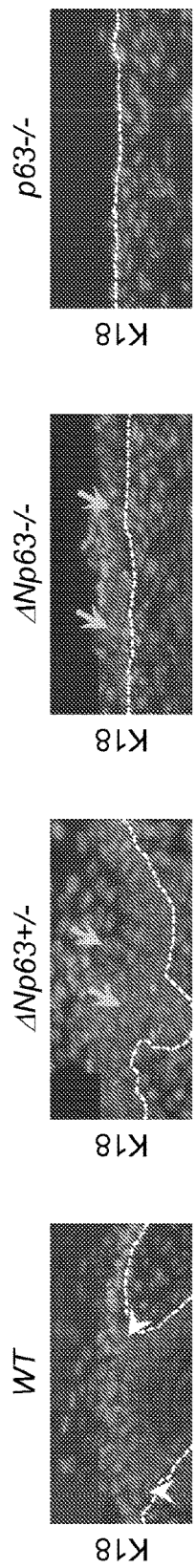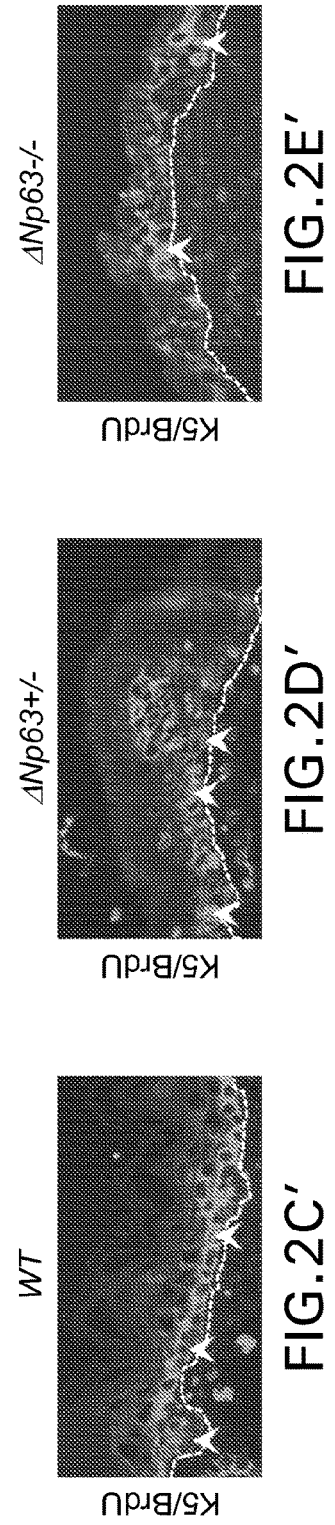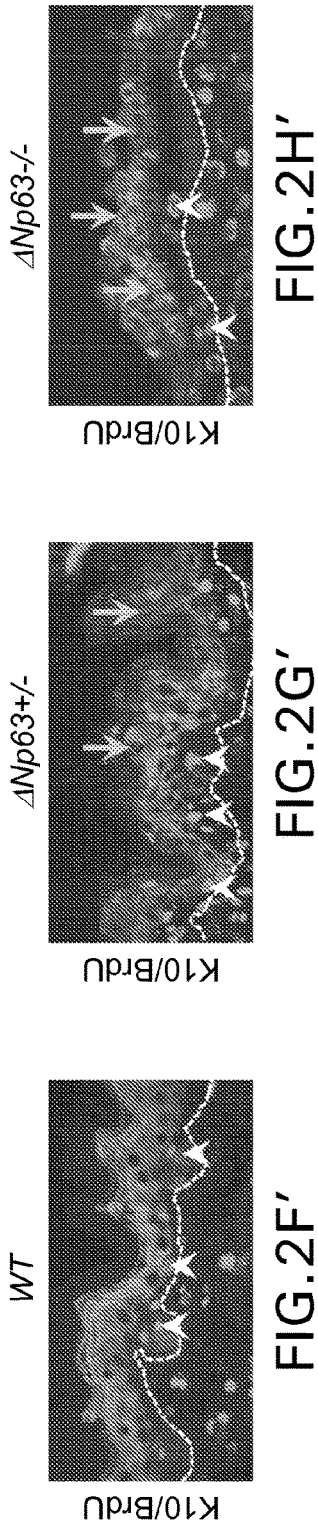

*fl/fl*

*Δ/Δ*

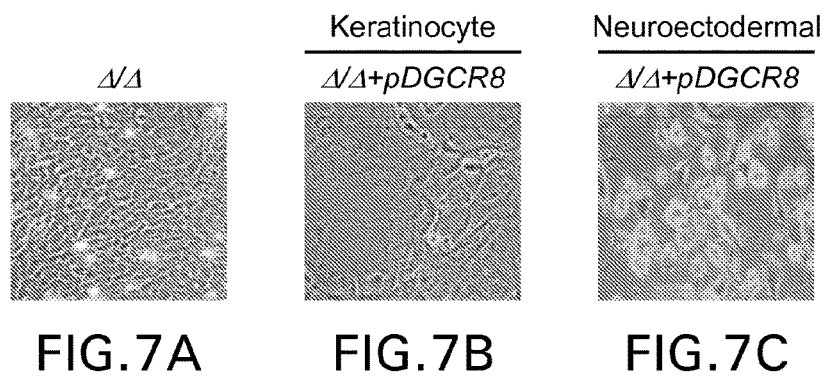
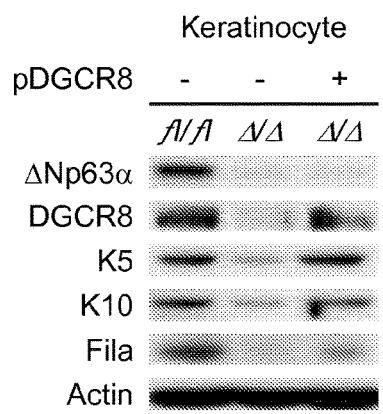 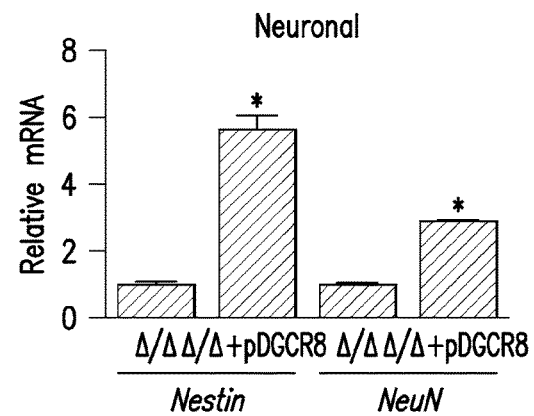
FIG.7D  FIG.7E

Wild-Type Mouse ES
H & E

ΔNp63-/- Epidermal
H & E

ΔNp63-/- Epidermal + DGCR8
H & E

Wild-Type Mouse ES
DGCR8

ΔNp63-/- Epidermal
DGCR8

ΔNp63-/- Epidermal + DGCR8
DGCR8

Wild-Type Mouse ES
Brachyury (Mesoderm)

ΔNp63-/- Epidermal
Brachyury (Mesoderm)

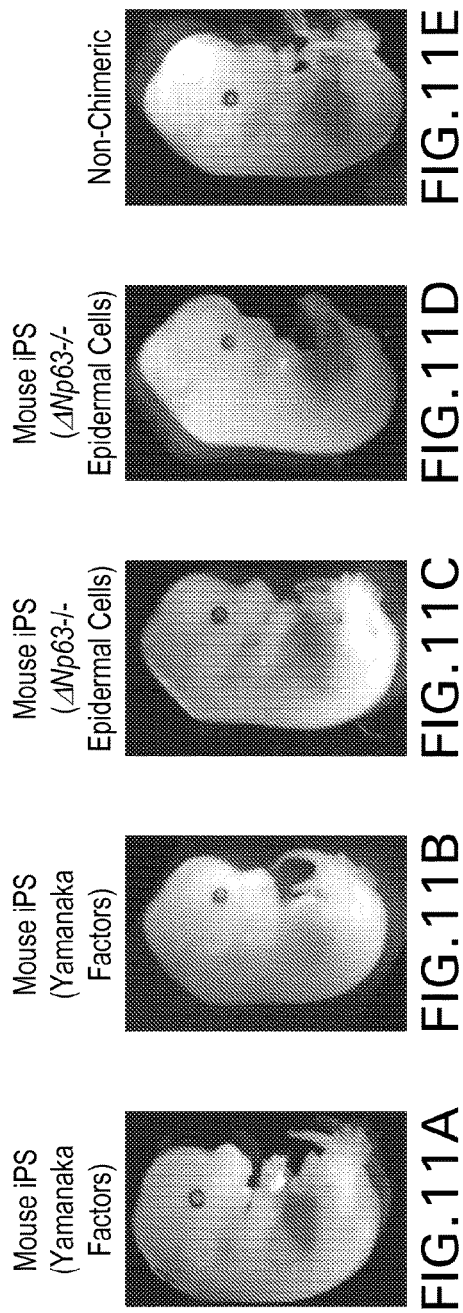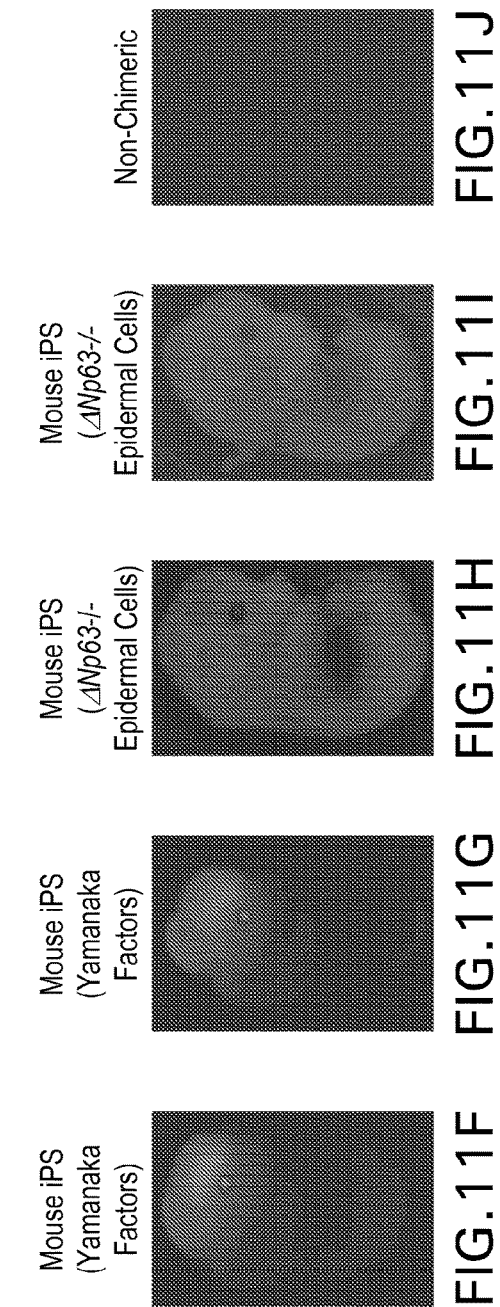

Mouse iPS
(Yamanaka
Factors)

Mouse iPS
(Yamanaka
Factors)

Mouse iPS
(ΔNp63-/-
Epidermal Cells)

Mouse iPS
(ΔNp63-/-
Epidermal Cells)

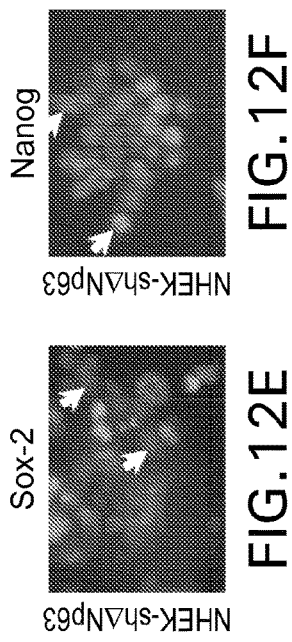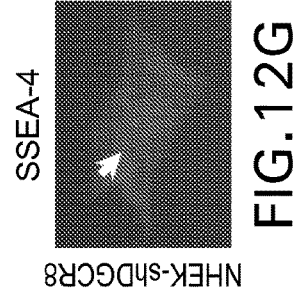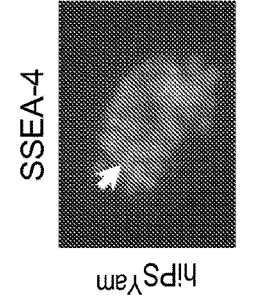

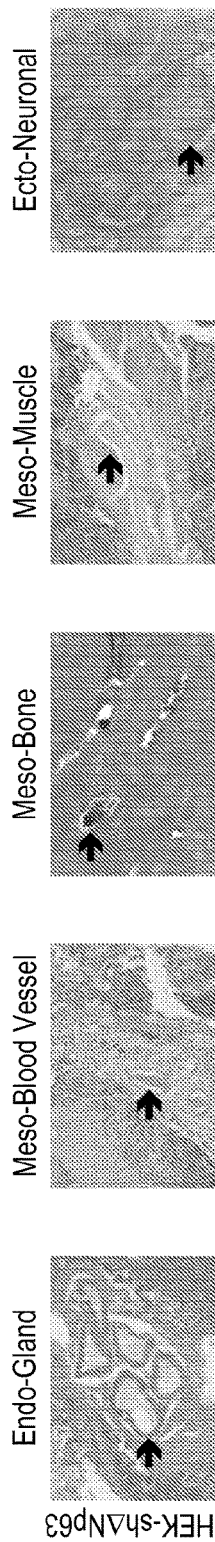
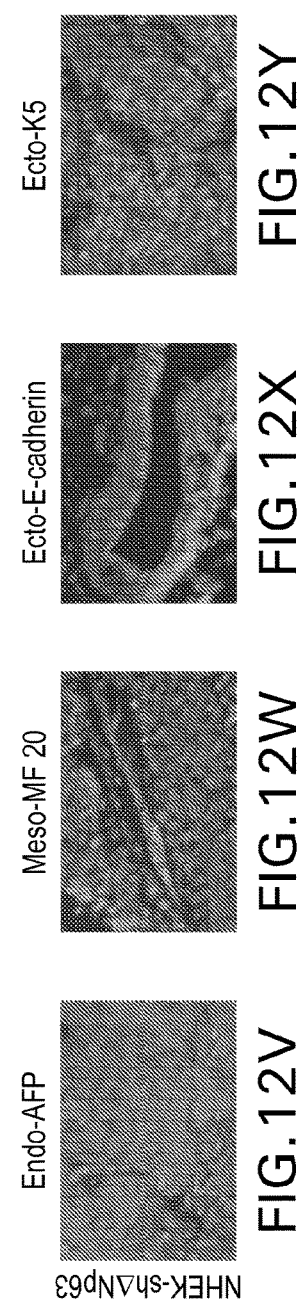
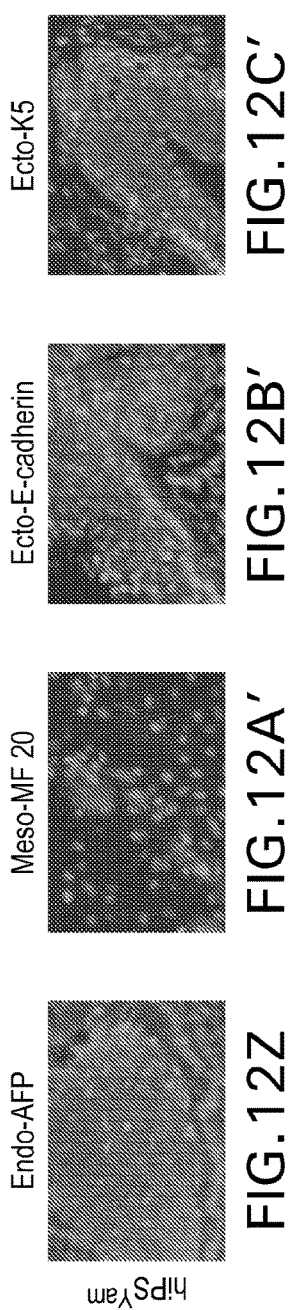

mES Cells

ΔNp63fl/fl Epidermal

ΔNp63-/- Epidermal

| - DGCR8 | + DGCR8 |

ΔNp63Δ/Δ Epidermal

| - DGCR8 | + DGCR8 |

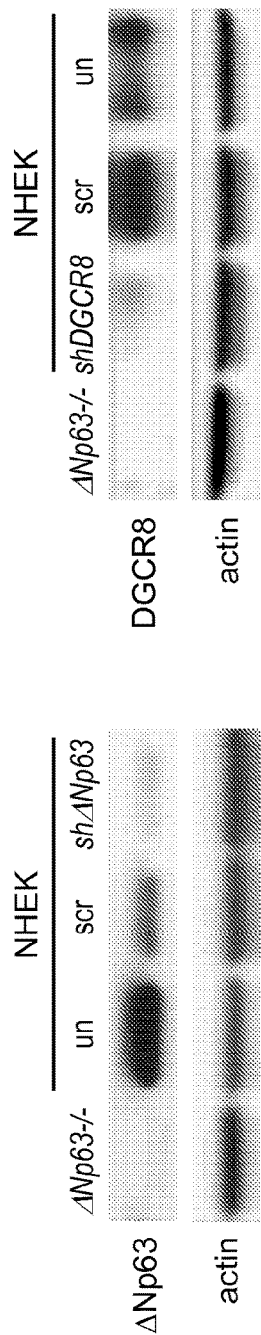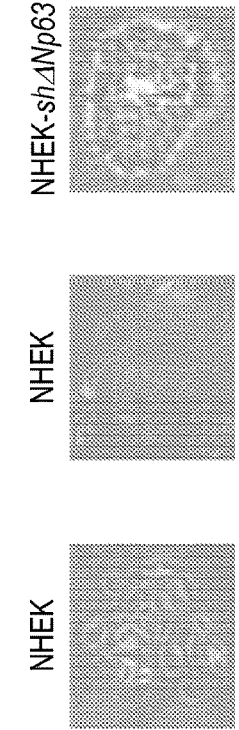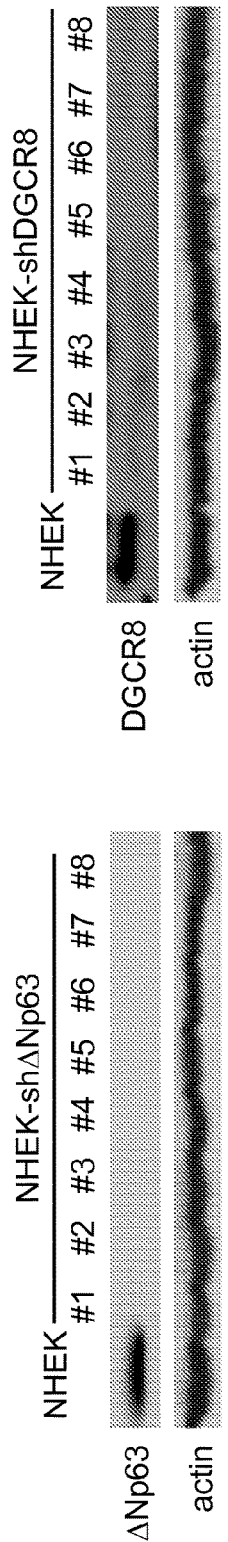

SEQUENCE LISTING

```
<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<223> OTHER INFORMATION: Synthetic primer

<400> SEQUENCE: 1
acagtcctct gctttcagc                                                  19

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
```

```
cacacagcac tggccttgc                                                  19

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
ttaggtggat ccctaggaag ag                                              22

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
cacacagcac tggccttgc                                                  19

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
tacagctcct ggaggatccc atgc                                            24

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
tgggcggcat ggtgcaagtt                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
cggtgctaac cagcgttttc                                                 20

<210> SEQ ID NO 8
<211> LENGTH: 23
<212> TYPE: DNA
<213> ORGANISM: Artificial Sequence
<220> FEATURE:
<223> OTHER INFORMATION: Synthetic primer

<400> SEQUENCE: 8
agtcaccttg gtgcctctca tag                                             23

<210> SEQ ID NO 9
<211> LENGTH: 21
<212> TYPE: DNA
<213> ORGANISM: Artificial Sequence
```

```
<220> FEATURE:
<223> OTHER INFORMATION: Synthetic primer

<400> SEQUENCE: 9
aaacaggtgg caaggcttct t                                        21

<210> SEQ ID NO 10
<211> LENGTH: 25
<212> TYPE: DNA
<213> ORGANISM: Artificial Sequence
<220> FEATURE:
<223> OTHER INFORMATION: Synthetic primer

<400> SEQUENCE: 10 cattttttc tgtggatctt ttggt                                     25

<210> SEQ ID NO 11
<211> LENGTH: 19
<212> TYPE: DNA
<213> ORGANISM: Artificial Sequence
<220> FEATURE:
<223> OTHER INFORMATION: Synthetic primer

<400> SEQUENCE: 11
cacagggcag gcagatcag                                           19

<210> SEQ ID NO 12
<211> LENGTH: 24
<212> TYPE: DNA
<213> ORGANISM: Artificial Sequence
<220> FEATURE:
<223> OTHER INFORMATION: Synthetic primer

<400> SEQUENCE: 12
caaatcaaaa tctgcatcca tagg                                     24

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
gccctcctgc ctgtaaacct                                          20

<210> SEQ ID NO 14
<211> LENGTH: 28
<212> TYPE: DNA
<213> ORGANISM: Artificial Sequence
<220> FEATURE:
<223> OTHER INFORMATION: Synthetic primer

<400> SEQUENCE: 14
ccgctcgagg cttctagttg tctattcc                                 28

<210> SEQ ID NO 15
<211> LENGTH: 28
<212> TYPE: DNA
<213> ORGANISM: Artificial Sequence
<220> FEATURE:
<223> OTHER INFORMATION: Synthetic primer

<400> SEQUENCE: 15
ggaagatctg ctcaccagat agcttgga                                 28
```

```
<210> SEQ ID NO 16
<211> LENGTH: 40
<212> TYPE: DNA
<213> ORGANISM: Artificial Sequence
<220> FEATURE:
<223> OTHER INFORMATION: Synthetic primer

<400> SEQUENCE: 16
atgcctgtct aaagtcactt ttgtgcctct cataggcctg                    40

<210> SEQ ID NO 17
<211> LENGTH: 44
<212> TYPE: DNA
<213> ORGANISM: Artificial Sequence
<220> FEATURE:
<223> OTHER INFORMATION: Synthetic primer

<400> SEQUENCE: 17
gcatgtatct cctaagaagc ttttccacct gtttacaaca ccag               44

<210> SEQ ID NO 18
<211> LENGTH: 44
<212> TYPE: DNA
<213> ORGANISM: Artificial Sequence
<220> FEATURE:
<223> OTHER INFORMATION: Synthetic primer

<400> SEQUENCE: 18
tggtgcctct cataggcctg tttttatctc ctaagaagcc ttgc               44

<210> SEQ ID NO 19
<211> LENGTH: 25
<212> TYPE: DNA
<213> ORGANISM: Artificial Sequence
<220> FEATURE:
<223> OTHER INFORMATION: Synthetic primer

<400> SEQUENCE: 19
ggatcccatg gagacagatg agagc                                    25

<210> SEQ ID NO 20
<211> LENGTH: 23
<212> TYPE: DNA
<213> ORGANISM: Artificial Sequence
<220> FEATURE:
<223> OTHER INFORMATION: Synthetic primer

<400> SEQUENCE: 20
gaattcggtg cacaggggct cac                                      23

<210> SEQ ID NO 21
<211> LENGTH: 10
<212> TYPE: DNA
<213> ORGANISM: Artificial Sequence
<220> FEATURE:
<223> OTHER INFORMATION: Synthetic primer

<400> SEQUENCE: 21
ctgcatgtat                                                     10

<210> SEQ ID NO 22
<211> LENGTH: 9
<212> TYPE: DNA
<213> ORGANISM: Artificial Sequence
<220> FEATURE:
<223> OTHER INFORMATION: Synthetic primer
```

```
<400> SEQUENCE: 22 ctcctaaga                                                                    9

<210> SEQ ID NO 23
<211> LENGTH: 10
<212> TYPE: DNA
<213> ORGANISM: Artificial Sequence
<220> FEATURE:
<223> OTHER INFORMATION: Synthetic primer

<400> SEQUENCE: 23
agccttgcca                                                                  10

<210> SEQ ID NO 24
<211> LENGTH: 10
<212> TYPE: DNA
<213> ORGANISM: Artificial Sequence
<220> FEATURE:
<223> OTHER INFORMATION: Synthetic primer

<400> SEQUENCE: 24
ttccatgtgg                                                                  10

<210> SEQ ID NO 25
<211> LENGTH: 6
<212> TYPE: DNA
<213> ORGANISM: Artificial Sequence
<220> FEATURE:
<223> OTHER INFORMATION: Synthetic primer

<400> SEQUENCE: 25 tctcct                                                                       6

<210> SEQ ID NO 26
<211> LENGTH: 10
<212> TYPE: DNA
<213> ORGANISM: Artificial Sequence
<220> FEATURE:
<223> OTHER INFORMATION: Synthetic primer

<400> SEQUENCE: 26
cccctagacc                                                                  10

<210> SEQ ID NO 27
<211> LENGTH: 10
<212> TYPE: DNA
<213> ORGANISM: Artificial Sequence
<220> FEATURE:
<223> OTHER INFORMATION: Synthetic primer

<400> SEQUENCE: 27
ctgtttttat                                                                  10

<210> SEQ ID NO 28
<211> LENGTH: 10
<212> TYPE: DNA
<213> ORGANISM: Artificial Sequence
<220> FEATURE:
<223> OTHER INFORMATION: Synthetic primer

<400> SEQUENCE: 28
agcttttcca                                                                  10
```

GENERATION OF HUMAN INDUCED PLURIPOTENT STEM CELLS USING NUCLEIC ACID SEQUENCES THAT INHIBIT Δ-NP63 AND DGCR8

The present application is a national phase application under 35 U.S.C. § 371 of International Application No. PCT/US2013/037186, filed Apr. 18, 2013, which claims the priority benefit of U.S. provisional application No. 61/635,491, filed Apr. 19, 2012, the entire contents of each of which are incorporated herein by reference.

The invention was made with government support under Grant Nos. CA134796 and CA091846 awarded by the National Institutes of Health. The government has certain rights in the invention.

BACKGROUND OF THE INVENTION

1. Field of the Invention

The present invention generally concerns at least the fields of cell biology, molecular biology, and medicine. In particular cases, the present invention concerns methods and compositions related to preparation of induced pluripotent stem cells.

2. Description of Related Art

The factors required to reprogram adult somatic cells to induced pluripotent stem (iPS) cells is an area of intense research. The introduction of defined factors, such as Oct4, Sox2, Klf4, and c-myc, gives rise to the efficient reprogramming of fibroblasts to iPS cells (Takahashi and Yamanaka, 2006). Cells deficient for p53 also show enhanced ability for reprogramming with the addition of Oct4 and Sox2 only (Hong et al., 2009; Kawamura et al., 2009; Li et al., 2009; Marion et al., 2009; Utikal et al., 2009). Unfortunately, overexpression of oncogenes or down regulation of tumor suppressor genes while leading to the generation of cells that are pluripotent can also lead to the production of tumorigenic cells (Li et al., 2009). Consequently, an alternative method for creating iPS cells from somatic cells is desirable.

Both miRNAs and the p53 family member, p63, have been implicated in processes that control stem cell proliferation and cell fate determination (Koster et al., 2004; Mills et al., 1999; Senoo et al., 2007; Su et al., 2009b; Yang et al., 1999). As demonstrated using genetically engineered mice, p63 is critical for the development and maintenance of stratified epithelial tissues (Mills et al., 1999; Yang et al., 1999). Mice lacking p63 cannot form skin, have craniofacial and skeletal defects and die within hours after birth. These defects are partially due to the functions of p63 as a transcriptional regulator of genes involved in multiple processes in skin development including epithelial stem cell proliferation, differentiation, and adhesion (Carroll et al., 2007; Flores, 2007; Ihrie et al., 2005; Koster et al., 2007; Senoo et al., 2007). While it is clear that p63 plays a crucial role in epidermal morphogenesis, its roles as an essential gene in stem cell proliferation and/or differentiation are still not well understood. The controversial roles of p63 in epidermal development are due, at least in part, to the complexity of the gene and existence of multiple isoforms (Yang et al., 2006). There are two major isoforms, those with a transactivation domain (TAp63) that structurally resemble p53 and those lacking this domain (ΔNp63); however, ΔNp63 also transcriptionally regulates unique target genes shown to be involved in limb and epidermal morphogenesis (Cho et al., 2010; Koster et al., 2007).

SUMMARY OF THE INVENTION

Embodiments of the present invention encompass methods and compositions related to stem cell and tissue engineering. In particular embodiments, the present invention concerns methods and compositions that relate to production of induced pluripotent stem cells and in certain embodiments these induced pluripotent stem cells are subject to conditions to produce differentiated cells, including in the form of tissue. The tissue comprising the induced pluripotent stem cells may be provided to an individual in need thereof, for example an individual with a wound, an individual with cosmetic needs, or an individual with a medical condition, all of which cell or tissue repair would be beneficial. Exemplary medical conditions include heart failure, burns, vascular disease, Parkinson's disease, lung disease, neurodegeneration, chronic obstructive pulmonary disease, emphysema, and so forth.

In certain embodiments, induced pluripotent stem cells are generated by methods of the invention wherein one or more types of adult somatic cells are provided one or more agents that knock down or downregulate ΔNp63 or DGCR8 expression. In some embodiments of the invention, there is a method of generating an induced pluripotent stem cell from an adult somatic cell, comprising the step of introducing to an adult somatic cell an agent that downregulates expression of ΔNp63 or DGCR8 in the somatic cell. Although in some aspects the somatic cell may be of any type, in specific embodiments the somatic cell is an epidermal cell, such as a keratinocyte, for example. In specific embodiments, the somatic cell is a cell other than an epidermal cell, such as a fibroblast, other cells of epithelial origin (mammary, lung, intestinal), or blood cells, for example.

Agents employed for downregulation of ΔNp63 or DGCR8 may be of any kind so long as there is a detectable level of downregulation of ΔNp63 or DGCR8 expression or so long as there is a noticeable effect of the somatic cell having pluripotent cell characteristics. In specific embodiments the agent is a nucleic acid, a polypeptide, a peptide, a small molecule, a zinc finger nuclease, or a mixture thereof. In cases wherein the agent is a nucleic acid, the agent may directly target the ΔNp63 or DGCR8 mRNA. In specific embodiments, the nucleic acid is shRNA, miRNA, siRNA, and so forth. Any nucleic acid of the invention that targets ΔNp63 or DGCR8 may be present on an expression vector, such as a lentiviral vector, a retroviral vector, an adenoviral vector, or a plasmid.

In some embodiments of the method, the induced pluripotent stem cells are analyzed for expression of one or more genes, including one or more genes whose expression is indicative of an induced pluripotent stem cell phenotype. In specific cases, the cells are assayed for expression of one or more genes selected from the group consisting of Oct4, Sox2, Klf4, and Nanog.

In some embodiments of the invention, induced pluripotent stem cells are subjected to conditions to produce a differentiated cell. The differentiated cell may be of any kind, and a skilled artisan recognizes how to tailor differentiation conditions to result in the desired differentiated cell. In specific cases, the differentiated cell is a neuron, blood cell, muscle cell, or skin cell, for example. Differentiation conditions include culturing cells ex vivo in media containing growth factors that induce differentiation into neuron, blood cell, muscle cell, or skin cell, for example. Differentiation can also be induced by injecting cells into mice to induce differentiation through non-cell autonomous factors provided by the stromal tissue of the host mouse.

In some embodiments of the invention, there is a method of repairing damaged tissue in an individual in need thereof, comprising the steps of introducing an agent to somatic cells from an individual, wherein the agent downregulates expression of ΔNp63 or DGCR8 in the somatic cells, to produce an induced pluripotent stem cells; subjecting the induced pluripotent stem cells to conditions to produce differentiated cells; and delivering the differentiated cells to the individual in need thereof. In certain cases, the differentiated cells are delivered to the individual in the form of tissue, such as skin tissue, muscle tissue, neurons, or blood, for example.

In certain embodiments of the invention, somatic cells are obtained from an individual for subjecting to methods of the invention, although in some cases somatic cells are obtained commercially. The somatic cells that are subject to generation of induced pluripotent stem cells, or differentiated cells therefrom, may be delivered to an individual by any suitable means in the art. In some cases, the induced pluripotent stem cells, produced by methods of the invention, or differentiated cells therefrom, are delivered to the individual from which the original adult somatic cells were obtained. However, in certain embodiments the induced pluripotent stem cells are delivered to the individual other than the individual(s) from which the somatic cells were obtained. Thus, in embodiments of the invention, the somatic cells are autologous to the individual or are allogeneic to the individual.

In particular embodiments of the invention, there is an induced pluripotent stem cell generated by methods of the invention and there is tissue comprised of cells generated by methods of the invention.

In some embodiments of the invention, ΔNp63 deletion or knockdown or downregulation re-programs epidermal cells to pluripotency, wherein the deletion of ΔNp63 may be part of the gene or the entire gene. In some embodiments, DGCR8 deletion or knockdown or downregulation re-programs epidermal cells to pluripotency, wherein the deletion of DGCR8 may be part or the entire gene.

The present invention concerns methods and compositions that provide an improvement over methods in the art. In some embodiments, there are methods that employ downregulation of the p53 family member, ΔNp63, or through downregulation of its transcriptional target DGCR8, in cells, including of adult keratinocytes. In particular embodiments, the p53 family member and p63 isoform, ΔNp63, is a critical transcriptional activator of a co-factor critical for miRNA processing, DGCR8. Low expression of key miRNAs in ΔNp63-deficient cells results in the failure to repress genes required for stem cell pluripotency, Oct4, Sox2, Klf4, and Nanog. Strikingly, ΔNp63−/− epidermal cells derived from genetically engineered knock out mice display profound defects in terminal differentiation and express markers and miRNAs of pluripotency at levels comparable to those in embryonic stem cells. Moreover, these cells can differentiate into multiple cell fates in vitro and in vivo. As an exemplary type of somatic cell, human primary keratinocytes depleted of ΔNp63 or DGCR8 become pluripotent. There is a novel role for ΔNp63 in the transcriptional regulation of DGCR8 to maintain stem cell pluripotency. Importantly, the present invention encompasses a simple method of generating human iPS cells through the knockdown of a single gene.

In still a further embodiment of the invention there is provided a mammalian cell (e.g., an iPS cell) comprising a genetic element encoding a zinc finger nuclease or inhibitory nucleic acid targeted to the ΔNp63 or DGCR8 gene. In a further aspect, there is provided a mammalian cell, such as an iPS cell, that comprises a zinc finger nuclease polypeptide targeted to the ΔNp63 or DGCR8 gene. In some aspects, a genetic element can be integrated into the genome of the cell (e.g., randomly or a specific locus, such as AAV integration site). However, in other aspects, the genetic element is not integrated into the genome of the cell, such as a genetic element comprised on an RNA or episomal vector. In certain aspects, the genetic element is further defined as an expression vector, such as a lentiviral vector, a retroviral vector, an adenoviral vector, an episomal vector or a plasmid. In still further aspects, the genetic element is or encodes and inhibitory RNA such as a shRNA, siRNA, or miRNA. In further aspects, a genetic element further comprises one or more additional coding regions such as a coding region for expression of a screenable or selectable marker.

In yet a further embodiment there is provided a method of providing a differentiated cell population comprising: (a) obtaining a population of iPS cells according to the embodiments (e.g., comprising a genetic element encoding inhibitory nucleic acid targeted to the ΔNp63 or DGCR8 gene or comprising zinc finger nuclease polypeptide targeted to the ΔNp63 or DGCR8 gene); and (b) culturing the cells in conditions effective to differentiate the iPS cells into a differentiated cell population. For example, in some aspects, step (b) culturing the cells comprises culturing the cells in a defined media comprising one or more growth factors. In certain aspects, a method of the embodiments further comprises selecting or screening for cells that have lost the genetic element. For example, such a screening or selecting can be performed before, after or essentially simultaneously with step (b). In further aspects, a methods of the embodiments is further defined a method of providing a differentiated cell population that comprises neuronal cells, mast cells, pancreatic beta cells, cardiomyocytes, or hepatocytes. In some aspects, ceils for use according to the embodiments are mouse, rat or human cells.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
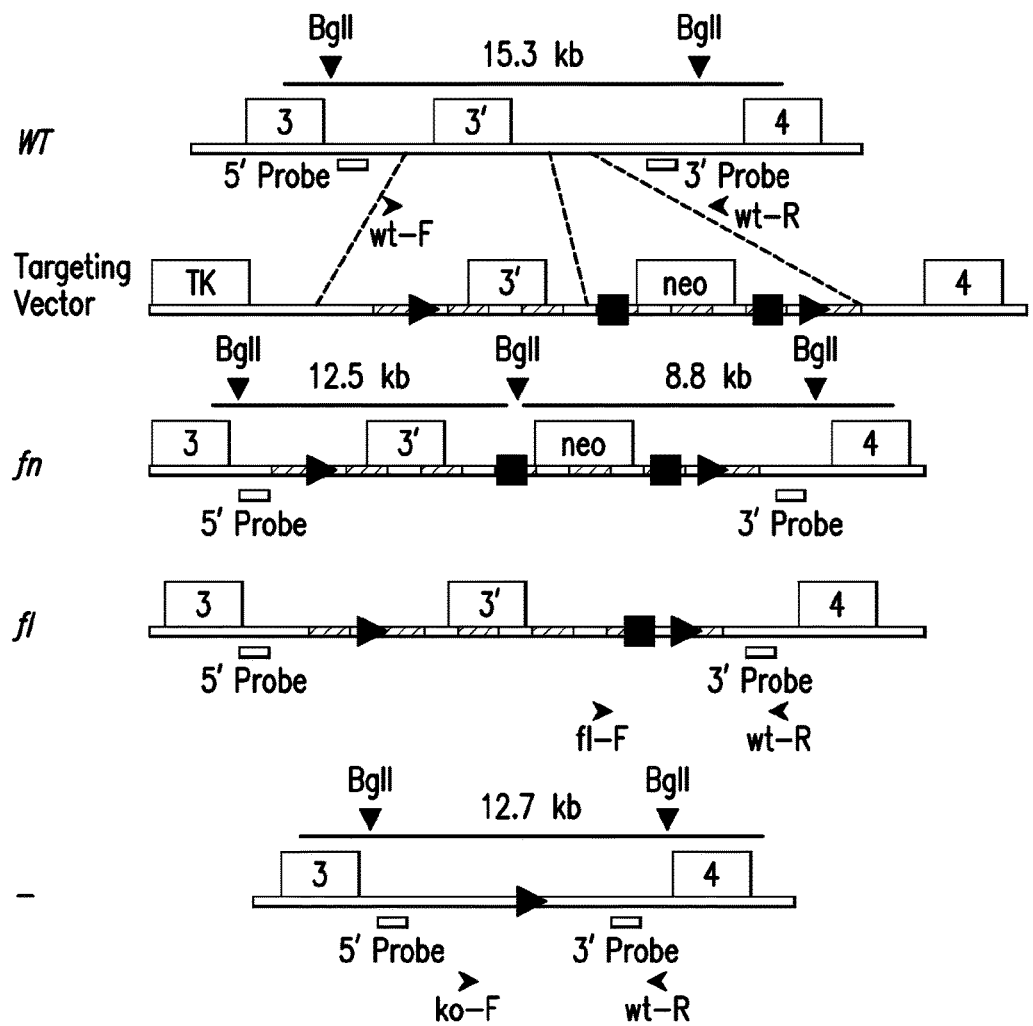
FIG. 1. Generation of ΔNp63fl/fl conditional and ΔNp63−/− knock out mice. A) The ΔNp63 targeting vector was generated by inserting loxP sites (triangles) flanking exon 3' and a neomycin cassette (neo) flanked by frt sites (squares). Locations of primers used for genotyping are indicated by arrows. The targeted region of the allele is depicted by a dashed line. Flox neo (fn) mice were crossed to the FLPeR mice expressing the flp recombinase to delete the neo cassette in vivo and to generate the flox (fl) allele. The knock out (KO) allele is shown after cre recombination. B) Southern analysis of genomic DNA from: ΔNp63$^{fn/+}$, ΔNp63$^{fn/fn}$, ΔNp63$^{+/+}$ and ΔNp63$^{-/-}$ mice. C) PCR analysis of genomic DNA from: ΔNp63$^{fl/+}$, ΔNp63$^{fl/fl}$, ΔNp63$^{+/+}$ and ΔNp63$^{-/-}$ mice. D) Quantitative (q) RT-PCR analysis of ΔNp63 mRNA from E9.5 and E18.5 wild-type and ΔNp63$^{-/-}$ embryos. Asterisks indicate statistical significance, ($p<0.001$). E) Western blot analysis for ΔNp63 using epidermal cells derived from wild-type and ΔNp63$^{-/-}$ embryos (E18.5) (left panel) and p53−/−;p63−/− MEFs expressing ΔNp63α and ΔNp63β cDNAs. Actin was used as a loading control. F) qRT-PCR analysis of TAp63 mRNA from E9.5 and E18.5 wild-type and ΔNp63$^{-/-}$ embryos. qRT-PCR values are normalized to GAPDH. G-J) Embryos at day E18.5 of the following genotypes: wild-type (G), ΔNp63+/− (H), ΔNp63−/− (I), and p63−/− (J). Arrows in panel (H) indicate extra folds of skin and in panel (I) indicate non-adherent skin. K-N) Hematoxylin and eosin (H&E) stained cross sections of the skin of E18.5 embryos of the indicated genotypes.

The roles of microRNAs (miRNAs) and the miRNA processing machinery in the regulation of stem cell biology are not well understood. Here, the p53 family member and p63 isoform, ΔNp63, is shown to be a critical transcriptional activator of a co-factor critical for miRNA processing, DGCR8. This regulation results in a unique miRNA signature critical for reprogramming cells to pluripotency. Strikingly, ΔNp63−/− epidermal cells display profound defects in terminal differentiation and express markers and miRNAs of pluripotency at levels comparable to those in embryonic stem cells and fibroblasts induce to pluripotency using the Yamanaka factors. Moreover, ΔNp63−/− epidermal cells can differentiate into multiple cell fates in vitro, in vivo, and can contribute to the germline. Human primary keratinocytes depleted of ΔNp63 or DGCR8 can be reprogrammed in 6 days and express a unique miRNA and gene expression signature that is similar to human iPS cells. The data presented herein reveal a novel role for ΔNp63 in the transcriptional regulation of DGCR8 to maintain stem cell pluripotency. In one embodiment, a simple method of generating human iPS cells through the knockdown of a single gene in a rapid fashion is provided.

The invention provides a novel way to generate induced pluripotent stem (iPS) cells from somatic cells, such as human epidermal keratinocytes, using knock down or downregulation of one gene, including ΔNp63 or DGCR8. Epidermal keratinocytes are readily accessible from skin biopsies from a patient, for example. Epidermal keratinocytes can be induced to generate pluripotent stem cells by knock down of either ΔNp63 or DGCR8 using lentiviral shRNAs or other means, as an exemplary embodiment. These pluripotent stem cells can then be used to generate differentiated cells and tissues to repair damaged tissues in a patient. Exemplary compositions of the invention include at least induced pluripotent stem (iPS) cells, differentiated cell types derived from these stem cells, and engineered tissues derived from these iPS cells, i.e., skin, blood, muscle, neurons. Induced pluripotent cells of the invention may differentiate into a variety of types, including endoderm, mesoderm, and ectoderm.

Current methods to generate iPS cells include the delivery of multiple genes, but in embodiments of the invention there are methods for the generation of iPS cells that are quick, efficient, and can be achieved by the downregulation of no more than one gene, including ΔNp63 or DGCR8. In alternative embodiments, however, both ΔNp63 and DGCR8 are downregulated in the same cell.

In specific embodiments of the invention, to characterize the role of ΔNp63 in skin development (merely as an example of tissue development), the inventors generated ΔNp63 conditional knock out mice (ΔNp63fl/fl), allowing for deletion of ΔNp63 and retention of the TAp63 isoforms in any tissue of interest. ΔNp63 knock out mice were then generated by intercrossing the ΔNp63 conditional knock out mice to germline specific cre transgenic mice (Zp3cre). Surprisingly, in contrast to the skin of $p63^{-/-}$ mice, the $\Delta Np63^{-/-}$ mice developed a hyperproliferative, disorganized epidermis that expressed some markers of terminal differentiation. Epidermal cells derived from the epidermis of $\Delta Np63^{-/-}$ mice had the ability to self renew and phenotypically resembled embryonic stem cells. Indeed, epidermal cells deficient for ΔNp63 express high levels of Oct4, Sox2, and Nanog indicating that ΔNp63 is critical for silencing of these factors to induce terminal differentiation. The $DGCR8^{-/-}$ embryonic stem cells (ESCs) were found previously to display a hyperproliferative defect by failure of silencing pluripotency genes (Wang et al., 2007). Additionally, the phenotype of the epidermis of $\Delta Np63^{-/-}$ mice is reminiscent of the DGCR8 and Dicer conditional knockout mice with DGCR8 and Dicer ablated in the skin (Yi et al., 2006; Yi et al., 2009). ΔNp63 transcriptionally activates DGCR8 and in turn represses Oct4, Sox2 and Nanog through regulation of a unique miRNA signature critical for reprogramming (Li et al., 2010; Lin et al., 2009a; Lin et al., 2008; Peter, 2009; Tay et al., 2008; Xu et al., 2009). ΔNp63 deficient epidermal cells had the capacity to self renew, expressed a miRNA signature that was similar to that of embryonic and iPS cells, and could be differentiated into multiple cell fates in vitro and in vivo. The inventors were able to recapitulate the iPS cell-like phenotype in normal human epidermal keratinocytes (NHEKs) by knocking down ΔNp63 or DGCR8. The data indicate that down regulation of ΔNp63 or DGCR8 in cells derived from the epidermis are reprogrammed to a pluripotent state.

I. Definitions

The term "downregulates" or "knockdown" as used herein refers to reduction of expression of a gene product (RNA or protein).

The term "induced pluripotent stem cell" as used herein refers to a somatic cell that has acquired characteristics of an embryonic stem cell. These cells can proliferate indefinitely, have an increase doubling time, express proteins that are expressed in embryonic stem cells (Oct4, Sox2, and Nanog are some examples), and can form teratomas and give rise to viable chimeric mice, for example.

As used herein, the term "somatic cell" refers to any diploid cell forming the body of an organism.

II. Delivery of Cells

In embodiments of the invention, cells generated by methods of the invention are delivered to a mammal. The cells may be induced pluripotent stem cells of the invention or cells differentiated therefrom. Cells may be delivered in the differentiated state where cells were differentiated ex vivo into cells or tissues of a specific type, skin for example. Undifferentiated cells could also be delivered on a substrate or scaffold. These cells would be differentiated in vivo. Differentiation would be stimulated by the microenvironment, in particular embodiments of the invention.

Cell delivery vehicles are known in the art and may be employed to deliver induced pluripotent stem cells of the invention or cells differentiated therefrom. In at least some cases, cell delivery vehicles comprise a matrix (such as of natural or synthetic materials or a combination thereof) that can facilitate transplantation of the cells into a mammalian host. Cell delivery vehicles are useful to provide cell attachment sites that are beneficial to transplantation. In specific embodiments, the vehicle is non-immunogenic, injectable, biodegradable, and/or has a physiological pH and temperature to avoid pH shock and hypothermia. In some embodiments one can modify the vehicle such that appropriate signals can be included (e.g., growth factors, extracellular matrix proteins) to provide boundaries against continued cellular differentiation, for example. In some embodiments, hydrogels are employed as cell delivery vehicles, such as alginate, self-assembling peptides, fibrin, collagen I, cross-linked hyaluronate, or PEGDA.

III. Nucleic Acid-Based Expression Systems

In embodiments of the invention, there is a nucleic acid-based agent that targets ΔNp63 or DGCR8. In specific embodiments, the nucleic acid agent is present on a vector for expression in a eukaryotic cell.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art. Nonlimiting examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), and human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences.

Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5 methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Components of the present invention may be a viral vector that target ΔNp63 or DGCR8. Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in the compositions of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses are useful as delivery vectors because of their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid (e.g., one comprising an a targeting nucleic acid of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

5. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

k. Extra-Chromosomal Vectors

In certain embodiments, methods of the present embodiments make use of extra-chromosomal genetic elements (e.g., for expression of zinc finger nucleases or inhibitory nucleic acid targeted to the ΔNp63 or DGCR8 gene). For example, extra-chromosomally replicating vectors, or vectors capable of replicating episomally (see U.S. Patent Publn. 20100003757, incorporated herein by reference) can be employed. In further aspects, RNA molecules (e.g., mRNAs, shRNAs, siRNAs, or miRNAs) can be employed.

A number of DNA viruses, such as adenoviruses, Simian vacuolating virus 40 (SV40), bovine papilloma virus (BPV), or budding yeast ARS (Autonomously Replicating Sequences)-containing plasmids also replicate extra-chromosomally in mammalian cells. These episomal plasmids are intrinsically free from all these disadvantages (Bode et al., 2001) associated with integrating vectors. A lymphotrophic herpes virus-based system including Epstein Barr Virus (EBV) may also replicate extra-chromosomally and help deliver genetic elements to somatic cells. For example, episomal vector-based approaches may employ elements of an EBV-based system. The useful EBV elements are OriP and EBNA-1, or their variants or functional equivalents.

An additional advantage of systems based on extra-chromosomal vectors is that these exogenous elements can be lost with time after being introduced into cells, leading to self-sustained iPS cells or cells differentiated from iPS cells that are essentially free of the original elements.

B. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Ex Vivo Transformation

Methods for tranfecting vascular cells and tissues removed from an organism in an ex vivo setting are known to those of skill in the art. For example, cannine endothelial cells have been genetically altered by retroival gene tranfer in vitro and transplanted into a canine (Wilson et al., 1989). In another example, yucatan minipig endothelial cells were tranfected by retrovirus in vitro and transplanted into an artery using a double-ballonw catheter (Nabel et al., 1989). Thus, it is contemplated that cells or tissues may be removed and tranfected ex vivo using the nucleic acids of the present invention. In particular aspects, the transplanted cells or tissues may be placed into an organism. In preferred facets, a nucleic acid is expressed in the transplated cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985). The amount of composition used may vary upon the nature of the antigen as well as the organelle, cell, tissue or organism used c. Electroporation In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

e. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

g. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

h. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the i. Microprojectile Bombardment Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

IV. Kits of the invention

Any of the compositions described herein may be comprised in a kit. The kits will thus comprise, in suitable container means, compositions related to the present invention. In specific aspects, the kit will comprise one or more agents that target ΔNp63 or DGCR8; somatic cells; expression vectors; induced pluripotent cells generated by methods of the invention; tissues generated by induced pluripotent cells generated by methods of the invention; and so forth.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the composition and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of a ΔNp63 Conditional Knockout Mouse

Figure 1B:
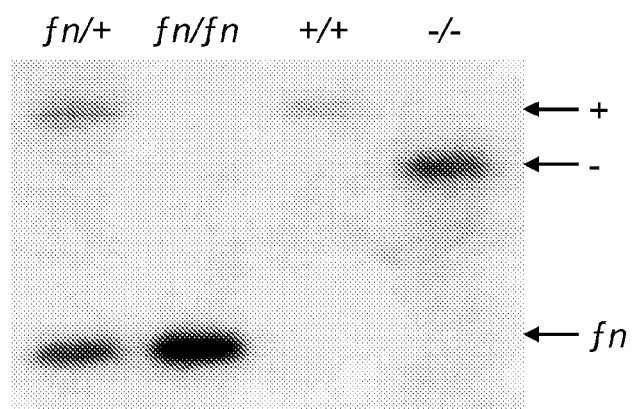

To understand the roles of ΔNp63 in vivo, a ΔNp63 conditional knockout mouse (ΔNp63fn) was generated using the cre-loxP system (FIG. 1) allowing for tissue-specific deletion of the ΔNp63 isoforms and retention of the TAp63 isoforms. LoxP sites were inserted in to the p63 gene flanking exon 3', which contains the translational start site of the ΔNp63 isoforms (FIG. 1A) and proper targeting confirmed by Southern blot analysis (FIG. 1B).

Figure 1C:
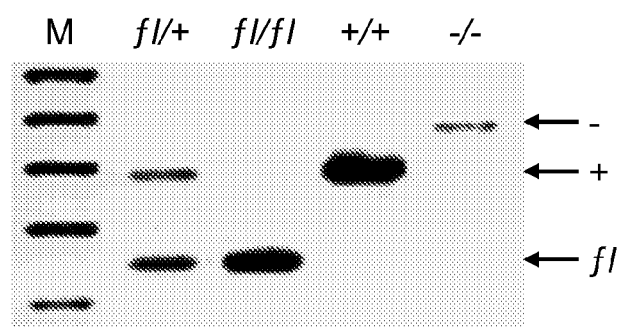
Figure 1D:
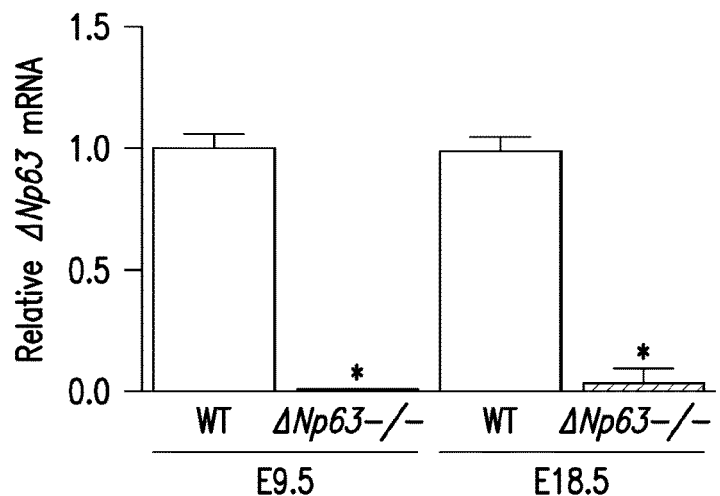
Figure 1E:
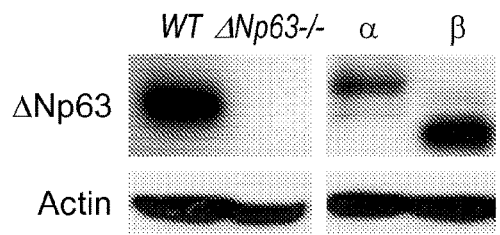
Figure 1F:
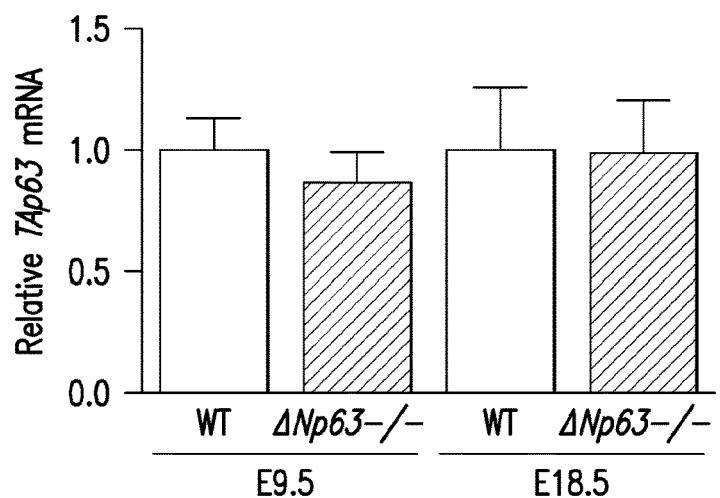

To understand the role of ΔNp63 in skin development, a ΔNp63$^{-/-}$ mouse was generated by intercrossing the ΔNp63 conditional knock out mice (ΔNp63$^{fn/fn}$) to FLPeR transgenic mice (Farley et al., 2000) to eliminate the intervening neo cassette (ΔNp63$^{fl/fl}$) (FIG. 1C). Resulting mice were intercrossed to female germline-specific cre transgenic mice (Zp3-cre) (Lewandoski et al., 1997) to generate ΔNp63$^{+/-}$ mice that were further intercrossed to generate ΔNp63$^{-/-}$ mice (FIGS. 1B and 1C). ΔNp63$^{-/-}$ mice are born at the proper Mendelian ratios but die within hours after birth similar to the p63-/- mice (Yang et al., 1999). Quantitative RT-PCR performed on embryos during different points in gestation, embryonic (E) 9.5 and 18.5, confirmed absence of ΔNp63 mRNA (p<0.0001) (FIG. 1D) and protein expression (FIG. 1E) with maintenance of wild-type levels of TAp63 mRNA expression (FIG. 1F).

Example 2

The Epidermis from ΔNp63-/- Displays Defects in Terminal Differentiation

The phenotype of the ΔNp63$^{-/-}$ mice was reminiscent of the p63$^{-/-}$ mice (Mills et al., 1999; Yang et al., 1999) and the ΔNp6$^{gfp/gfp}$ mice (Romano et al., 2012) (FIGS. 1G-J). The mice lacked limbs and had cleft lip and palate (compare FIGS. 1G, I, and J); however, the ΔNp63$^{-/-}$ mice developed a fragile epidermis that easily detached from the dermis (FIG. 1I). Microscopic analysis by hematoxylin and eosin (H&E) staining of E18.5 day embryos (FIGS. 1K-N) revealed the presence of rudimentary stratified epithelium with nests of basal epidermal cells (FIG. 1M). Interestingly, the ΔNp63$^{+/-}$ mice appeared to have excess folds of skin (FIG. 1H). Analysis of H&E cross sections of the epidermis of ΔNp63$^{+/-}$ mice revealed the presence of an expanded epidermal basal layer (FIG. 1L).

Figure 2I:
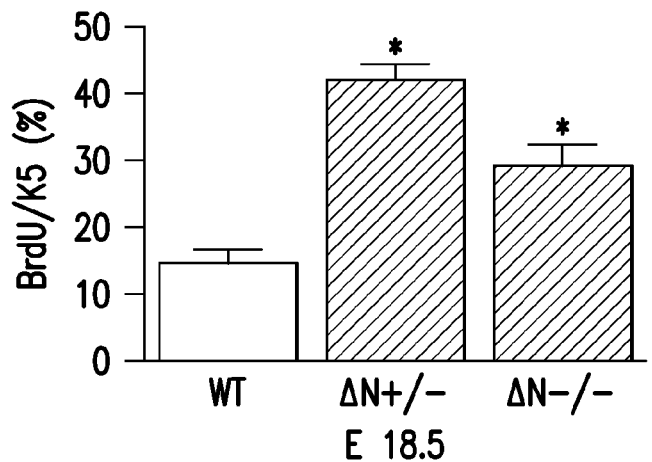
FIG. 2. ΔNp63 mutant mice exhibit epidermal abnormalities and defects in terminal differentiation. A-B') Immunofluorescence (IF) or immunohistochemistry (IHC) of skin from day E18.5 embryos of the indicated genotypes. Antibodies used are as follows: (A-D) keratin 5 (K5), (E-H) keratin 10 (K10), (1-L) keratin 1 (K1), (M-P) filaggrin (Fila), (Q-T) keratin 14 (K14) (green) and K10 (red), (U-X) keratin 8 (K8), and (Y-B') keratin 18 (K18). DAPI was used as a counterstain for IF and hematoxylin was used for IHC. Magnification 400×. In panel U, black arrowheads indicate examples of K8 positive cells in the basal layer. In panel Y, white arrowheads indicate examples of K18 positive cells in the basal layer. In panels V, W, Z, and A', arrows indicate examples of K8 or K18 positive cells in the spinous layer. C'-H') Double immunofluorescence using skin from E18.5 day embryos of the indicated genotypes. Antibodies used are as follows: (C'-E') keratin 5 (K5) and bromodeoxyuridine (BrdU) and (F'-H') keratin 10 (K10) and bromodeoxyuridine (BrdU). DAPI was used as a counterstain. Magnification 400×. In panels C'-H', white arrowheads indicate examples of BrdU positive cells in the basal layer. In panels F' and H', yellow arrows indicate examples of BrdU positive cells in the K10 expressing spinous layer. I') Percentage of K5 positive cells expressing BrdU. J') Percentage of K10 positive cells expressing BrdU. Asterisks indicate statistical significance, ($p<0.001$). The dashed lines denote the dermal/epidermal interface.
Figure 2J:
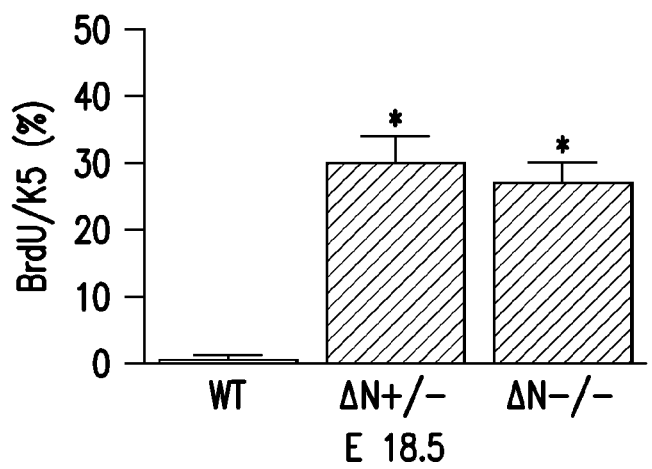

Given that the ΔNp63$^{+/-}$ embryos have an expanded epidermis with basaloid cells above the basal epithelium and that the ΔNp63$^{-/-}$ embryos also developed a disorganized epidermis, it was considered that loss of one or both alleles of ΔNp63 leads to defects in epidermal differentiation. To test this possibility, immunofluorescence was performed for markers of epidermal differentiation assessing the expression of keratin 5 (K5) and keratin 14 (K14) in the basal layer, keratin 10 (K10) and keratin 1 (K1) in the spinous layer, and filaggrin (Fila) in the granular layer. All markers of epidermal differentiation were appropriately expressed in wild-type embryos (FIGS. 2A, E, I, M, and Q). Interestingly, both ΔNp63$^{+/-}$ and ΔNp63$^{-/-}$ embryos expressed K5 in multiple epidermal layers (FIGS. 2B, C, R, and S). The ΔNp63$^{+/-}$ embryos also expressed K10, K1, and Fila in multiple epidermal layers that were several cell layers thick (FIGS. 2F, J, N, and R) in contrast to wild-type embryos, which expressed these markers in single or double cell layers (FIGS. 2E, I, M, and Q). The ΔNp63$^{-/-}$ embryos also expressed K10 and Fila in a few patches, but the expression was not as robust as in wild-type embryos (compare FIGS. 2G, K, and O to FIGS. 2E, I, and M) and was present only over 5%-10% of the embryo (FIGS. 2G, K, O, and S) suggesting a failure to terminally differentiate in the absence of ΔNp63. Given the apparent disorganization of the epidermis of ΔNp63$^{+/-}$ and ΔNp63$^{-/-}$ embryos, it was considered whether cells in the epidermis expressed multiple differentiation markers simultaneously. This was done by performing double immunofluorescence for K14 and K10. In wild-type embryos, K14 is expressed in the basal layer and K10 in the spinous layer of the epidermis (FIG. 2Q). In both the ΔNp63$^{+/-}$ and ΔNp63$^{-/-}$ embryos, there was overlapping expression of K14 and K10 in multiple layers of the epidermis (FIGS. 2R and S), indicating that ΔNp63 is required for proper epidermal differentiation. The epidermis of p63-/- embryos did not express any markers of epidermal differentiation (FIGS. 2D, H, L, P, T, X, and B') as reported previously (Su et al., 2009a; Yang et al., 1999).

Because of the appearance of basaloid cells in skin from ΔNp63$^{+/-}$ and ΔNp63$^{-/-}$ embryos, it was considered whether skin from these mice expressed keratins of simple epithelia (K8 and K18). While there were found a few positive cells in wild-type skin (FIGS. 2U and Y), skin from ΔNp63$^{+/-}$ and ΔNp63$^{-/-}$ embryos had many areas of positive cells expressed in layers above the basal epithelium (FIGS. 2V, W, Z, and A'), which are keratins characteristically expressed in simple epithelia. Interestingly, both epidermal stem cells and embryonic stem cells are positive for K8 and K18, indicating that the epidermal cells of ΔNp63$^{+/-}$ and ΔNp63$^{-/-}$ embryos have stem cell like properties, in particular embodiments of the invention.

Example 3

ΔNp63 Deficient Epidermal Cells are Hyperproliferative and Self-renew

The presence of an expanded epidermis expressing markers associated with embryonic stem cells in ΔNp63 mutant mice suggested that cells within this tissue are hyperproliferative and may have the ability to self-renew. To ask whether there was a hyperproliferation of epidermal cells in the skin of ΔNp63$^{+/-}$ and ΔNp63$^{-/-}$ embryos, the inventors injected pregnant ΔNp63$^{+/-}$ female mice carrying wild-type, ΔNp63$^{+/-}$ and ΔNp63$^{-/-}$ embryos with bromodeoxyuridine (BrdU) to mark cells in the S-phase of the cell cycle. By performing double immunofluorescence for BrdU and K5 (FIGS. 2C'-E') or BrdU and K10 (FIGS. 2F'-H'), the skin of ΔNp63$^{+/-}$ and ΔNp63$^{-/-}$ embryos have hyperproliferative and expanded basal and spinous layers as evidenced by the simultaneous expression of K5 and BrdU (FIGS. 2D', E', and I') and K10 and BrdU (FIGS. 2G', H', and J'), respectively.

Figure 3A:
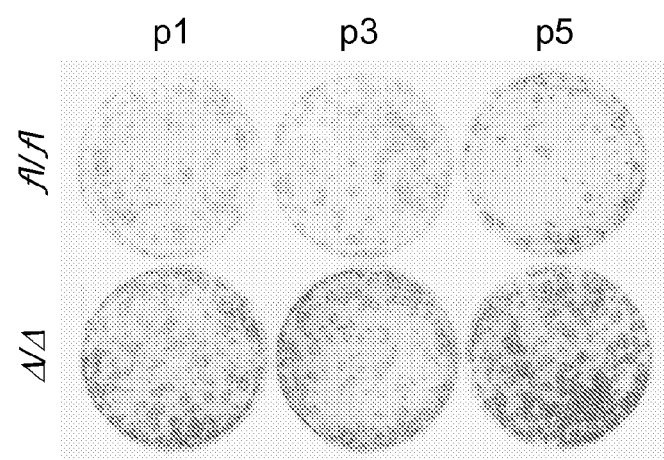
FIG. 3. ΔNp63 deficient epidermal cells are proliferative. A) Epidermal colonies from wild-type and ΔNp63 deficient epidermal cells (Δ/Δ) cultured on J2 3T3 feeder layers and stained with rhodamine B. Passages 1 (P1), 3 (P3), and 5 (P5) are shown. B) Immunostaining for BrdU and K5 in passage 3 and 5 wild-type (ΔNp63fl/fl) and ΔNp63Δ/Δ (Δ/Δ) epidermal cells. DAPI was used as a counterstain. White bar indicates 100 m. C) Quantification of BrdU incorporation in colonies after 8 days in culture. Passages 1, 3, and 5 are shown. Experiments performed in triplicate. Asterisks indicate statistical significance ($p<0.001$). D) Western blot analysis of epidermal cells derived from mice of the indicated genotypes grown under conditions that promote keratinocyte differentiation (High Ca2+) and using the indicated antibodies. Actin was used as a loading control. E) Western blot analysis of mouse embryonic stem cells (mES), ΔNp63−/−, ΔNp63Δ/Δ, and wild-type (ΔNp63fl/fl) epidermal cells using the indicated antibodies. Actin was used as loading control. F) Immunofluorescence (IF) performed on mouse iPS cells (iPSYam) or ΔNp63−/− epidermal cells using the indicated antibodies. DAPI was used as a counterstain. G) Heat map of promoter specific methylation assay using wild-type keratinocytes (WT-KC), ΔNp63−/− (Null), mouse ES cells (mES) and mouse iPS cells generated using the Yamanaka factors (miPSYam). Low methylation indicated in green and high methylation indicated in red.
Figure 3B:
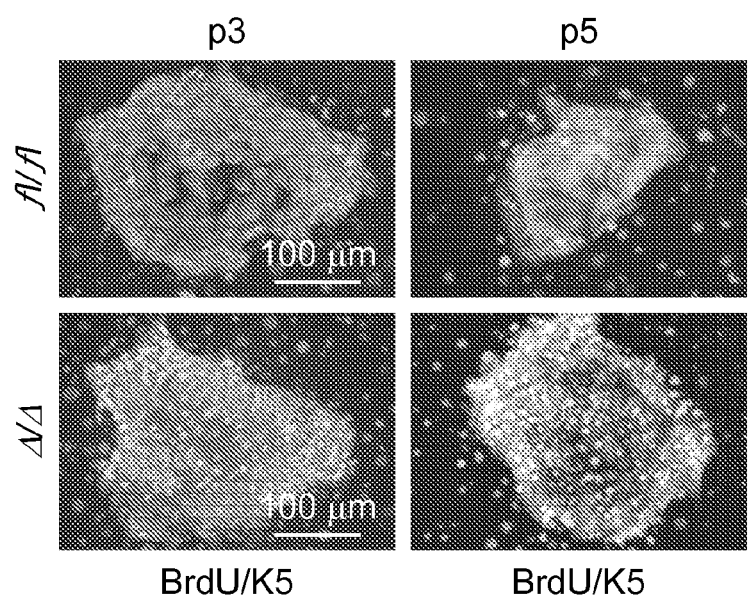
Figure 3C:
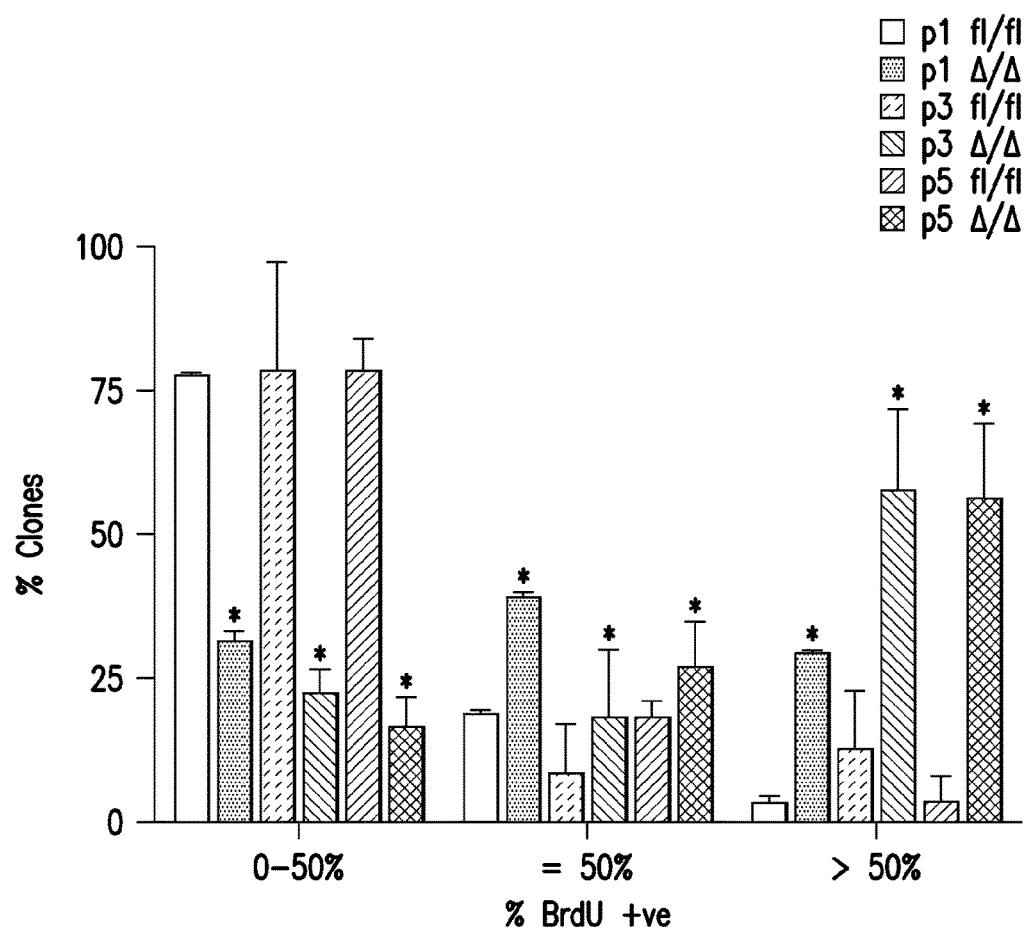
Figure 3D:
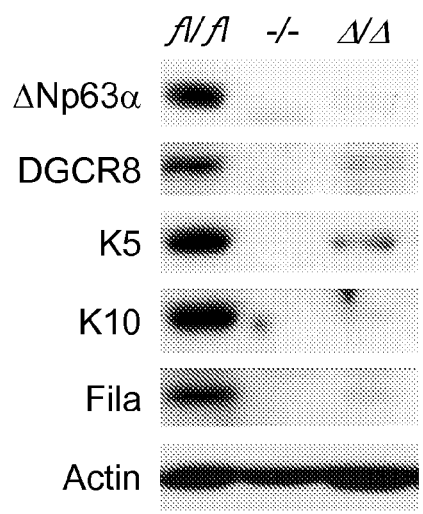

The presence of proliferative basaloid cells expressing markers of embryonic stem cells in the spinous and granular layers of the epidermis in ΔNp63 mutant mice (FIGS. 2V, W, Z, A', D', E', G', and H') indicated that the epidermal cells derived from these mice may have the ability to self-renew. To ask whether epidermal cells deficient for ΔNp63 hyperproliferate, ΔNp63fl/fl (wild-type) and ΔNp63Δ/Δ (ΔNp63 deficient) epidermal cells were serially passaged and stained with rhodamine B to score for the morphology of epidermal clones (FIG. 3A) (Barrandon and Green, 1987; Senoo et al., 2007; Su et al., 2009b). The inventors scored for the shape, size, and number of clones formed by each genotype. Large, round clones are indicative of a more stem-like morphology (Barrandon and Green, 1987; Senoo et al., 2007; Su et al., 2009b). Indeed, the number of large, round clones was greater in ΔNp63 deficient epidermal cells. To quantify the proliferative capacity of these clones, wild-type and ΔNp63-/- clones were labeled with BrdU after serial passaging (passages 1 through 5; 1000 cells/passage). Double immunofluorescence was performed using anti-BrdU and anti-K5 antibodies. The BrdU positivity in each colony was scored at each passage by counting the number of BrdU positive cells in each of 50 colonies (Table 1). Colonies of wild-type epidermal cells were initially proliferative (passage 1) but by passage 5 greater than 75% of these colonies incorporated very little BrdU (FIGS. 3B and C; Table 1), indicating an inability to proliferate beyond passage 5. In contrast, colonies derived from ΔNp63Δ/Δ epidermal cells incorporated high levels of BrdU even at passage 5 (FIGS. 3B and C; Table 1), indicating the ability to hyperproliferate. Greater than 50% of cells within the majority of ΔNp63Δ/Δ epidermal clones continued to incorporate BrdU at passage 5 (FIGS. 3B and C; Table 1).

in these cells compared to their wild-type counter parts (ΔNp63fl/fl) again indicating that ΔNp63 is required for commitment and terminal differentiation of keratinocytes (FIG. 3D).

Based on the ability of ΔNp63−/− and ΔNp63Δ/Δ epidermal cells to proliferate over several serial passages and the appearance of a stem cell like morphology, the inventors

TABLE 1

Quantification of BrdU positive keratinocytes

|   | Passage 1 | | Passage 3 | | Passage 5 | |
|---|---|---|---|---|---|---|
|   | ΔNp63fl/fl | ΔNp63Δ/Δ | ΔNp63fl/fl | ΔNp63Δ/Δ | ΔNp63fl/fl | ΔNp63Δ/Δ |
| 1 | 30% | 30% | 25% | 90% | 0% | 100% |
| 2 | 25% | 100% | 60% | 90% | 5% | 90% |
| 3 | 65% | 50% | 60% | 95% | 5% | 50% |
| 4 | 50% | 25% | 50% | 100% | 50% | 95% |
| 5 | 10% | 35% | 15% | 45% | 0% | 95% |
| 6 | 50% | 85% | 50% | 95% | 0% | 100% |
| 7 | 5% | 90% | 15% | 90% | 0% | 100% |
| 8 | 30% | 90% | 10% | 90% | 0% | 100% |
| 9 | 45% | 35% | 10% | 35% | 0% | 40% |
| 10 | 40% | 50% | 10% | 50% | 0% | 45% |
| 11 | 45% | 50% | 10% | 50% | 0% | 45% |
| 12 | 50% | 90% | 50% | 90% | 5% | 90% |
| 13 | 40% | 90% | 10% | 90% | 50% | 90% |
| 14 | 85% | 35% | 70% | 35% | 0% | 95% |
| 15 | 35% | 50% | 5% | 100% | 0% | 95% |
| 16 | 45% | 50% | 10% | 100% | 0% | 50% |
| 17 | 50% | 85% | 15% | 85% | 0% | 100% |
| 18 | 40% | 50% | 20% | 90% | 50% | 50% |
| 19 | 25% | 50% | 20% | 50% | 0% | 50% |
| 20 | 20% | 50% | 20% | 50% | 5% | 50% |
| 21 | 15% | 40% | 20% | 95% | 5% | 100% |
| 22 | 10% | 95% | 20% | 90% | 10% | 90% |
| 23 | 30% | 95% | 25% | 90% | 55% | 95% |
| 24 | 30% | 50% | 15% | 50% | 10% | 50% |
| 25 | 35% | 45% | 20% | 45% | 10% | 40% |
| 26 | 50% | 45% | 60% | 45% | 5% | 40% |
| 27 | 40% | 100% | 15% | 100% | 10% | 100% |
| 28 | 50% | 100% | 60% | 80% | 0% | 95% |
| 29 | 40% | 100% | 20% | 80% | 60% | 90% |
| 30 | 45% | 45% | 20% | 40% | 0% | 95% |
| 31 | 40% | 45% | 20% | 35% | 0% | 95% |
| 32 | 35% | 50% | 20% | 50% | 0% | 50% |
| 33 | 40% | 45% | 20% | 45% | 0% | 40% |
| 34 | 50% | 50% | 50% | 80% | 5% | 40% |
| 35 | 50% | 50% | 50% | 85% | 5% | 50% |
| 36 | 40% | 50% | 20% | 90% | 50% | 45% |
| 37 | 35% | 50% | 15% | 90% | 25% | 50% |
| 38 | 35% | 50% | 10% | 100% | 20% | 50% |
| 39 | 40% | 40% | 10% | 100% | 50% | 100% |
| 40 | 35% | 95% | 20% | 95% | 50% | 100% |
| 41 | 35% | 95% | 20% | 90% | 0% | 90% |
| 42 | 40% | 35% | 25% | 40% | 0% | 40% |
| 43 | 45% | 50% | 25% | 50% | 0% | 50% |
| 44 | 50% | 50% | 60% | 50% | 50% | 100% |
| 45 | 40% | 15% | 25% | 40% | 0% | 100% |
| 46 | 40% | 50% | 25% | 50% | 0% | 50% |
| 47 | 40% | 95% | 30% | 95% | 0% | 90% |
| 48 | 50% | 50% | 55% | 50% | 10% | 50% |
| 49 | 45% | 50% | 35% | 100% | 10% | 100% |
| 50 | 45% | 45% | 40% | 90% | 50% | 45% |
| AVERAGE | 39% | 59% | 28% | 73% | 13% | 73% |

Example 4

Figure 3E:
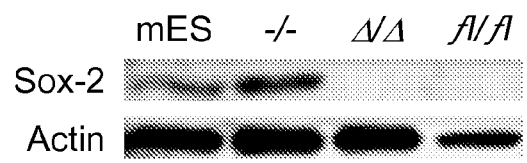
Figure 3F:
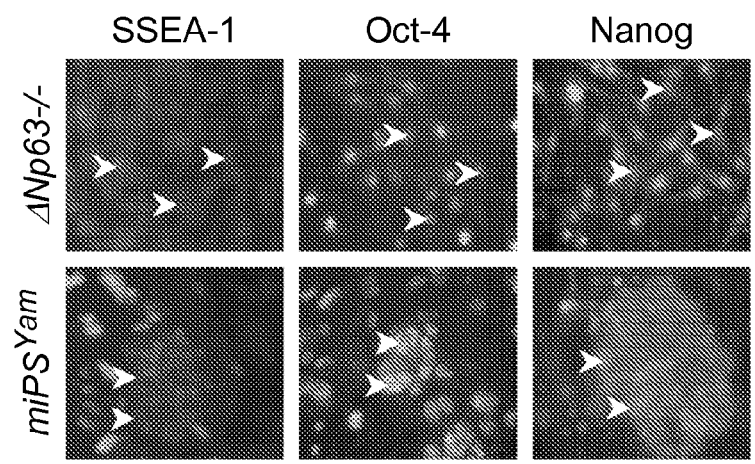

ΔNp63 Deficient Epidermal Cells Express High Levels of Factors Associated with Induced Pluripotency The inventors examined the expression levels of genes associated with epidermal differentiation in the ΔNp63−/− and ΔNp63Δ/Δ epidermal clones shown in FIGS. 3A and B and found very low expression of keratin 5, 10, and filaggrin asked whether these cells express Oct4, Sox2, Nanog, and stage specific embryonic antigen 1 (SSEA-1) by immunoblotting or by immunfluorescence (FIGS. 3E and F). Indeed, ΔNp63−/− cells express Oct4, Sox2, Nanog, and SSEA-1 at levels higher than wild-type keratinocytes and in some cases at similar levels to mouse ES and iPS cells generated by introduction of the Yamanaka factors (FIGS. 3E and F). These data indicate that ΔNp63−/− epidermal cells express factors associated with induced pluripotency.

Example 5

Figure 3G:
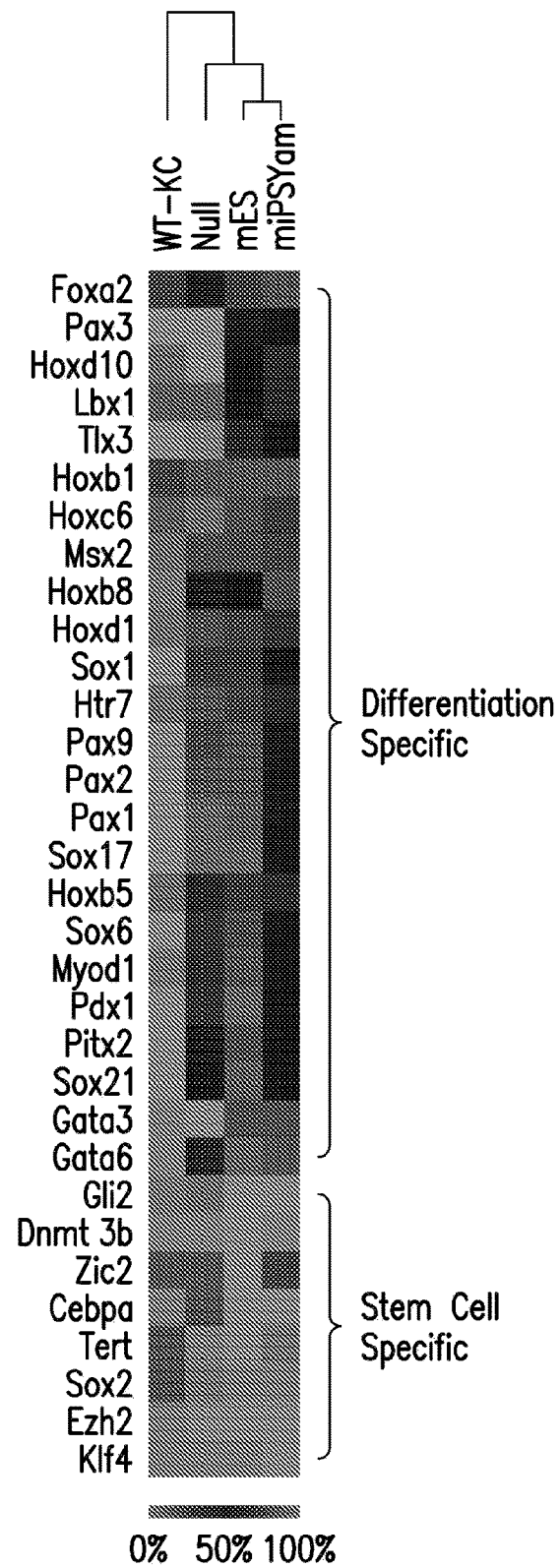

The Methylation Pattern of Gene Promoters in ΔNp63−/− Epidermal Cells is Similar to that of Mouse Embryonic Stem Cells Methylation patterns of genes associated with stem cell specification and differentiation are critical for the maintenance of pluripotency of stem cells. To determine the methylation pattern of gene promoters associated with stem cell specification or differentiation, the inventors assayed methylation patterns in wild-type keratinocytes, ΔNp63−/− epidermal cells, iPS cells generated using the Yamanaka factors (iPS$_{Yam}$), and mouse embryonic stem cells (FIG. 3G). The methylation of key genes associated with pluripotency had a similar signature in ΔNp63−/− epidermal cells, iPS$_{Yam}$, and mouse ES cells. These included Sox2 and Klf4, which were both unmethylated in this group of cells (FIG. 3G). Importantly, the inventors found a cluster of differentiation-specific genes including several Hox genes and Myod1 that were similarly methylated in ΔNp63−/− epidermal cells and ES cells but not iPS$_{Yam}$ cells (FIG. 3G). This is important because iPS cells retain methylation patterns of somatic cells (Marion et al., 2009), which is not the case in ΔNp63−/− epidermal cells. These data indicate that the ΔNp63−/− epidermal cells are more similar to mouse ES cells than to iPS cells generated with the Yamanaka factors.

Example 6

ΔNp63 Regulates a miRNA Program Through the Transcriptional Regulation of DGCR8

Figure 4A:
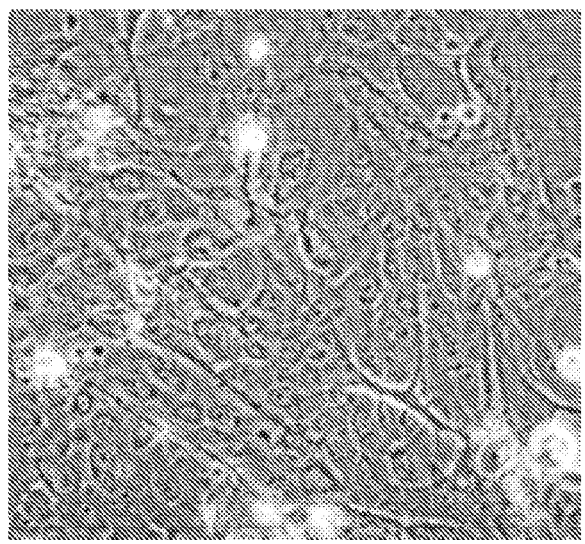
FIG. 4. DGCR8 is a transcriptional target of ΔNp63. A&B) Epidermal cells derived from the skin of ΔNp63 conditional knock out mice (fl/fl) (A) and ΔNp63fl/fl epidermal cells infected with adenovirus-cre for 6 hours to generate ΔNp63 deficient (Δ/Δ) epidermal cells (B).
Figure 4B:
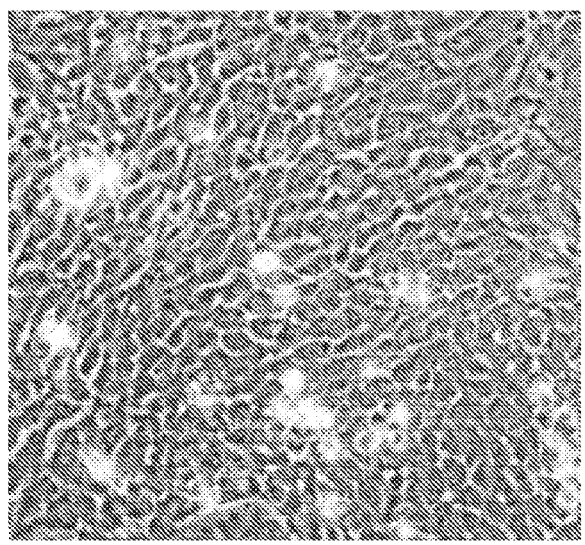

TAp63 transcriptionally regulates Dicer, a critical enzyme involved in miRNA biogenesis (Su et al., 2010). Additionally, mice lacking Dicer or DGCR8 expression in K14-expressing cells have a similar epidermal phenotype as the ΔNp63+/− and ΔNp63−/− mice (Teta et al., 2012; Yi et al., 2006; Yi et al., 2009). Interestingly, ΔNp63−/− epidermal cells exhibit a unique undifferentiated morphology that does not resemble keratinocytes. Moreover, when one ablates ΔNp63 by administering adenovirus-cre recombinase to ΔNp63fl/fl keratinocytes, a similar undifferentiated phenotype is observed within hours of ΔNp63 deletion (compare FIGS. 4A and B). The flat appearance of the wild-type (ΔNp63fl/fl) keratinocytes (FIG. 4A) begins to appear less differentiated (FIG. 4B) after ΔNp63 deletion (ΔNp63Δ/Δ). To further characterize epidermal cells deficient for ΔNp63, western blot analysis was performed using wild-type (ΔNp63fl/fl) or ΔNp63 deficient epidermal cells (ΔNp63−/−) grown in keratinocyte media for the expression of keratinocyte differentiation markers (K5, K10, and filaggrin). Epidermal cells lacking ΔNp63 grown in keratinocyte media do not express K5, K10, or filaggrin (FIG. 3D).

Figure 5A:
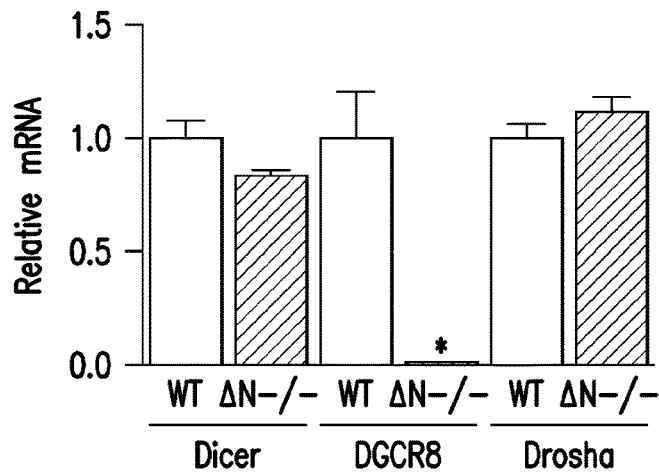
FIG. 5. DGCR8 is a transcriptional target of ΔNp63. A) qRT-PCR for Dicer, DGCR8 and Drosha using total RNA from wild-type (WT) and ΔNp63−/− (ΔN−/−) epidermal cells. B) qRT-PCR for DGCR8 using total RNA from wild-type (WT), ΔNp63−/− (ΔN−/−) and TAp63−/− epidermal cells. C) qRT-PCR of ChIP assay using wild-type (WT) and ΔNp63−/− (ΔN−/−) epidermal cells and indicating p63-binding site (site 1) or no binding of p63 to site 2 or non-specific binding site (NSBS). D) Schematic showing DGCR8-site 1 (dgcr8 S) and DGCR8-mutant of site 1 (dgcr8 Sm) luciferase reporter genes. E) Luciferase assay for DGCR8 in p53−/−;p63−/− MEFs transfected with the indicated p63 isoforms and the indicated luciferase reporter gene. Each bar represents the average of the fold activation of three independent experiments. The asterisks indicate statistical significance ($p<0.001$). F) Western blot analysis of mouse embryonic stem cells (mES), mouse induced pluripotent stem cells (miPSYam), wild type mouse keratinocytes (WT-KC) and ΔNp63−/− epidermal cells expressing DGCR8 (+) or not (−) using the indicated antibodies. Arrow indicates Oct4 specific band. Asterisk indicates non-specific band. Upper Oct4 blot is a longer exposure of the one immediately below it. Actin was used as loading control.
Figure 5B:
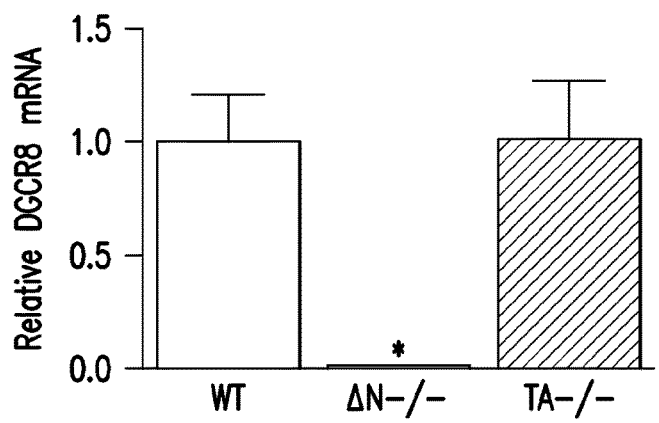
Figure 13A:
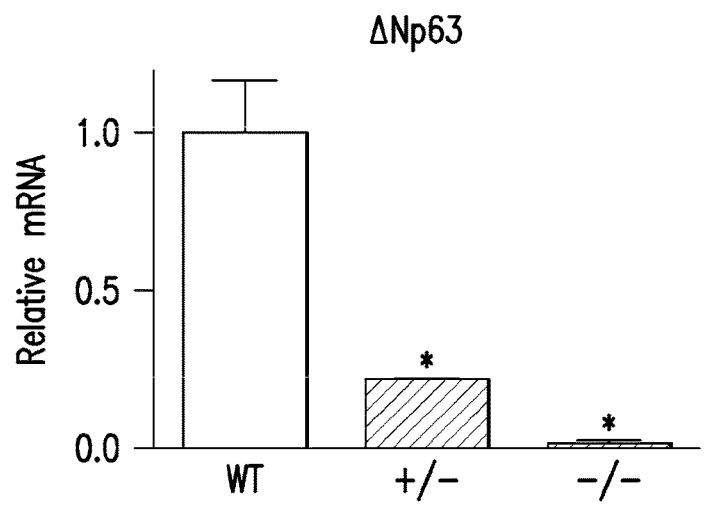
FIG. 13. DGCR8 expression is low in ΔNp63+/− and ΔNp63−/− epidermal cells. A&B) qRT-PCR for ΔNp63 (A) and DGCR8 (B) using total RNA from wild-type (WT), ΔNp63+/−(+/−), and ΔNp63−/− (−/−) epidermal cells. Values are normalized to GAPDH. Asterisks indicate statistical significance ($p<0.001$). C) Western blot analysis using lysates from wild-type (WT), ΔNp63+/−(+/−), and ΔNp63−/− (−/−) epidermal cells and the indicated antibodies. Actin was used as a loading control.
Figure 13B:
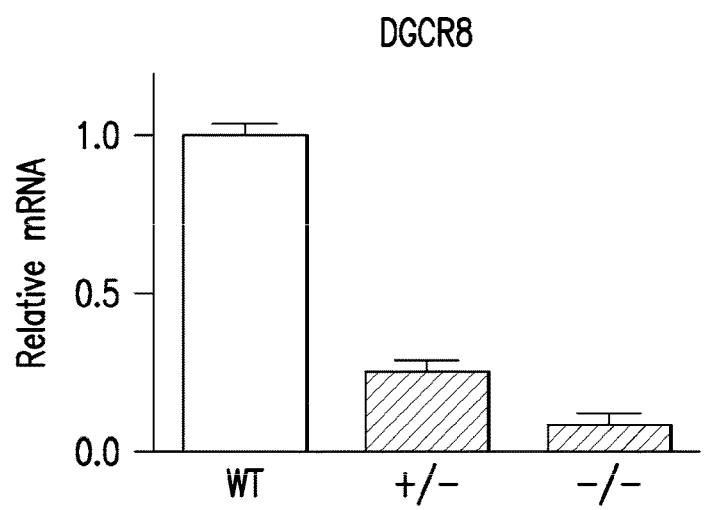
Figure 13C:
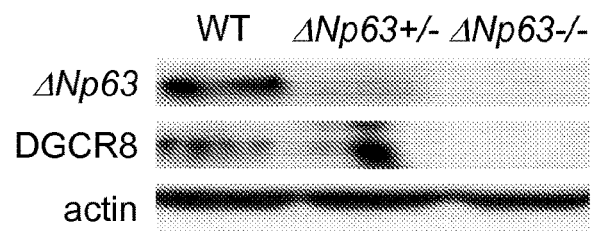

Additionally, many miRNAs were expressed at low levels in ΔNp63−/− epidermal cells. Therefore, it was considered whether ΔNp63 could be a transcriptional regulator of enzymes involved in miRNA biogenesis. To do this, qRT-PCR was performed for Dicer, DGCR8, and Drosha using total RNA derived from wild type and ΔNp63−/− epidermal cells. Interestingly, DGCR8 mRNA expression was markedly decreased in the ΔNp63−/− and ΔNp63+/− epidermal cells (FIGS. 5A, 13A, and 13B). DGCR8 protein levels are also low in the absence of ΔNp63−/− and ΔNp63+/− epidermal cells (FIGS. 3D, 5F, and 13C). It was considered whether TAp63 might be similarly transcriptionally regulating DGCR8. To address this question, qRT-PCR was performed for DGCR8 using total RNA isolated from TAp63−/− epidermal cells (FIG. 5B). DGCR8 mRNA is expressed at wild-type levels in the absence of TAp63, suggesting that ΔNp63 is a transcriptional regulator of DGCR8 and TAp63 is not.

To determine whether DGCR8 is a direct transcriptional target of ΔNp63, chromatin immunoprecipitation (ChIP) analysis was performed using p63 antibodies and primers specific for two putative p53/p63 binding sites that were identified within intron 1 of the DGCR8 promoter (Table 2).

TABLE 2 p63/p53 response elements

| Element | Location | Sequence | MM / spacer |
|---|---|---|---|
| DGCR8-1 | −3394 to −3366 | ctgCATGtat ctcctaaga agcCTTGcca (SEQ ID NO: 21, SEQ ID NO: 22, and SEQ ID NO: 23, respectively) | 5/9 |
| DGCR8-2 | −1459 to −1434 | ttcCATGtgg tctcct cccCTAGacc (SEQ ID NO: 24, SEQ ID NO: 25, and SEQ ID NO: 26, respectively) | 8/6 |

Figure 5C:
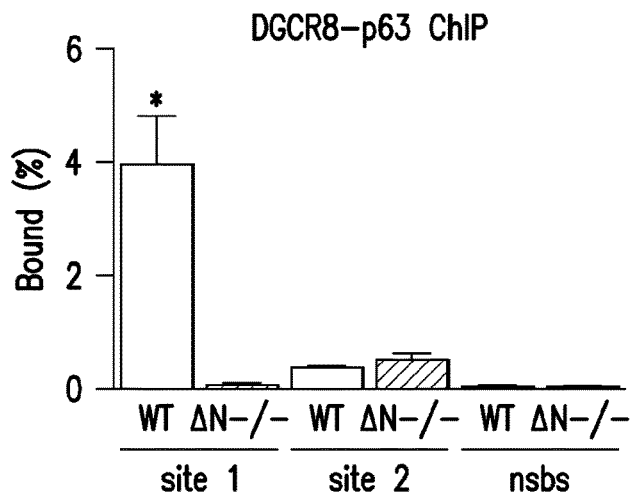

Sequences of elements assayed by ChIP analysis. MM indicates the number of mismatches to p63/p53 consensus binding site and spacer indicates the number of nucleotides within the spacer region.

p63 robustly binds to one of these sites (site 1) (FIG. 5C). The ability of p53 to bind to site 1 was tested, and there was no detectable significant binding, indicating that DGCR8 is a p63 target gene.

Figure 5D:
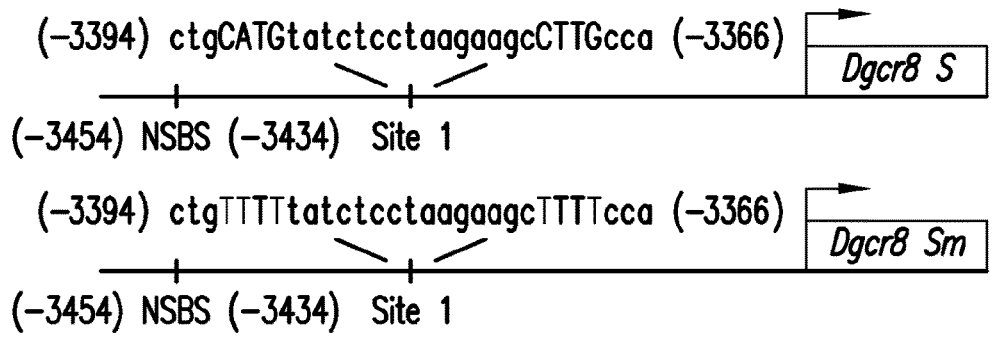
Figure 5E:
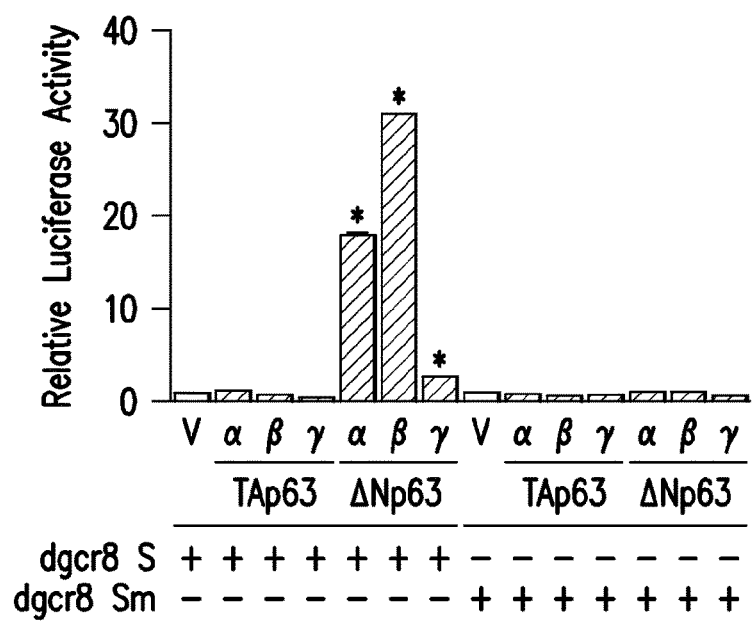
Figure 5F:
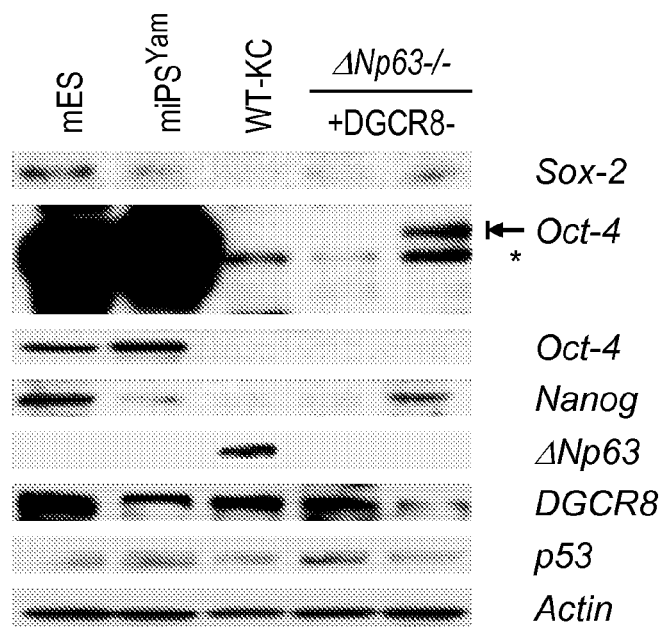

To determine whether p63 isoforms can transactivate a DGCR8-luciferase reporter gene, the inventors cloned the site bound to p63 in the ChIP assay (site 1) into a vector containing the luciferase reporter gene. The DGCR8-luciferase reporter gene (dgcr8 S-luc) (FIG. 5D) and each p63 isoform individually (TAp63α, β, γ or ΔNp63 α, β, γ) were co-transfected into p53−/−;p63−/− mouse embryonic fibroblasts (MEFs). Only the ΔNp63 isoforms could transactivate the reporter gene with ΔNp63α and β exhibiting the highest transactivation activity (FIG. 5E). To ask whether the cloned p63 binding site is critical for transactivation of the DGCR8-luciferase reporter gene, the p63 consensus site was mutated from (ctgCATGtat ctcctaaga agcCTTGcca; SEQ ID NOs:24, 25, and 26, respectively) to (ctgTTTTtat ctcctaaga agcTTTTcca; SEQ ID NOs:27, 25, and 28, respectively) using site-directed mutagenesis (FIG. 5D). None of the p63 isoforms transactivated the mutant DGCR8 reporter gene (dgcr8 Sm-luc) (FIG. 5E), indicating that ΔNp63 transcriptionally activates DGCR8 by binding to site 1.

Example 7

ΔNp63 Represses Oct4, Sox2, and Nanog Through Transcriptional Regulation of DGCR8

Figure 6A:
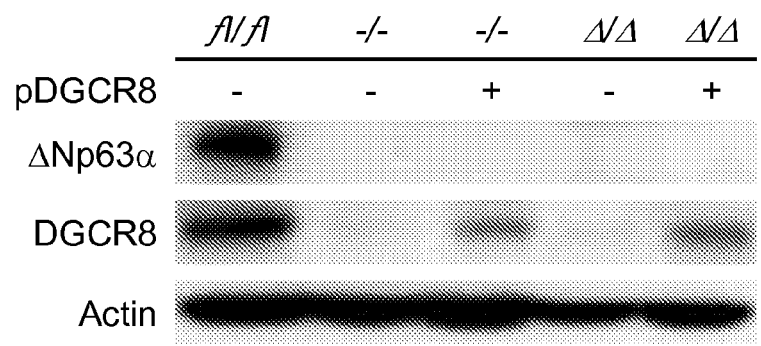
FIG. 6. ΔNp63 deficient epidermal cells are pluripotent. A) Western blot analysis of epidermal cells of the indicated genotypes with the antibodies shown. B-D) qRT-PCR using total RNA from epidermal cells of the indicated genotypes. Cells expressing DGCR8 are indicated by (pDGCR8). Expression of Oct4 (B), Sox2 (C), and Nanog (D) were analyzed. Asterisks indicate statistical significance ($p<0.001$). E) Western blot analysis of mouse embryonic stem cells (ES) and epidermal cells of the indicated genotypes using the antibodies shown.
Figure 6B:
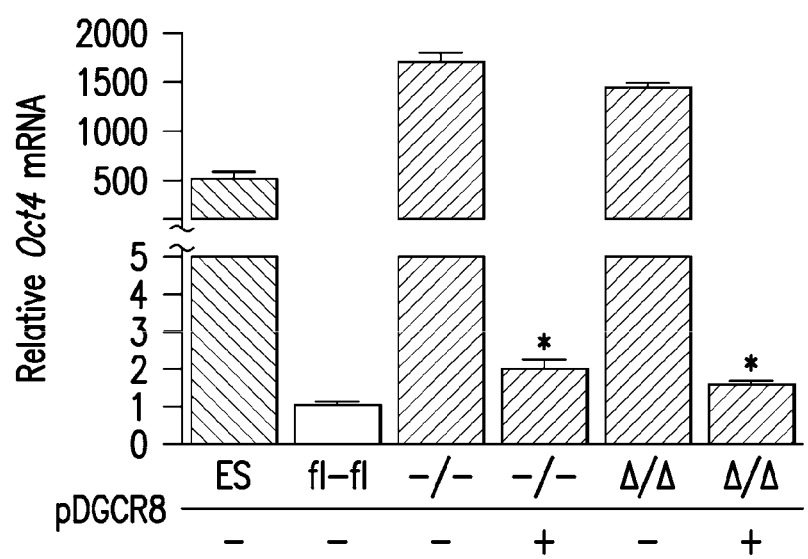
Figure 6C:
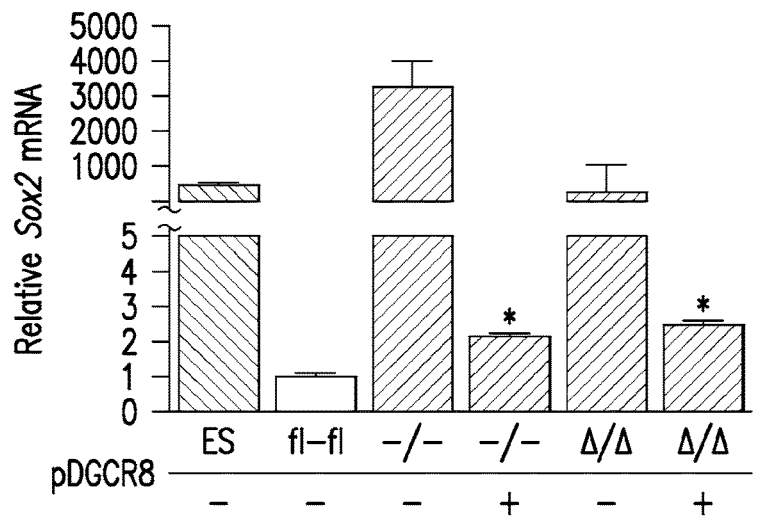
Figure 6D:
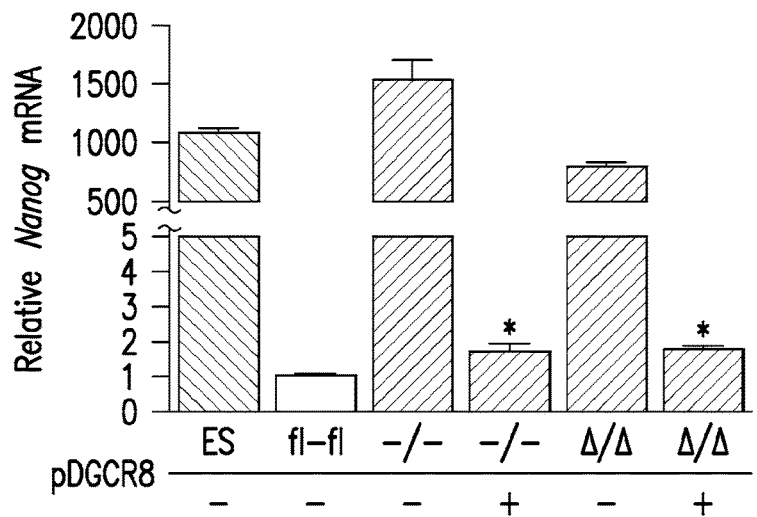
Figure 6E:
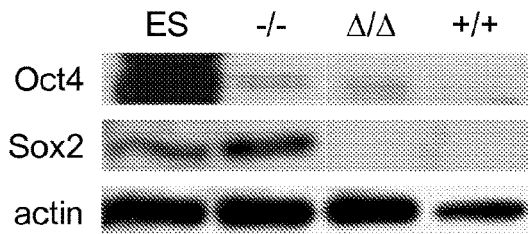

DGCR8 has been shown to be critical for repression of Oct4, Sox2, and Nanog expression (Wang et al., 2007), critical factors in the maintenance of stem cell pluripotency. To determine whether ΔNp63 and ΔNp63Δ/Δ epidermal cells express Oct4, Sox2, and Nanog, qRT-PCR was performed using total RNA from wild-type, ΔNp63 and ΔNp63Δ/Δ epidermal cells. ΔNp63 and ΔNp63Δ/Δ cells expressed these markers of pluripotency at comparable or higher levels than mouse embryonic stem cells (ES) (FIGS. 6A-E). To determine whether this was through regulation of DGCR8 by ΔNp63, the inventors transduced ΔNp63 and ΔNp63Δ/Δ cells with a DGCR8 expressing lentivirus (FIG. 6A) and found that the expression of Oct4, Sox2, and Nanog mRNA could be restored to levels found in wild-type keratinocytes (ΔNp63fl/fl) (FIG. 6B-D).

To determine whether ΔNp63−/− epidermal cells regulate expression of Oct4, Sox2, and Nanog through DGCR8, the inventors performed immunoblotting using lysates from ΔNp63−/− epidermal cells and ΔNp63−/− epidermal cells expressing DGCR8 and compared them to wild-type keratinocytes, mES and miPS$_{Yam}$ cells (FIG. 5F). ΔNp63−/− epidermal cells expressed Sox2 and Nanog at levels higher than that of miPS$_{Yam}$ cells and somewhat lower than levels expressed in mES cells (FIG. 5F). Expression of DGCR8 in ΔNp63−/− epidermal cells extinguished expression of Sox2 and Nanog (FIG. 5F). The pattern for Oct4 was similar in that it was expressed in ΔNp63−/− epidermal cells, albeit at lower levels than in mES and miPS$^{Yam}$ cells, and expression was again extinguished in ΔNp63−/− epidermal cells expressing DGCR8 (FIG. 5F). These data indicate that ΔNp63−/− epidermal cells express Sox2, Nanog, and Oct4 and these are repressed after expression of DGCR8. Taken together, these results suggest that increased expression of these pluripotency markers in the absence of ΔNp63 is through DGCR8.

Because cells deficient for p53 have been shown to have an enhanced ability to be reprogrammed (Andl et al., 2006; Anokye-Danso et al., 2011; Buganim et al., 2012; Hong et al., 2009; Kawamura et al., 2009), the inventors asked whether ΔNp63−/− epidermal cells express p53. Levels of p53 are comparable in ΔNp63−/− epidermal cells and in mES and miPS cells indicating that the increased proliferation and expression of Oct4, Sox2, and Nanog was not related to p53 status (FIG. 5F). The inventors also assayed for expression of ΔNp63 in these cells and found that while ΔNp63 is robustly expressed in wild-type keratinocytes, it is not expressed in mES or miPS cells suggesting that ΔNp63 is critical for commitment to keratinocyte differentiation (FIG. 5F).

Example 8

ΔNp63−/− Epidermal Cells, iPS, and Mouse ES Cells have a Similar miRNA and mRNA Signature To further characterize the ΔNp63−/− epidermal cells and to determine whether they had similar miRNA profiles to ES or iPS cells, a miRNA sequencing (miRNA-SEQ) study was performed using RNA isolated from wild-type keratinocytes, ΔNp63 deficient (ΔNp63−/−) epidermal cells, and ΔNp63 deficient epidermal cells expressing DGCR8 (ΔNp63−/−+DGCR8). Importantly, ΔNp63−/− epidermal cells had a miRNA profile similar to that found in ES cells (Houbaviy et al., 2003) or iPS cells (Li et al., 2010; Lin et al., 2009a; Peter, 2009). The inventors found a number of critical miRNAs that are expressed in ES and iPS cells to also be highly expressed in ΔNp63−/− epidermal cells, including miR-106b, miR-125b, miR-134, miR-296, miR-93, miR-17, miR-130a, miR-22, and miR-34a. The high expression of miRNAs associated with pluripotency was concomitant with low expression of miRNAs expressed in keratinocytes. In other words, ΔNp63−/− epidermal cells had very low expression of miR-203, miR-205, and the miR-200 family (miR-200a, miR-200b, miR-200c, miR-141, miR-145, miR-429). There were also a number of miRNAs that were distinct from the published ES and iPS miRNA profiles indicating that ΔNp63−/− epidermal cells have a unique miRNA signature that poises them for pluripotency. ΔNp63−/−+DGCR8 epidermal cells had a similar profile to wild-type keratinocytes indicating that re-expression of DGCR8 in ΔNp63−/− epidermal cells induces a miRNA signature similar to that seen in keratinocytes.

Because ΔNp63 transcriptionally activates DGCR8, the inventors determined the expression of miRNAs in the ΔNp63−/− epidermal cells. Importantly, there are critical microRNAs that have been shown to reprogram cells, such as miR-302 (Anokye-Danso et al., 2011). To determine the miRNA signature of the ΔNp63−/− epidermal cells, the inventors performed miRNA-Seq experiments on RNA isolated from ΔNp63−/− epidermal cells and compared them to wild-type keratinocytes, iPSYam, and mouse ES cells. The ΔNp63−/− epidermal cells had a similar miRNA signature to iPSYam and ES cells. Among the significantly upregulated miRNAs in ΔNp63−/− epidermal cells, iPSYam and ES cells were miR-290, miR-295, and miR-302, miRNAs that have been found to be critical for reprogramming (Anokye-Danso et al., 2011) or upregulated in iPS cells reprogrammed with the Yamanaka factors (Judson et al., 2009). In addition, a number of miRNAs were significantly down regulated in the ΔNp63−/− epidermal cells, iPSYam and ES cells, including miR-200a, miR-200b, miR-200c, miR-141, miR-203, miR-205, and miR-15b. Also, a set of seven miRNAs that were most significantly up or down regulated in the ΔNp63−/− epidermal cells also matched the expression pattern of miRNAs in mouse ES and mouse iPSYam. These miRNAs are miR-9-5, miR-23a, miR-146b, miR-200c/miR141, miR-31, miR-205, and miR-30b/c.

To determine whether these microRNAs are regulated in ΔNp63−/− epidermal cells through DGCR8, DGCR8 was expressed in ΔNp63−/− epidermal cells cultured in keratinocyte media (FIG. 5F). Importantly, the miRNA signature from these cells clustered with that of wild-type keratinocytes indicating that the critical miRNAs for pluripotency in these cells is controlled through DGCR8. There were also a number of miRNAs that were differentially regulated in ΔNp63−/− epidermal cells that were distinct from the published ES and iPS miRNA profiles indicating that ΔNp63−/− epidermal cells have a unique miRNA signature that poises them for pluripotency. Because Oct4 was present at lower levels in ΔNp63−/− epidermal cells than iPS cells generated using the Yamanaka factors, the inventors also performed RNA-Seq using RNA isolated from wild-type mouse keratinocytes, ΔNp63−/− epidermal cells, miPSYam and mES cells and found that the gene expression signature of the ΔNp63−/− epidermal cells most closely resembled the miPSYam and mES cells. These data suggest that factors other than high expression of Oct4 are critical for reprogramming in cells deficient for ΔNp63.

Example 9

ΔNp63 Deficient Epidermal Cells are Pluripotent and can Differentiate into Multiple Cell Fates In Vitro To determine whether ΔNp63 deficient cells could differentiate into different cell fates, ΔNp63Δ/Δ cells (FIG. 7A) were cultured under conditions permissive for keratinocyte (FIG. 7B) or neuronal differentiation (FIG. 7C). Because repression of genes involved in pluripotency in ΔNp63 deficient epidermal cells is dependent on expression of DGCR8, ΔNp63Δ/Δ epidermal cells expressing DGCR8 were cultured in keratinocyte differentiation media and cells exhibited a differentiated morphology (compare FIGS. 7A and B) and expressed markers of keratinocyte differentiation, similar to levels expressed in wild-type keratinocytes (FIG. 7D). These results again indicate that expression of DGCR8 is critical for the terminal differentiation of ΔNp63−/− epidermal cells and in its absence these cells express miRNAs that induce pluripotency and inhibit terminal differentiation.

Figure 14A:
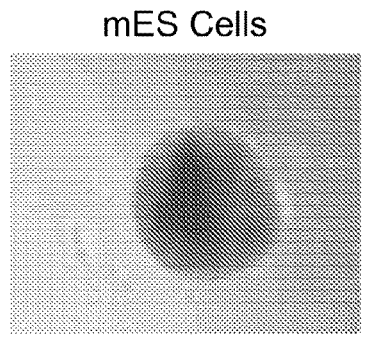
FIG. 14. ΔNp63 deficient mouse and human epidermal cells form embryoid bodies. A-D) Embryoid bodies using mouse embryonic stem cells (WT ES cells) or epidermal cells of the indicated genotypes. Magnification 200×.
Figure 14B:
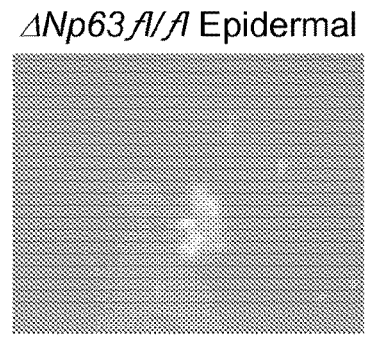
Figure 14C:
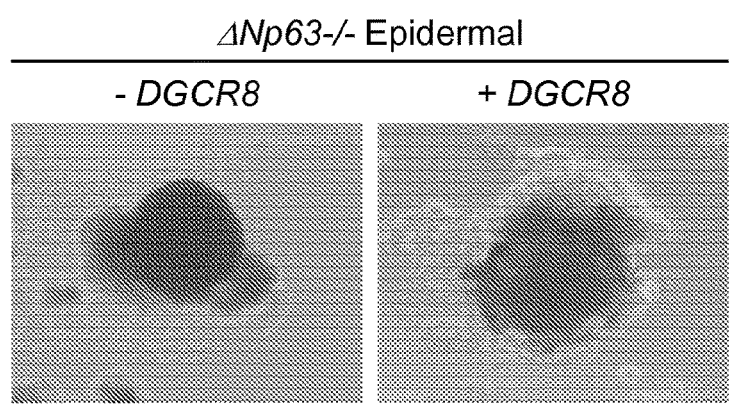
Figure 14D:
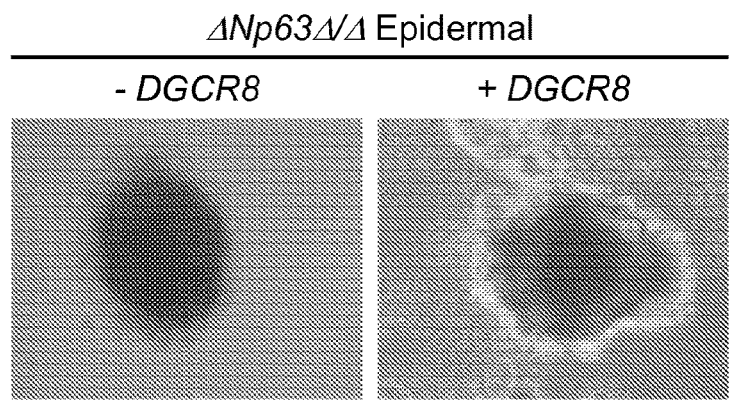

When the inventors cultured ΔNp63Δ/Δ epidermal cells expressing DGCR8 in neuroectodermal media, these cells displayed a neuronal morphology (FIG. 7C). Importantly, these cells expressed nestin and NeuN, markers of neuronal differentiation (FIG. 7E). Wild-type embryonic stem (ES) cells (ΔNp63fl/fl), wild-type epidermal cells (ΔNp63fl/fl), ΔNp63Δ/Δ epidermal cells, and ΔNp63−/− epidermal cells were cultured under conditions that induce the formation of embryoid bodies and the differentiation of multiple embryonic layers. Importantly, epidermal cells lacking ΔNp63 formed embryoid bodies (FIG. 14) and expressed markers of the mesoderm (MyoD), endoderm (AFP), and ectoderm (Neu N) (FIG. 8) when transduced with DGCR8 similar to wild-type ES cells (FIGS. 14A and 8A-C) while wild-type epidermal cells could not form embryoid bodies (FIG. 14B), further indicating that deletion of ΔNp63 in epidermal cells gives rise to cells that are pluripotent and can be differentiated into multiple cell fates in vitro. These results once again indicate that expression of DGCR8 is critical for the terminal differentiation of ΔNp63−/− epidermal cells and in its absence these cells express miRNAs that induce pluripotency and inhibit terminal differentiation.

Example 10

Figure 7F:
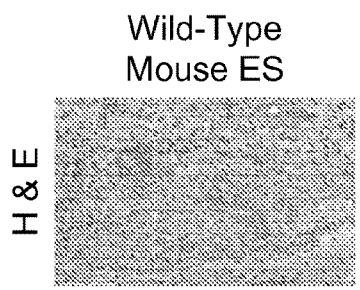
FIG. 7. ΔNp63 deficient epidermal cells are pluripotent. A-D) ΔNp63 deficient epidermal cells (Δ/Δ) with or without DGCR8 (pDGCR8) cultured under the following conditions: (A) keratinocyte media Low Ca2+, (B) keratinocyte differentiation media (High Ca2+), and (C) neuroectodermal media. D) Western blot analysis of epidermal cells cultured in keratinocyte differentiation media of the indicated genotypes with (+pDGCR8) or without (−pDGCR8) DGCR8 and using the antibodies shown. Actin was used as a loading control. E) qRT-PCR for nestin and NeuN using total RNA from epidermal cells of the indicated genotypes cultured in neuroectodermal media. F-H) Hematoxylin and eosin (H&E) stained cross sections of teratomas derived from wild-type mouse embryonic stem cells (F), ΔNp63−/− epidermal cells (G), and ΔNp63−/− epidermal cells expressing DGCR8. I-K) Immunohistochemistry (IHC) for DGCR8 (200× magnification) and insets (400× magnification). Arrows in insets point to examples of positive cells. Immunofluorescence (L-T) of teratomas derived from wild-type mouse embryonic stem cells (ES), ΔNp63−/− epidermal cells, and ΔNp63−/− epidermal cells expressing DGCR8 using the indicated antibodies. DAPI and hematoxylin were used as counterstains. Magnification 200×.
Figure 7G:
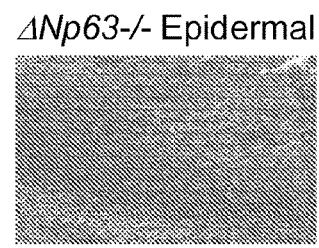
Figure 7H:
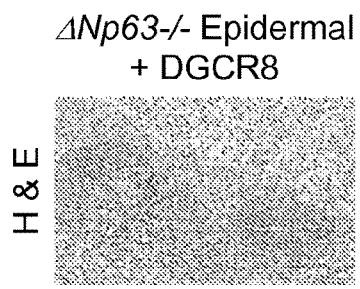
Figure 7I:
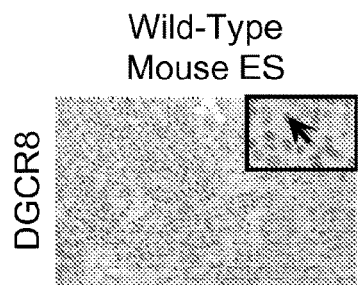
Figure 7J:
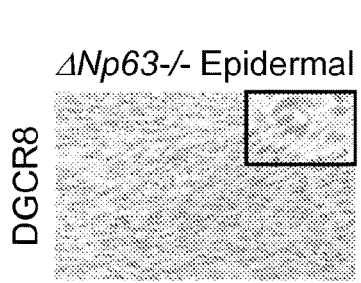
Figure 7K:
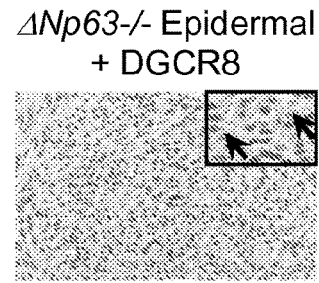
Figure 7L:
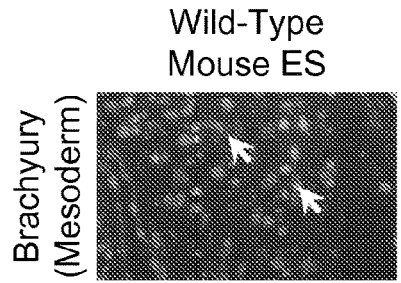
Figure 7M:
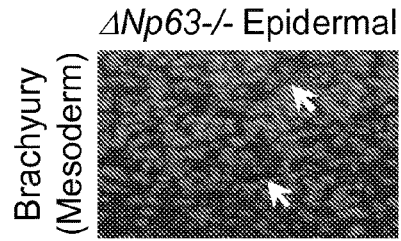
Figure 7N:
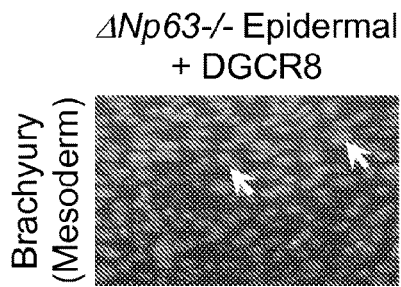
Figure 7O:
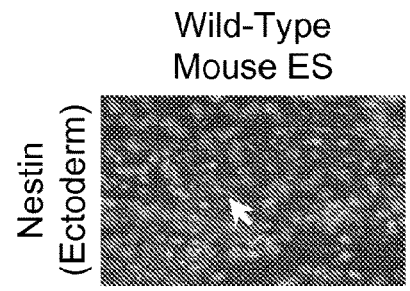
Figure 7P:
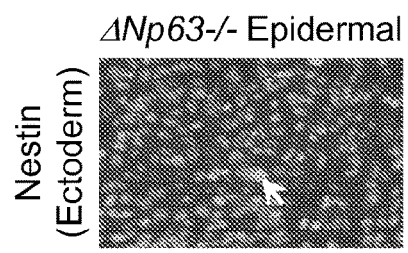
Figure 7Q:
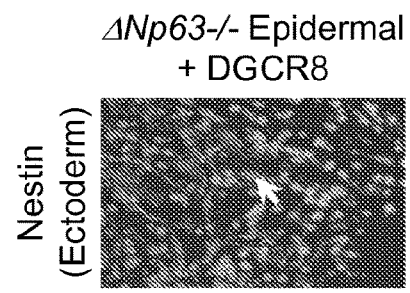
Figure 7R:
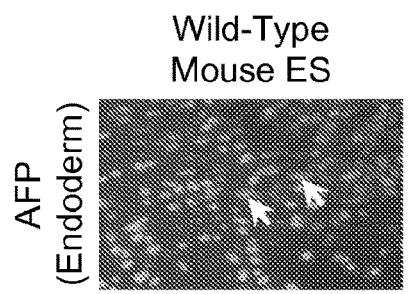
Figure 7S:
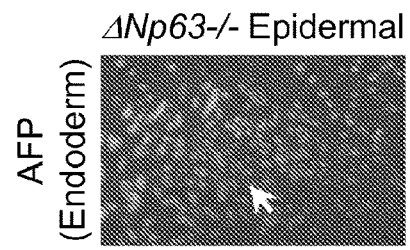
Figure 7T:
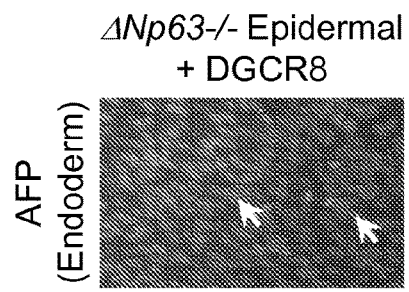
Figure 8A:
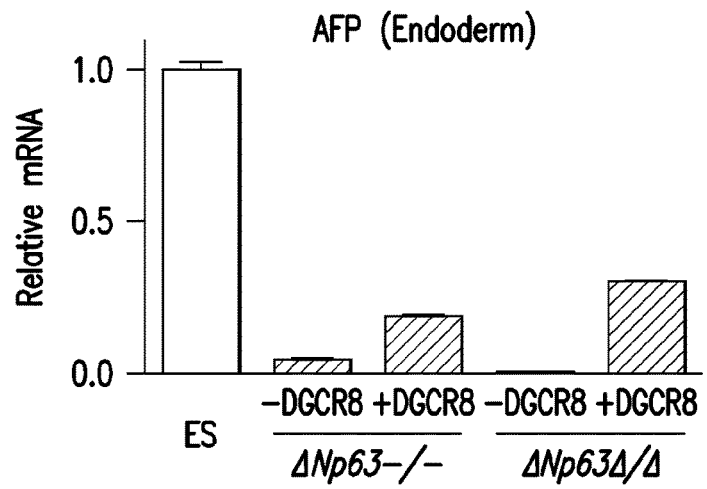
FIG. 8. ΔNp63 deficient epidermal cells are pluripotent. A-C) qRT-PCR for: AFP (A), MyoD (B), and NeuN (C) using total RNA from embryoid bodies shown in FIG. 14.
Figure 8B:
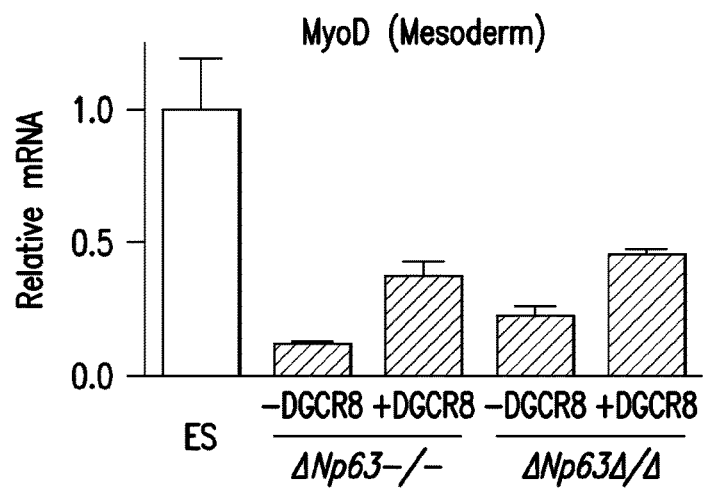
Figure 8C:
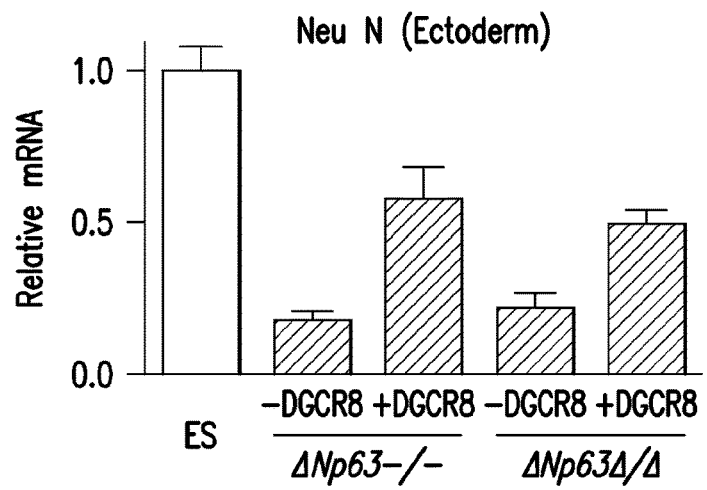
Figure 9:
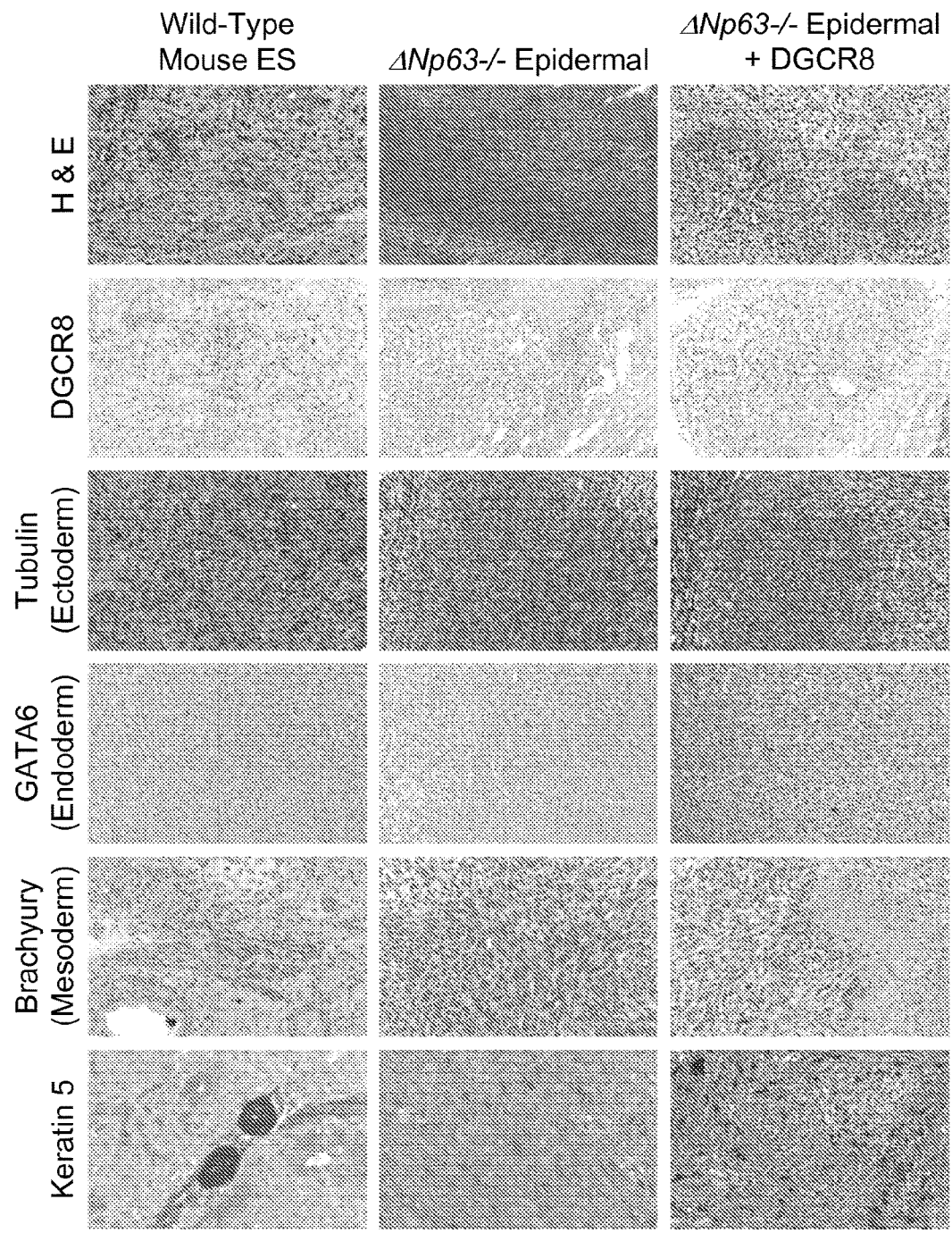
FIG. 9. ΔNp63 deficient epidermal cells expressing DGCR8 form teratomas. Hematoxylin and eosin stained and IHC stained cross sections of teratomas using mouse embryonic stem (ES) cells or epidermal cells of the indicated genotypes. Antibodies were used for DGCR8, markers of the three germ layers (tubulin, GATA6, and brachyury), and keratin 5. Magnification 200×.

ΔNp63 Deficient Epidermal Cells are Pluripotent and can Differentiate into Multiple Cell Fates In Vivo The data thus far indicates that epidermal cells lacking ΔNp63 have characteristics of induced pluripotent stem (iPS) cells. To further determine whether ΔNp63−/− epidermal cells are iPS cells, it was considered whether cells lacking ΔNp63 could form teratomas after injection into mice. Indeed, ΔNp63−/− epidermal cells can form poorly differentiated teratomas in mice and express markers of the ectoderm, mesoderm, and endoderm (FIGS. 9 and 7F-T). Moreover, these ΔNp63−/− teratomas express low levels of mesoderm-brachyury (FIG. 7M), ectoderm-nestin (FIG. 7P), AFP (FIG. 7S), and keratin 5 (FIG. 9). Because the terminal differentiation of ΔNp63−/− epidermal cells depends on the expression of DGCR8 (FIGS. 7A-E), ΔNp63−/− epidermal cells were transduced with a tetracycline inducible DGCR8 vector. These cells were injected into mice, were allowed to form tumors for four weeks, and fed doxycycline for two weeks. The ΔNp63−/− epidermal cells expressing DGCR8 form well-differentiated teratomas that express markers of the ectoderm (FIG. 7Q), mesoderm (FIG. 7N), and endoderm (FIGS. 7T and 9). These tumors also express clusters of K5 expressing cells. Expression and structures apparent in ΔNp63−/− epidermal cells expressing DGCR8 is similar to that of wild-type mES cells (FIGS. 7L, O, and R). The data indicate that ΔNp63−/− epidermal cells are iPS cells that can be reprogrammed into multiple cell fates, including keratinocytes. These data also demonstrate the requirement of DGCR8 in ΔNp63−/− epidermal cells for terminal differentiation.

Figure 11K:
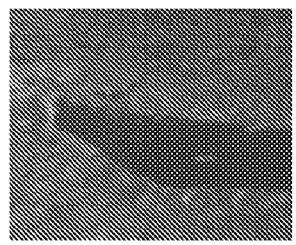
FIG. 11. Generation of chimeric mice from ΔNp63−/− epidermal cells. A-E) Bright field images of chimeric embryos at day 13.5 (E13.5) generated from mouse induced pluripotent stem cells expressing the Yamanaka factors and GFP (Yamanaka Factors) (A&B) or ΔNp63 deficient epidermal cells expressing GFP (ΔNp63−/−) (C&D). (E) E13.5 embryos from wild-type, non-chimeric mice. F-J) Fluorescent images of E13.5 chimeric embryos with GFP expressing tissues derived from the Yamanaka miPS cells (F&G) or ΔNp63−/− epidermal cells (H&I). J) E13.5 embryos from wild-type, non-chimeric mice. K-N) Immunofluorescence for GFP in the brain (K) and gut (L) of E13.5 embryos generated from Yamanaka miPS cells expressing GFP (Yamanaka Factors) or in the brain (M) and gut (N) of E13.5 embryos generated from ΔNp63−/− epidermal cells. DAPI was used as counterstain. Magnification 200×.
Figure 11L:
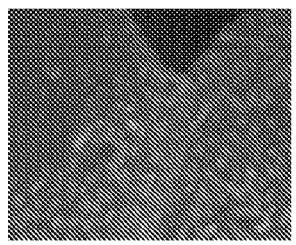
Figure 11M:
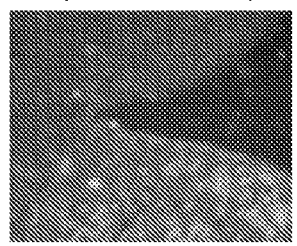
Figure 11N:
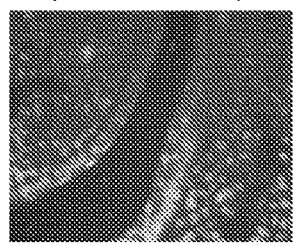

The inventors next asked whether ΔNp63−/− epidermal cells could contribute to tissues of the developing mouse. To determine this, blastocyst injections were performed using iPS$^{Yam}$ expressing GFP and ΔNp63−/− epidermal cells expressing GFP (Table 3). ΔNp63−/− epidermal cells expressing GFP form high contribution chimeras (FIGS. 11C, D, H, and I) comparable to what is seen with iPS cells created using the Yamanaka factors expressing GFP (FIGS. 11A, B, F, and G). Cross sections through multiple tissues of chimeras generated from both iPS cell types revealed similar chimeric contribution (FIGS. 11K-N). Chimeric mice were intercrossed with wild-type mice to determine whether the ΔNp63−/− epidermal cells contribute to the germline. The inventors examined 6 litters of chimeric mice born from these cells at P1 and find that they die shortly after birth due to skin defects and are cannibalized by their mothers similar to the ΔNp63−/− mice. The only mice that survived had a white coat color indicating that the ΔNp63−/− iPS cells had not contributed to tissues in these mice (Table 3).

TABLE 3

| A: Embryos generated from iPS cells | | | |
|---|---|---|---|
| iPS cells | # of blastocysts | # of embryos @ E13.5 | # of GFP +ve |
| ΔNp63−/− 1 | 17 | 4 | 2 |
| ΔNp63−/− 2 | 12 | 3 | 1 |
| ΔNp63−/− 3 | 14 | 0 | 0 |
| ΔNp63−/− 4 | 15 | 1 | 0 |
| ΔNp63−/− 5 | 15 | 4 | 2 |
| ΔNp63−/− 6 | 20 | 0 | 0 |
| ΔNp63−/− 7 | 21 | 0 | 0 |
| iPS$^{Yam}$-1 | 14 | 0 | 0 |
| iPS$^{Yam}$-2 | 12 | 2 | 1 |
| iPS$^{Yam}$-3 | 16 | 9 | 4 |
| iPS$^{Yam}$-4 | 16 | 9 | 3 |
| iPS$^{Yam}$-5 | 21 | 6 | 2 |
| iPS$^{Yam}$-6 | 21 | 7 | 3 |

| B: Mice generated from iPS cells | | | |
|---|---|---|---|
| iPS cells | # of blastocysts | # of pups @ P1 | # of pups @ P7 | coat color |
| ΔNp63−/− 1 | 17 | 2 | 0 | N/A |
| ΔNp63−/− 2 | 13 | 3 | 0 | N/A |
| ΔNp63−/− 3 | 14 | 0 | 0 | N/A |
| ΔNp63−/− 4 | 16 | 3 | 3 | White |
| ΔNp63−/− 5 | 17 | 2 | 0 | N/A |
| ΔNp63−/− 6 | 21 | 0 | 0 | N/A |

ΔNp63−/−: epidermal cells derived from ΔNp63−/− mice
iPS$^{Yam}$: mouse fibroblasts reprogrammed with the Yamanaka factors

Example 11

Normal Human Epidermal Keratinocytes can be Induced to Pluripotency by Knockdown of ΔNp63 or DGCR8

Figure 15K:
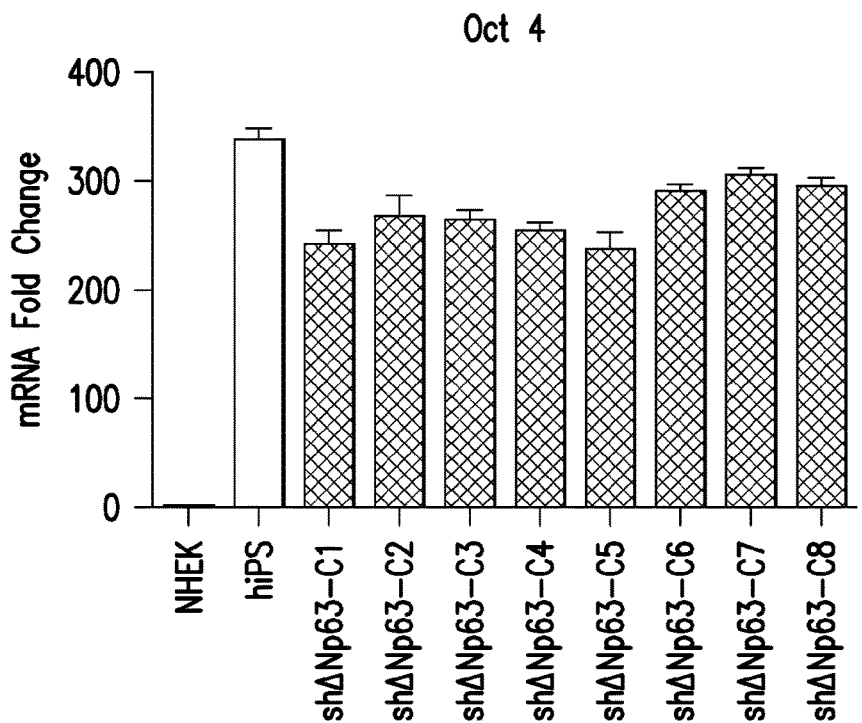
FIG. 15. Analysis of NHEK-shΔNp63 and NHEK-sh-DGCR8 iPS cells. A&B) Western blot analysis using the indicated antibodies of lysates from ΔNp63−/− epidermal cells, NHEKs (un) and NHEKs transduced with lentiviruses expressing the indicated shRNAs (shΔNp63 or shDGCR8) or a scrambled shRNA (scr). Actin was used as a loading control. C-F) Micrographs of normal human epidermal keratinocytes (NHEKs) cultured in keratinocyte media (C) or ES media (D) or NHEKs with lentiviruses expressing shΔNp63 (E) or shDGCR8 (F) cultured in ES media. G&H) Micrographs of embryoid bodies generated from NHEKs with lentiviruses expressing shΔNp63 (G) or shDGCR8 (H). Arrows indicate embryoid bodies (200× magnification). Embryoid bodies of each genotype are further magnified in the inset in the lower right corner (400× magnification). I-J) Western blot analysis of lysates from eight clones (#1-#8) of NHEKs transduced with lentiviruses expressing shΔNp63 (I) or shDGCR8 (J) at passage 10 using the indicated antibodies. Lysates from uninfected NHEKs were used as controls and actin was used as a loading control. K-P) qRT PCR for Oct4 (K&N), Sox2 (L&O), and Nanog (M&P) using total RNA from eight clones (#1-#8) of NHEKs transduced with lentiviruses expressing shΔNp63 (K-M) or shDGCR8 (N-P) at passage 10.
Figure 15L:
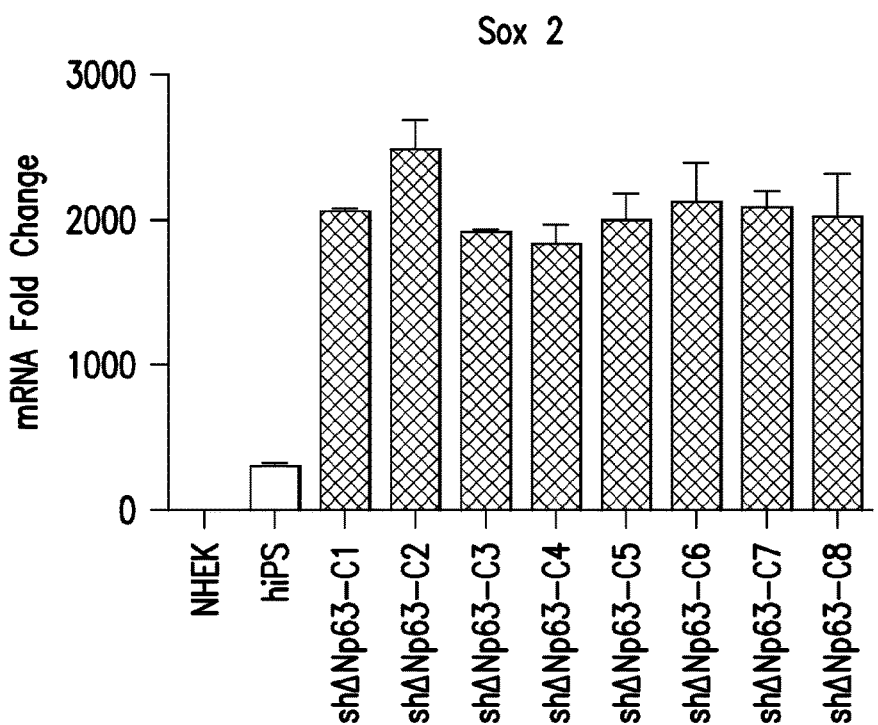
Figure 15M:
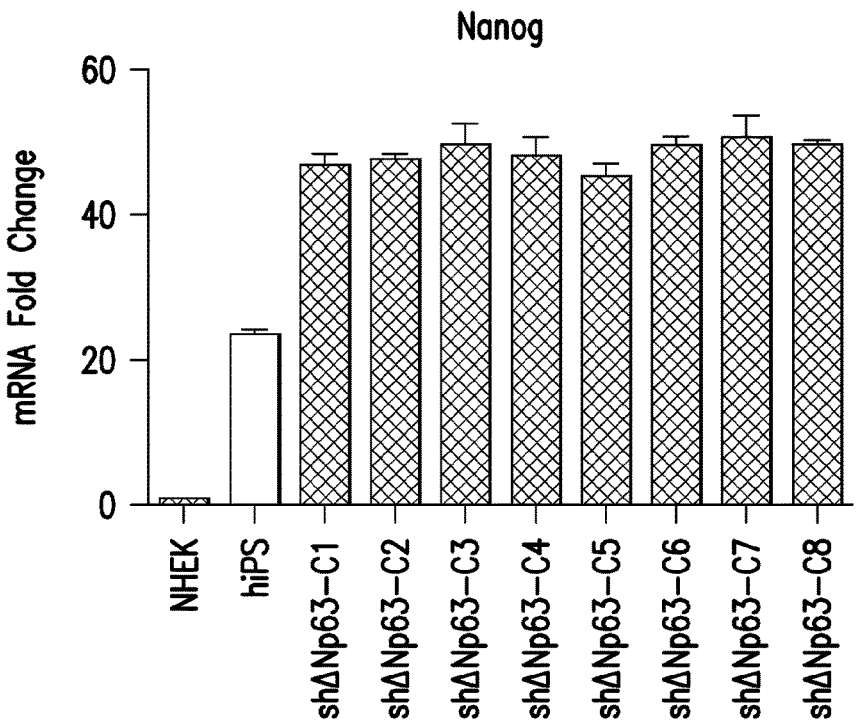
Figure 15N:
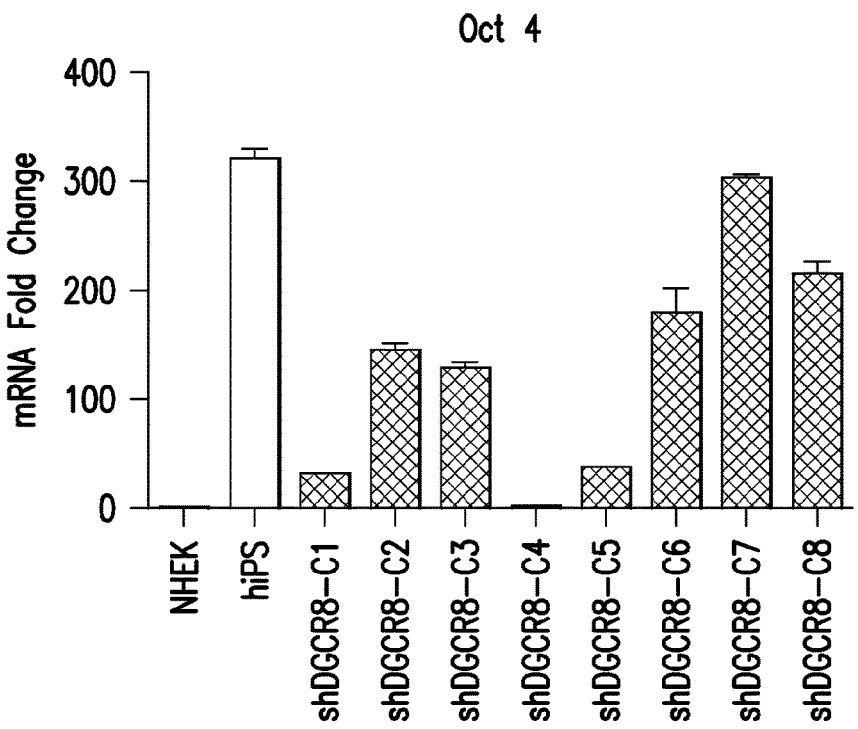
Figure 15O:
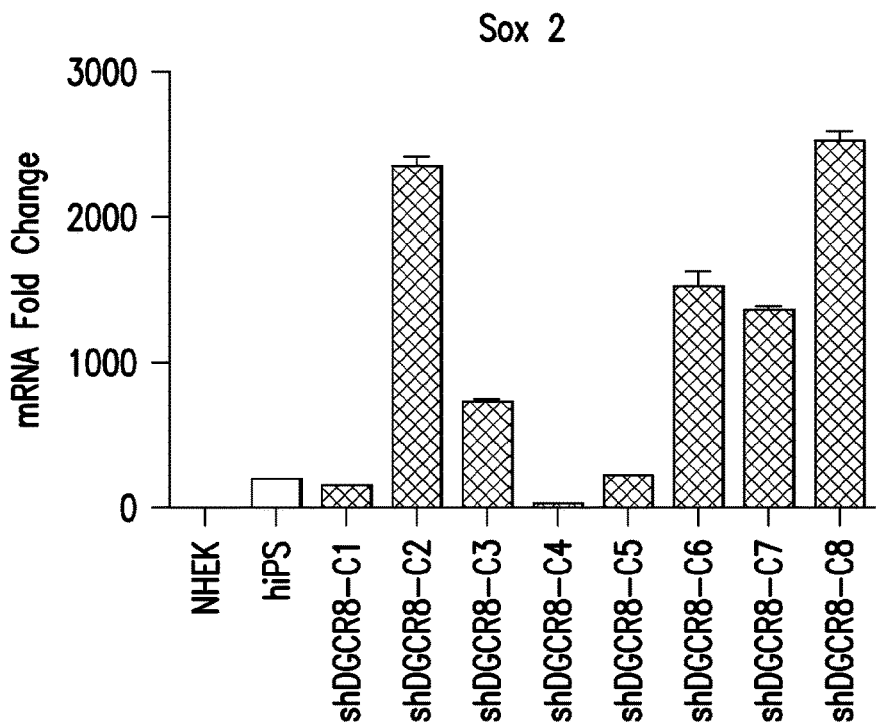
Figure 15P:
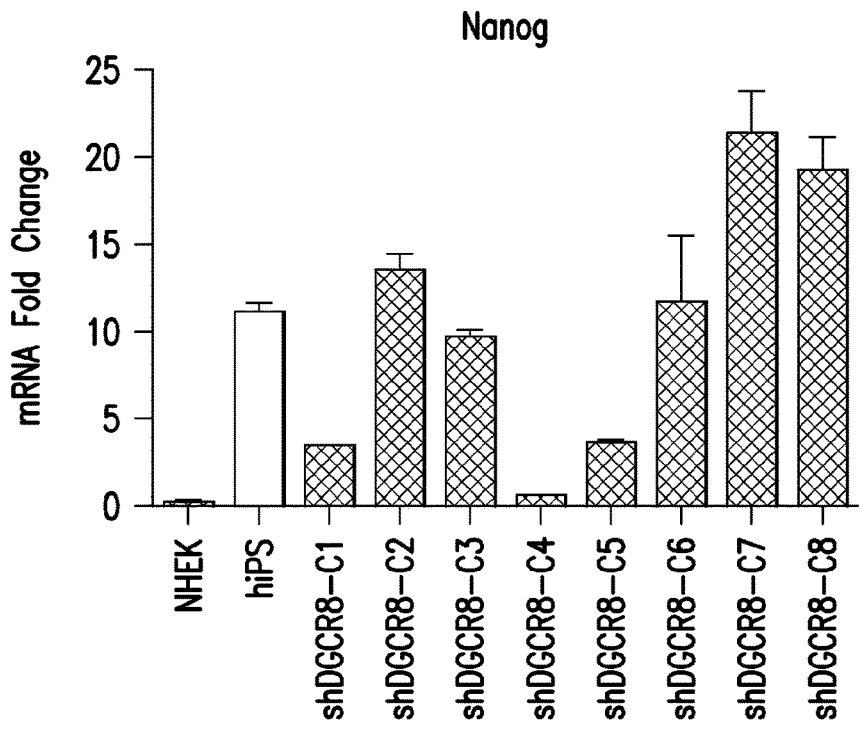
Figure 16C:
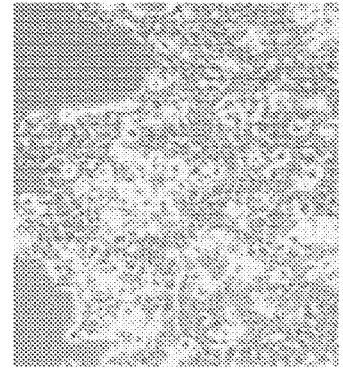
FIG. 16. Human NHEKs can be induced to pluripotency and form embryoid bodies expressing markers of all three embryonic germ layers. A-F) Micrographs of NHEKs transduced with lentiviruses expressing the indicated shRNAs and cultured in keratinocyte media (A-C) or ES cell media with LIF (D-F). Magnification 200×. G&H) Micrographs of embryoid bodies cultured in ES cell media without LIF using NHEKs transduced with lentiviruses expressing the indicated shRNAs. Arrows indicate embryoid bodies (200× magnification). Embryoid bodies of each genotype are further magnified in the inset in the lower right corner (400× magnification). I-K) qRT-PCR for genes expressed in the three germ layers of the embryo: AFP (endoderm) (I), brachyury (mesoderm) (J), and nestin (ectoderm) (K). qRT PCR values are normalized to GAPDH.
Figure 16F:
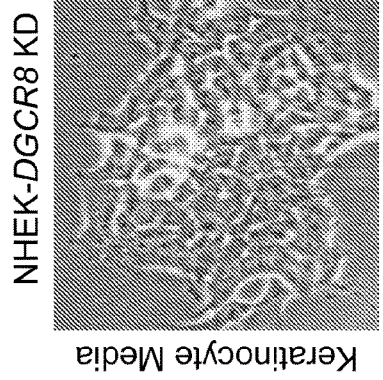
Figure 16B:
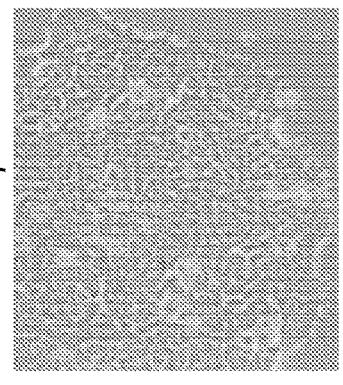
Figure 16E:
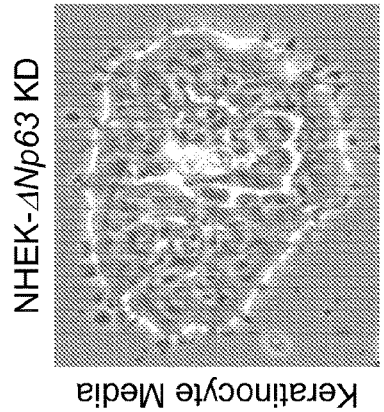
Figure 16A:
Figure 16D:
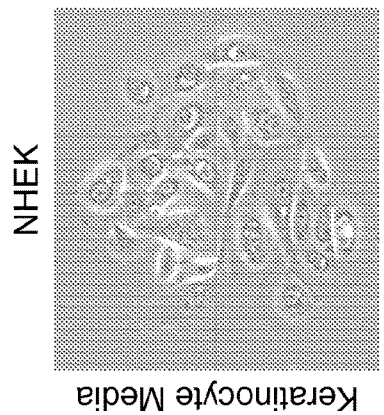
Figure 16G:
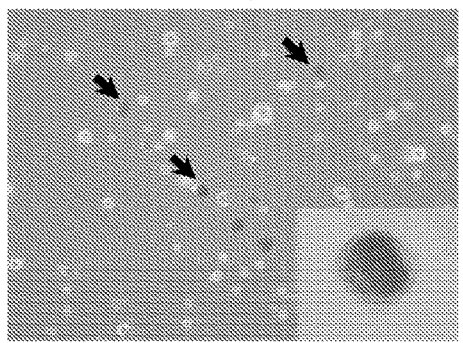
Figure 16H:
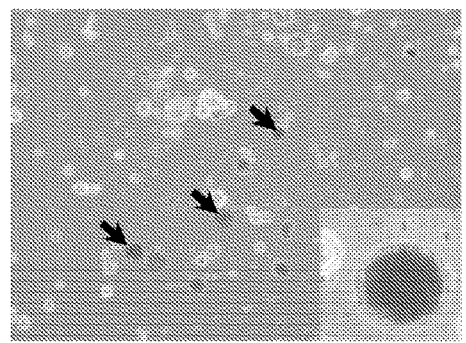
Figure 16I:
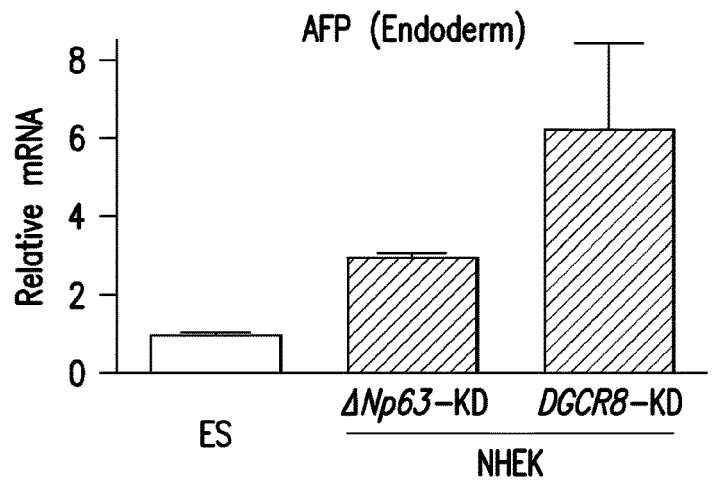
Figure 16J:
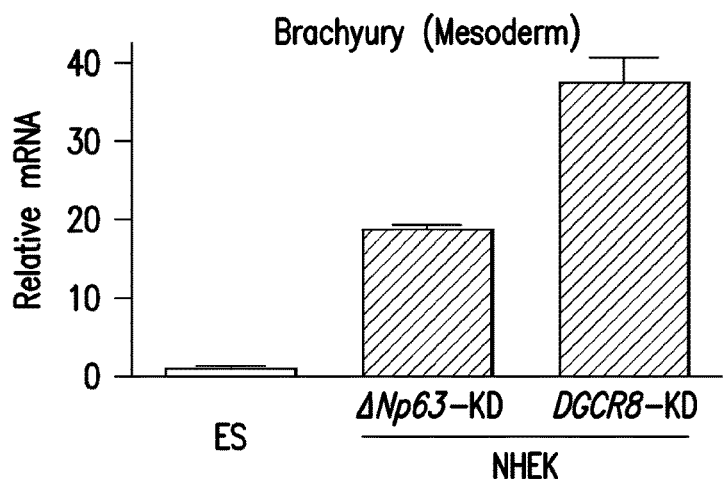
Figure 16K:
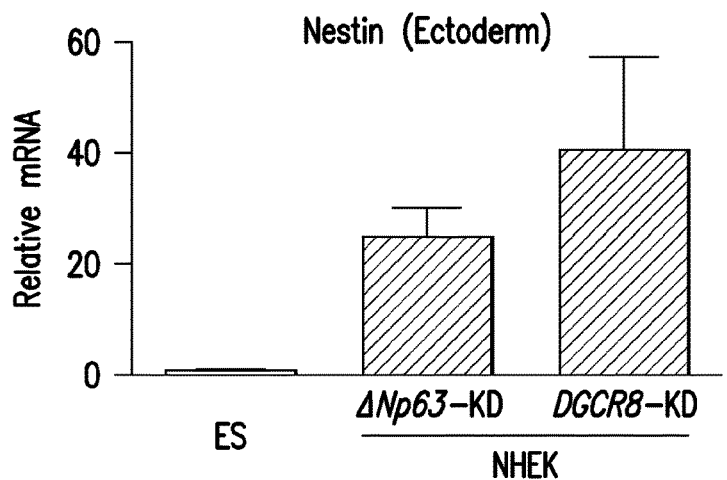

To determine whether knockdown of ΔNp63 or DGCR8 could induce pluripotency in human epidermal keratinocytes ΔNp63 or DGCR8 were knocked down in normal human epidermal keratinocytes (NHEKs) (FIGS. 15A and B). NHEKs with either knock down of ΔNp63 or DGCR8 changed morphology in keratinocyte media. Colonies from NHEKs with knock down of ΔNp63 or DGCR8 appeared more packed than colonies formed from NHEKs (compare FIGS. 16B and C to FIG. 16A and compare FIGS. 15C-F). This phenotype was further exacerbated in ES cell media with LIF. NHEKs appeared differentiated and senescent (FIG. 16D) while colonies formed from NHEKs with knock down of ΔNp63 or DGCR8 appeared packed and have a similar morphology to ES cell colonies (FIGS. 16E and F). NHEKs with knock down of ΔNp63 or DGCR8 also expressed Oct4 and Sox2 at high levels (FIG. 16G). It was next considered whether these cells could form embryoid bodies and differentiate into the three germ layers of the embryo. Indeed, these cells efficiently formed embryoid bodies (FIGS. 16G and H) comparable to those formed by wild-type ES cells (FIG. 14A) and expressed genes from the endoderm, mesoderm, and ectoderm (FIGS. 16I-K). The expression was comparable or higher than the expression of embryoid bodies formed from ES cells (FIGS. 16I-K).

Figure 12A:
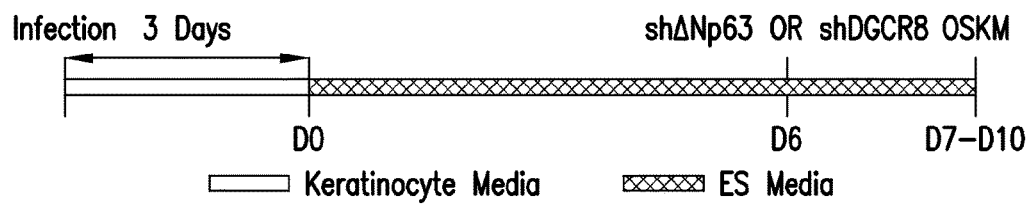
FIG. 12. Normal human epidermal keratinocytes (NHEKs) deficient for ΔNp63 or DGCR8 are pluripotent and form teratomas. A) Graphical representation of the number of days (D) required to reprogram NHEKs with shΔNp63 or shDGCR8 (6 days—D6) or the Yamanaka factors (Oct4, Sox2, Klf4, and c-myc) (7-10 days, D7-10). B-P) Immunofluorescence (IF) using normal human epidermal keratinocytes (NHEK) infected with lentiviral shRNA for ΔNp63 (NHEK-shΔNp63) (B-F) or DGCR8 (NHEK-shDGCR8) (G-K) and fibroblasts infected with the Yamanaka Factors (Human iPS) (L-P) and the indicated antibodies. DAPI was used as counterstain. Arrows indicate examples of positive nuclei. Magnification 200×. Q-U) Micrographs of hematoxylin and eosin stained cross-sections from teratomas generated using NHEK-shΔNp63 cells indicating the structural diversity of the three different germ layers as indicated. Magnification 100×. V-C') IF performed on cross-sections of teratomas derived from NHEK-shΔNp63 cells (V-Y) or human iPS cells (Z-C') using the indicated antibodies. DAPI was used as counterstain. Magnification 200×. D') Heat map for microRNA-Seq showing the mouse to human comparison performed using cells of the following genotypes: mouse embryonic stem cells (mES), mouse iPS cells generated from fibroblasts using the Yamanaka factors (miPSYam), wild-type mouse keratinocytes ((m)Keratinocytes 1, 2, 3, 4), normal human epidermal keratinocytes transduced with shΔNp63 or shDGCR8 ((h) NHEKshΔNp63 or (h)NHEKshDGCR8), human iPS cells generated from fibroblasts using the Yamanaka factors (hiPSYam), and (h)NHEK cells. Low miRNA expression is indicated in green and high expression in red. mES, miPSYam, (m)ΔNp63−/− epidermal cells, (h)NHEKshΔNp63, (h)NHEKshDGCR8, and hiPSYam cells clustered together while wild-type mouse keratinocytes ((m)Keratinocytes 1, 2, 3, 4) and normal human epidermal keratinocytes (NHEKs) clustered together.

Six days subsequent to knock down of ΔNp63 or DGCR8 (FIG. 12A) in NHEKs, markers of pluripotency (Nanog, Tra-1-60, and Oct4) could be detected (FIGS. 12B-K). NHEKs transduced with the Yamanaka factors (Oct4, Sox2, Klf4, and c-myc) expressed markers of pluripotency between days 7 and 10 (FIG. 12A). The inventors next examined the efficiency of reprogramming of NHEKs with knock down of ΔNp63 or DGCR8 compared to NHEKs transduced with Oct4, Sox2, Klf4, and c-myc and found that NHEKs depleted of ΔNp63 or DGCR8 had a reprogramming efficiency of 0.07% and 0.1%, respectively, compared to 0.03% for NHEKs expressing Oct4, Sox2, Klf4, and c-myc (Table 4). The inventors next asked whether these cells could form embryoid bodies and differentiate into the three germ layers of the embryo. Indeed, these cells efficiently formed embryoid bodies (FIGS. 15G and H) comparable to those formed by wild-type ES cells. Importantly, multiple NHEK clones stably transduced with shΔNp63 or shDGCR8 retained silencing of ΔNp63 (FIG. 15I) or DGCR8 (FIG. 15J) and expression of Oct4, Sox2, and Nanog at equal or higher levels to human iPS (hiPS) cells (FIGS. 15K-P). NHEKs with knock down of ΔNp63 (FIGS. 12B-F) or DGCR8 (FIGS. 12G-K) also expressed SSEA-4, Tra-1-60, Oct4, Sox2, and Nanog similar to the expression in hiPS cells (FIGS. 12L-P) while NHEKs alone do not express these markers of pluripotency. The inventors next asked whether these cells could form teratomas in SCID mice. Indeed, these cells form differentiated teratomas with structures representing the endoderm (FIG. 12Q), mesoderm (FIGS. 12R-T), and ectoderm (FIG. 12U). Additional immunofluorescence for marker analysis revealed robust expression of AFP, MF 20, E-cadherin, and keratin 5 (FIGS. 12V-Y) comparable to the expression in human iPS cells generated using the Yamanaka factors (FIGS. 12Z-C'). Taken together, these data indicate human keratinocytes can be reprogrammed to different cells fates by knock down of ΔNp63 or DGCR8 in a rapid (6 days) and efficient manner.

TABLE 4

Efficiency of reprogramming in normal human epidermal keratinocytes (NHEKs)

| Method of reprogramming in NHEKs | OKSM | shDGCR8 | shΔNp63 |
|---|---|---|---|
| % efficiency | 0.03 | 0.10 | 0.07 |

% efficiency represented as number of Tra-1-60 positive colonies divided by 1 × 10⁵ multiplied by 100. Number of positive colonies counted from duplicate plates for each method of reprogramming at day 14.

Figure 12D:
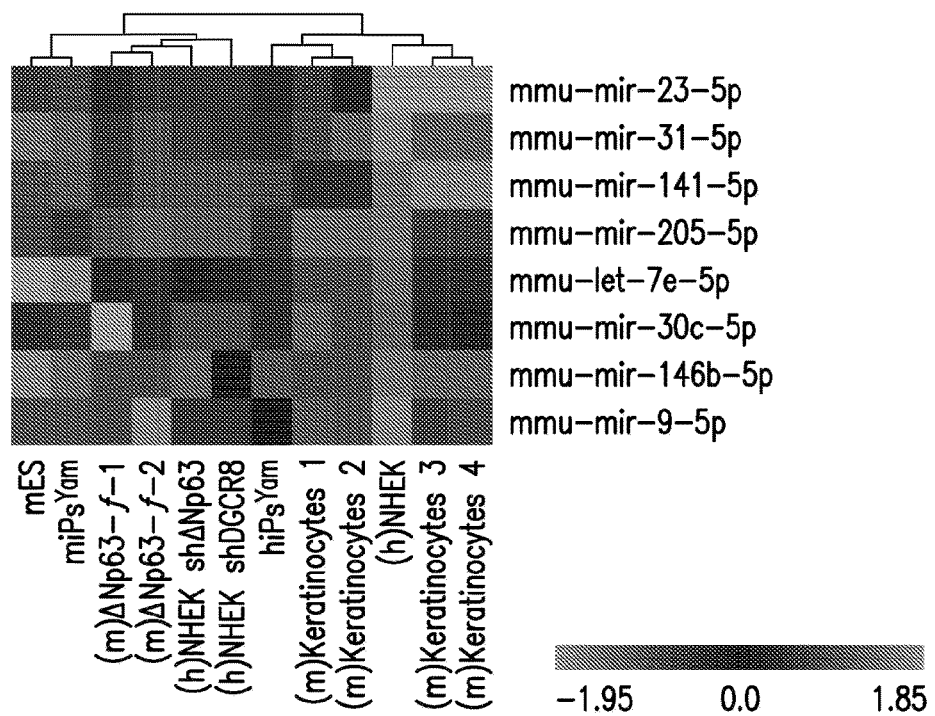

Lastly, the inventors performed miRNA-Seq and RNA-Seq using RNA isolated from NHEKs with knock down of ΔNp63 or DGCR8 (FIG. 12D'). Importantly, the seven most significantly differentially expressed miRNAs (miR-9-5, miR-23a, miR-146b, miR-200c/miR141, miR-31, miR-205, and miR-30b/c) in mouse ΔNp63−/− epidermal cells were also differentially expressed in human cells (NHEKs) with knock down of ΔNp63 or DGCR8 (FIG. 12D'). Moreover, both mouse and human cells deficient for ΔNp63 or DGCR8 expressed the same miRNA signature and clustered with mouse and human iPS cells (FIG. 12D'). This indicates that these miRNAs are conserved between human and mouse and are critical for induced pluripotency through the ΔNp63/DGCR8 pathway. Additionally, the gene expression signature of these human cells clustered with ΔNp63−/− epidermal cells, miPS$^{Yam}$, and mES cells derived from the mouse indicating that pluripotency can be induced by acute knock down of ΔNp63 or DGCR8 in human keratinocytes. Additionally, NHEKs with knock down of ΔNp63 or DGCR8 had a nearly identical gene expression signature, indicating that cells deficient for ΔNp63 regulate the same genes in differentiation and stem cell specification as DGCR8.

Figure 10:
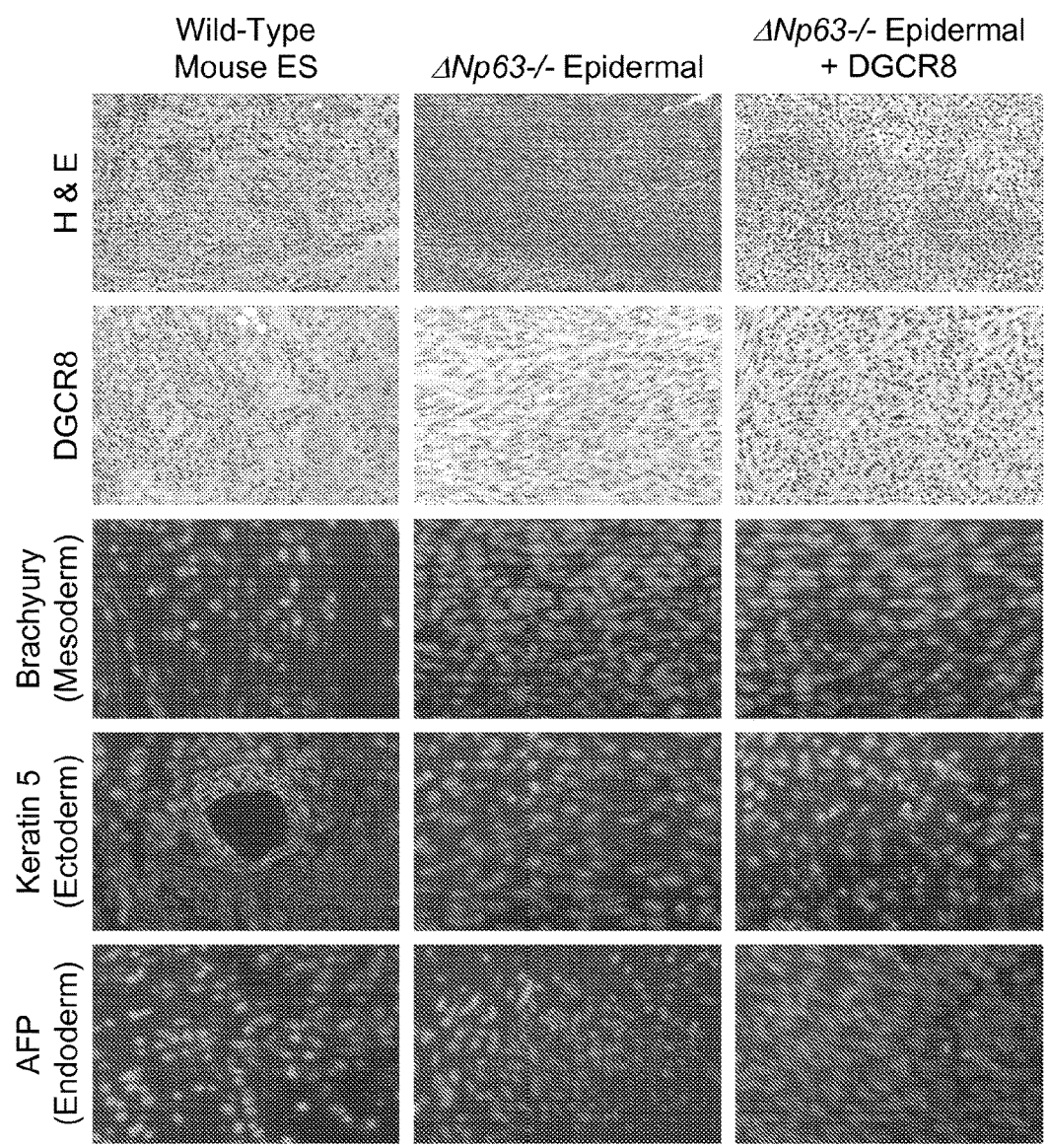
FIG. 10. ΔNp63 deficient mouse epidermal cells expressing DGCR8 form teratomas. Hematoxylin and eosin (H&E), immunohistochemistry (IHC), and immunofluorescence (IF) of cross sections from teratomas derived from mouse embryonic stem (ES) cells or epidermal cells of the indicated genotypes. Antibodies for DGCR8 and markers of the mesoderm, ectoderm, and endoderm are indicated on the left. Magnification 200×.

FIGS. 10 and 11 were generated using ΔNp63 deficient mouse epidermal cells. FIG. 10 shows that ΔNp63 deficient mouse epidermal cells (Flores iPS cells) can form teratomas and FIG. 11 shows that these cells can contribute to multiple lineages in the mouse (expressed with GFP (green) expression). These two assays are currently the gold standard to demonstrate that cells are pluripotent. These data indicate that ΔNp63 deficient epidermal cells are induced pluripotent stem cell (iPS) cells and indicate that knockdown of ΔNp63 in other cell types can induce pluripotency. Human keratinocytes can be induced to pluripotency, as shown in FIG. 16. These data are novel in that the deletion of one gene leads to pluripotency. These cells can therefore be used to generate multiple cell types and have important implications for regenerative medicine.

Example 12

Significance of Certain Embodiments of the Invention

Here, it is shown that deletion or knock down of ΔNp63 or DGCR8 in primary mouse and human epidermal keratinocytes, respectively, results in efficient reprogramming of cells to a state of pluripotency. Mice with a germline deletion of ΔNp63 have a rudimentary, disorganized epidermis that forms around the developing mouse embryo and fails to terminally differentiate. These epidermal phenotypes are reminiscent of mice lacking DGCR8 and Dicer expression in the skin (Yi et al., 2006; Yi et al., 2009). Accordingly, ΔNp63 deficiency resulted in low levels of DGCR8 and miRNAs that are critical repressors of the pluripotency factors, Oct4, Sox2, and Nanog (Tay et al., 2008; Xu et al., 2009). In the absence of ΔNp63 all three of these pluripotency factors were expressed at levels comparable to that found in mouse embryonic stem cells and that ΔNp63 transcriptionally regulates DGCR8. Additionally, ΔNp63−/− epidermal cells had a miRNA signature similar to that of ES cells and iPS cells (Houbaviy et al., 2003; Li et al., 2010; Lin et al., 2009a; Peter, 2009) and these cells can be differentiated into multiple cells fates both in vitro and in vivo. Importantly, acute deletion of ΔNp63 or DGCR8 in human keratinocytes resulted in reprogrammed cells that resemble ES cells and can be differentiated to express genes representative of the three embryonic germ layers. These data have important implications for regenerative medicine and provide evidence that epidermal cells, which are readily accessible through the skin, can be reprogrammed to a pluripotent state without the addition of oncogenes.

The presence of a rudimentary epidermis in ΔNp63−/− mouse embryos and the ability of ΔNp63 deficient epidermal cells to self-renew was quite surprising. The roles of p63 in epidermal morphogenesis have been the subject of heated controversy. Experimental evidence supports a role for p63 in both stem cell proliferation and in the initiation of differentiation (Koster et al., 2004; Mills et al., 1999; Senoo et al., 2007; Yang et al., 1999). Elegant experiments using p63 deficient epithelial cells demonstrated that p63 is required for stem cell proliferation (Senoo et al., 2007). Also, data from an equal number of studies using p63−/− mice showed that p63 is required for proper differentiation of epithelial tissues (Koster et al., 2004). Most of these studies were performed using mouse models that are deficient for all isoforms of p63 making the interpretation of the data difficult to decipher due to the existence of multiple p63 isoforms. More recently, experiments have been performed using in vivo siRNA knock down of ΔNp63α, the isoform predominantly expressed in the skin (Koster et al., 2007), or germline deletion of the ΔNp63 isoforms (ΔNp63$^{gfp/gfp}$) (Romano et al., 2012). Both mouse models are consistent with the inventors' data in that ΔNp63 is required for complete terminal differentiation. The inventors' mouse model has unveiled unknown functions of the ΔNp63 isoforms in epidermal stem cell proliferation and in the induction of epidermal differentiation. The inventors' ΔNp63 conditional knockout allele has allowed for germline and acute deletion in epidermal cells of ΔNp63. Importantly, ΔNp63 indirectly regulates the expression of the pluripotency factors Oct4, Sox2, Nanog, and a unique miRNA signature by direct transactivation of DGCR8. ΔNp63 is required for commitment to terminal differentiation through a unique miRNA and mRNA signature that is similar in both mouse and human cells. In line with the inventors' observations, recent evidence indicates that factors other than Oct4, Sox2, and Nanog are critical for appropriate reprogramming of differentiated cells to pluripotency (Buganim et al., 2012).

The data also show that expression of DGCR8 can bypass the terminal differentiation defects in ΔNp63 deficient epidermal cells and allows reprogramming into multiple cell fates. The phenotype of ΔNp63+/− and ΔNp63−/− embryos is similar to that of mice with DGCR8 ablated in K14 expressing cells within the epidermis. All three of these mouse models have a hyperproliferative epidermis (Yi et al., 2006; Yi et al., 2009). Moreover, DGCR8−/− embryonic stem cells continue to self-renew and fail to undergo terminal differentiation. This is similar to what was found in mouse epidermal cells that were derived from ΔNp63 germline deleted mice as well as those with acutely deleted ΔNp63. These cells continued to self-renew in clonogenic assays while wild-type epidermal cells senesced and also continued to express markers of pluripotency, Oct4, Sox2, and Nanog, after multiple passages. The inventors were able to terminally differentiate ΔNp63−/− epidermal cells after re-expression of DGCR8. Although it has been suggested that ΔNp63 induces pluripotency (Senoo et al., 2007), the present data supports an embodiment whereby deletion of ΔNp63 induces pluripotency in epidermal stem cells and likely in other progenitor cells where ΔNp63 is normally expressed. The inventors further demonstrated the induction of pluripotency in normal human keratinocytes that were acutely knocked down for ΔNp63 or DGCR8. Thus, knock down of either one of these two factors, ΔNp63 or DGCR8, represents a new way to induce keratinocytes to pluripotency without the expression of proto-oncogenes or deletion of tumor suppressor genes. Importantly, loss of ΔNp63 does not result in loss of p53 expression, which has been shown previously to result in efficient reprogramming (Andl et al., 2006; Anokye-Danso et al., 2011; Buganim et al., 2012; Hong et al., 2009; Kawamura et al., 2009). This result is significant given that down regulation of tumor suppressor genes, like p53, while leading to the generation of cells that are pluripotent, can also lead to the production of tumorigenic cells (Li et al., 2009).

The miRNA expression patterns of ΔNp63−/− epidermal cells were similar to that of embryonic stem cells and induced pluripotent stem cells. Consistent with low levels of DGCR8 in ΔNp63−/− epidermal cells, miR-203, miR-205, and the miR-200 family (miR-200a, miR-200b, miR-200c, miR-141, miR-145, miR-429) were expressed at very low levels. Paradoxically, there were a large number of miRNAs that were upregulated. These included miR-290, miR-295, miR-302, miR-106b, miR-125b, miR-134, miR-296, miR-93, miR-17, miR-130a, miR-22, and miR-34a, which have been found upregulated in both embryonic stem cells and/or induced pluripotent stem cells (Houbaviy et al., 2003; Li et al., 2010; Lin et al., 2009a; Peter, 2009). The high levels of some miRNA expression may be due to the fact that there is still a low level of DGCR8 expression present in ΔNp63−/− epidermal cells. Thus, in certain embodiments of the invention, low DGCR8 leads to low expression of critical miRNAs for reprogramming of ΔNp63−/− epidermal cells that in turn leads to upregulation of miRNAs that are characteristic of pluripotency. These high expressing miRNAs may be processed via DGCR8 independent mechanisms (Chong et al., 2010). Re-expression of DGCR8 in ΔNp63−/− epidermal cells rescued expression of these miRNAs. Another striking finding was that the miRNA expression of ΔNp63−/− epidermal cells clustered with mouse iPS cells generated with the Yamanaka factors (miPS$^{Yam}$) and mES cells while ΔNp63−/− epidermal cells expressing DGCR8 clustered with wild-type keratinocytes. Importantly, the miRNA and gene expression patterns between both mouse and human epidermal cells deficient for ΔNp63 clustered together and with human and mouse iPS and mouse ES cells, further indicating that ΔNp63 is a key player in reprogramming cells to pluripotency.

The methylation of gene promoters in iPS cells reprogrammed using multiple methods have been shown to retain the pattern or "memory" of somatic cells (Marion et al., 2009). Remarkably, methylation patterns of gene promoters involved in stem cell specification and differentiation were more similar between the ΔNp63−/− epidermal cells and mouse embryonic stem cells, indicating that the inventors' method of reprogramming through knock down of ΔNp63 results in a more faithful reprogramming to stem cells than methods that have been used previously.

In summary, ΔNp63 is required for transcriptional activation of DGCR8 in epidermal stem cells. DGCR8 is essential for epidermal morphogenesis; therefore, in the absence of ΔNp63, the epidermal stem cells in the developing skin fail to suppress expression of Oct4, Sox2, and Nanog and therefore fail to terminally differentiate. These cells are pluripotent and can be differentiated into multiple lineages. These findings have important implications for regenerative medicine. Based on the results herein using human keratinocytes, in certain aspects of the invention epidermal cells can be extracted from patient skin biopsies and reprogrammed into pluripotent stem cells by knock down of ΔNp63 or DGCR8. Indeed, inducible knock down of ΔNp63 and/or DGCR8 may be preferable to the overexpression of potentially oncogenic factors such as myc or the down regulation of the critical tumor suppressor gene, p53. In the future, understanding the mechanisms employed by the individual p63 isoforms in maintaining progenitor and stem cells in various tissues is key to understanding its complex roles in stem cell maintenance as well as cancer development and metastasis.

Example 13

Experimental Procedures

Generation of ΔNp63 Conditional Knockout Mice.

The cre-loxP strategy was used to generate the ΔNp63 conditional knockout allele (ΔNp63fl). Genomic p63 DNA from intron 3 to intron 3' was amplified from BAC clone DNA (BAC RP23-186N8, Children's Hospital Oakland Research Institute). LoxP sites flanking exon 3' of p63 and neomycin (neo) gene flanked by frt sites inserted in intron 3' were cloned into pL253 (Liu et al., 2003). Mouse embryonic stem cells (ESCs) were analyzed by Southern blot analysis for proper targeting of the ΔNp63 allele. Chimeras resulting from ESC clones injected into C57BL/6 blastocysts were mated with C57BL/6 albino females and genotyped as described below. Mice with germ line transmission of the targeted allele (conditional, flox neo allele, fn) were crossed to the FLPeR mice to delete the neo cassette (Farley et al., 2000). Resulting progeny were intercrossed with Zp3-Cre (C57BL/6) (Lewandoski et al., 1997) transgenic mice. ΔNp63fl/+; Zp3-Cre females were mated with C57BL/6 males to generate ΔNp63+/− mice. The ΔNp63+/− mice were intercrossed to generate ΔNp63−/− mice. All procedures were approved by the IACUC at U.T. M.D. Anderson Cancer Center.

Genotyping.

Genomic DNA from tail biopsies was genotyped by Southern blot analysis by digesting genomic DNA with BglI or by PCR to using the following primers and annealing temperatures: 1) for wild-type: wt-F, 5'-ACAGTCCTCT-GCTTTCAGC-3' (SEQ ID NO:1) and wt-R (fl-R), 5'-CA-CACAGCA CTGGCCTTGC-3' (SEQ ID NO:2), annealing temp: 62° C., 2) for ΔNp63flox: fl-F, 5'-TTAGGTGGA TCCCTAGGAAGAG-3' (SEQ ID NO:3) and fl-R (wt-R), 5'-CACACAGCACTGGCCTTGC-3' (SEQ ID NO:4), annealing temp: 62° C., and 3) for ΔNp63KO: ko-F, 5'-TA-CAGCTCCTGGAGGATC CCATGC-3' (SEQ ID NO:5) and wt-R, annealing temp: 62° C. Primers used to genotype for the CRE gene are as follows: Cre-F, 5'-TGGGCG-GCATGGTGCAAGTT-3' (SEQ ID NO:6) and Cre-R, 5'-CGGTGCTAACCAGCGTTTTC-3' (SEQ ID NO:7), annealing temp: 60° C. The PCR products were electrophoresed on a 1% agarose gel.

Histology and Immunostaining of E18.5 Embryos.

Pregnant females at day 18.5 of gestation were injected three times at 1 hour intervals with BrdU (100 mg/gram of total body weight). Embryos were extracted 1 hour later and fixed in 10% formalin at room temperature for 18 hours. Fixed embryos were embedded in paraffin, sectioned, and stained with hematoxylin and eosin (H&E) for microscopic analysis. For immunofluorescence (IF), paraffin-embedded sections were rehydrated in xylene and decreasing concentrations of ethanol. Sections were subjected to antigen unmasking in citrate buffer unmasking solution (Vector Laboratory) followed by incubation with blocking solution, and 18 hour incubation at 4° C. with the following primary antibodies: K5 (1:1000) (Abcam), K14 (1:500) (LifeSpan BioSciences), K10 (1:1000) (Covance), K1 (1:500) (gift from Dennis Roop), K18 (1:200) (Sigma), and filaggrin (1:1000) (Abcam). Visualization was performed using an anti-rabbit secondary antibody conjugated to Texas-red (1:5000) (Jackson ImmunoResearch Laboratories), an anti-guinea pig secondary antibody conjugated to FITC (1:1000, Jackson ImmunoResearch Laboratories), or an anti-chicken secondary antibody conjugated to Alexa 488 (1:1000) (Molecular Probes) followed by counterstaining with DAPI (Vector Laboratory). Incorporation of BrdU was analyzed using the BrdU detection kit II (Roche). For BrdU analysis by IF, an anti-rabbit secondary antibody conjugated to Texas Red was used with the BrdU detection kit II (Roche). For immunohistochemistry (IHC), paraffin-embedded sections were prepared as described above and incubated with K8 primary antibody (1:80) (University of Iowa). Visualization was performed using the Vectastain Elite ABC and DAB Peroxidase Substrate Kits (Vector Laboratory).

Mouse Epidermal Cell and Keratinocyte Culture.

Wild type, Np63$^{-/-}$, ΔNp63' keratinocytes were isolated from E18.5 day embryos as described previously (Su et al., 2009a; Su et al., 2009b). Cells were plated on J2-3T3m feeder cells and cultured in F media (Sigma) supplemented with 0.4 mg/ml hydrocortisone, 24 ng/ml adenine, 8.4 ng/ml cholera toxin, 5 mg/ml insulin, 13 ng/ml 3,3,5-triiodo-L-thyronine, and 10 ng/ml EGF as described earlier (Barrandon and Green, 1987; Su et al., 2009a; Su et al., 2009b).

Chromatin Immunoprecipitation.

Wild type and ΔNp63−/− keratinocytes were grown to near confluence on J2-3T3m feeder cells in F media as described previously (Su et al., 2009a; Su et al., 2009b). Feeder cells were removed with 0.02% EDTA 24 hours prior to collecting keratinocytes for chromatin extraction. Cellular proteins were crosslinked to DNA using 1% formaldehyde and chromatin was prepared as described earlier (Flores et al., 2002; Su et al., 2009a; Su et al., 2009b). p63 ChIP analysis was performed using a pan-p63 antibody (4A4, Abcam) as described previously. Each ChIP was performed in triplicate using keratinocytes from three embryos of each genotype. Q-RT-PCR was performed by using primers specific for the indicated regions of the DGCR8 promoter: Site (−3393)—forward 5'-AGTCACCTTGGTGCC TCT-CATAG-3' (SEQ ID NO:8) and (−3348)—reverse 5'-AAACAGGTGGCAAGGCTTCTT-3' (SEQ ID NO:9), Site2 (−1459)—forward 5'-CATTTTTTTCTGTG-GATCTTTTGGT-3' (SEQ ID NO:10) and (−1397)—reverse 5'-CACAGGGCAGGC AGATCAG-3' (SEQ ID NO: 11), and nonspecific site (−3893)—forward 5'-CAAAT-CAAAATCTGCATCCATAGG-3' (SEQ ID NO:12) and (−3833)—reverse 5'-GCCCTCCTGCCTGTAAACCT-3' (SEQ ID NO:13).

Western Blot Analysis.

Total cell lysates were generated from keratinocytes or skin from E18.5 day embryos. 50 μg of protein were electrophoresed on a 10% SDS PAGE and transferred to PVDF membrane as described previously (Su et al., 2009a;

Su et al., 2009b). Blots were probed with anti-ΔNp63 (1:1000) (BioLegend), K5 (1:1000) (Abcam), K10 (1:1000) (Covance), filaggrin (1:1000) (Abcam), DGCR8 (1:200) (Abcam), Oct4 (1:1000) (Santa Cruz), or Sox2 (1:500) (Santa Cruz) at 4° C. for 18 hours followed by incubation for one hour at room temperature with the appropriate secondary antibodies conjugated to horseradish peroxidase (1:5000) (Jackson Lab). Actin (Sigma 1:5000) was used as a loading control. Detection was performed using the ECL Plus Kit (Amersham) following the manufacturer's protocol and x-ray autoradiography.

RNA Extraction and Quantitative Real Time PCR.

Total RNA was prepared from mouse embryos or keratinocytes using the RNeasy plus kit (Qiagen). cDNA was synthesized from 2 μg of total RNA using the SuperScript® III First-Strand Synthesis Kit (Invitrogen) according to the manufacturer's protocol followed by q-RT PCR using the Power SYBR Green PCR Master mix (AB Applied Biosystems). Primers for qRT-PCR were used as described previously: DGCR8 (Han et al., 2009), Oct4, Sox2, Nanog (Taube et al., 2010), Nestin (Pattyn et al., 2003), NeuN (Hu et al., 2010), and ΔNp63, TAp63 and GAPDH (Su et al., 2009a; Su et al., 2009b).

Cloning of dgcr8-Luciferase Reporter Genes.

To generate the dgcr8 S luciferase construct, DNA was amplified from wild type mouse genomic DNA (C57BL/6) using primers containing the p63 binding site shown by ChIP and 5' XhoI and 3' BglII cloning restriction enzyme sites: 1. forward—DGCR8-Luc F: XhoI 5'-CCGCTCGAG-GCTTCTAGTTGTCTATTCC-3' (SEQ ID NO:14) nand 2. reverse—DGCR8-Luc R: BglII 5'-GGA AGATCTGCT-CACCAGATAGCTTGGA-3' (SEQ ID NO:15). PCR amplicons were digested with XhoI and BglII and ligated into pGL3 basic luciferase reporter vector (Promega). The QuickChange® Multi Site-Directed Mutagenesis kit was used to generate dgcr8 Sm using the dgcr8 S luciferase construct as a template and the following primers: 1. 5'-AT-GCCTGTCTAAAGTCACTTTTGTGCCTCTCATAGGC-CTG-3' (SEQ ID NO:16), 2. 5'-GCATGTATCTC-CTAAGAAGCTTTTCCACCTGTTTACAACACCAG-3' (SEQ ID NO: 17), and 3. 5'-TGGTGCCTCTCATAGGCCT-GTTTTTATCTCCTAAGAAGCCTTGC-3' (SEQ ID NO:18).

Dual-Luciferase Reporter Assay.

Luciferase reporter assays were performed as described previously (Lin et al., 2009b; Su et al., 2010). Briefly, p53−/−;p63−/− MEFs (Flores et al., 2002) were plated on 6-well plates ($3.5 \times 10^5$ cells per well). Twelve hours after plating, the MEFs were transiently transfected using Fugene HD (Roche) with 1 μg of dgcr8 S or dgcr8 Sm, 0.5 μg of Renilla luciferase plasmid (transfection control), and 0.5 μg plasmids encoding the p63 isoforms [TAp63α, TAp63β, TAp63γ, ΔNp63α, ΔNp63β, or ΔNp63γ or 0.5 g of empty vector (pcDNA3)]. After 24 hr, cells were harvested and luciferase activity was measured using the Dual-Luciferase Reporter Assay system (Promega) and a Veritas microplate luminometer (Turner BioSystems). Each experiment was performed in triplicate.

Adeno-Cre Infection.

Passage-0 ΔNp63fl/fl keratinocytes were plated at a density of $1 \times 10^6$ in 10 cm dish on J2-3T3 feeder cells. When cell reached 80% confluency, cells were infected with adenovirus-Cre-GFP (5000 particles per cell) to generate ΔNp63Δ/Δ cells. Adenovirus-GFP (Vector Development Lab, Baylor College of Medicine) was used as a control. The efficiency of infection was calculated to be 100% by GFP expression. Western analysis was performed for ΔNp63 to score for efficient deletion of ΔNp63 after infection.

Differentiation Culture: Keratinocytes and Neurons.

Twenty-four hours after adenoviral infection, ΔNp63fl/fl and ΔNp63Δ/Δ cells were trypsinized. and plated at a density of $1 \times 10^6$ in a 10 cm dish on J2-3T3 feeder cells in F media supplemented with high calcium at a final concentration of (1.6 mM) for 3 days. Keratinocyte differentiation was assessed using western blot analysis for K5, K10 and filaggrin as described above. ΔNp63fl/fl and ΔNp63Δ/Δ cells were also cultured in neuroectodermal media (Grinnell et al., 2007). Neuronal differentiation was assessed by qRT-PCR for Nestin and NeuN as described above.

Keratinocyte Cells—Proliferation Assay.

$1 \times 10^3$ ΔNp63fl/fl and ΔNp63Δ/Δ epidermal cells were plated on mitomycin c (Roche)-treated J2 3T3 feeder cells in F media as described (Barrandon and Green, 1987; Senoo et al., 2007; Su et al., 2009a; Su et al., 2009b). Colonies cultured for 7 days were trypsinized, counted, and plated at limiting dilution 10 cells, 100 cells, and 1000 cells per 6 cm dish. At each passage, dishes were fixed in 10% formalin for 30 min and stained with 2% rhodamine B (Sigma). Some dishes were treated with 10 mM BrdU, fixed in 70% ethanol for 30 minutes, denatured with 0.01N NaOH, and double immunostained with anti-cytokeratin 5 (Abcam) (1:1000) and BrdUFITC conjugated antibody (GeneTex, Inc.). To detect and visualize cytokeratin 5 staining, Texas Red-conjugated goat anti-rabbit secondary antibodies were used (Jackson ImmunoResearch) (1:500).

Keratinocyte Colony Formation.

$4 \times 10^5$ ΔNp63fl/fl and ΔNp63Δ/Δ epidermal cells were plated on mitomycin c (Roche)-treated J2 3T3 feeder cells in F media as described (Barrandon and Green, 1987; Su et al., 2009a; Su et al., 2009b). Colonies cultured for 7 days were trypsinized for the next passage. At each passage, some dishes were fixed in 10% formalin for 30 min and stained with 2% rhodamine B (Sigma). Some dishes were treated with 10 mM BrdU, fixed in 70% ethanol for 30 minutes, denatured with 0.01N NaOH, and double immunostained with anti-cytokeratin 5 (Abcam) (1:1000) and BrdU-FITC conjugated antibody (GeneTex, Inc.). To detect and visualize cytokeratin 5 staining, Texas Red-conjugated goat anti-rabbit secondary antibodies were used (Jackson ImmunoResearch) (1:500)

Normal Human Epidermal Keratinocytes (NHEK) Culture and Infection.

NHEKs (Lonza) were cultured in serum free media containing supplements according to the manufacture's protocol (Lonza). NHEKs were infected with pGIPZ lentiviral vectors with shRNAs for human p63 and DGCR8 (Open Biosystems). Cells were selected for 48 hours with puromycin (2 μg/ml). Selected cells were subsequently used for the generation of embryoid bodies.

Cell Culture.

Wild type, $ΔNp63_{-/-}$, $ΔNp63_{fl/fl}$ keratinocytes were isolated from E18.5 day embryos as described previously (Su et al., 2009a; Su et al., 2009b). Cells were plated on J2-3T3m feeder cells and cultured in F media (Sigma) supplemented with 0.4 mg/ml hydrocortisone, 24 ng/ml adenine, 8.4 ng/ml cholera toxin, 5 mg/ml insulin, 13 ng/ml 3,3,5-triiodo-L-thyronine, and 10 ng/ml EGF as described earlier (Barrandon and Green, 1987; Su et al., 2009a; Su et al., 2009b). Mouse ES cells or $iPS^{Yam}$ (S3) cells (gift from Dr. Austin Cooney, Baylor College of Medicine) (Ross et al., 2010) were cultured on mitomycin treated feeder cells in the presence of ES cell media containing Knockout™ D-MEM (Invitrogen), 20% ESC screened FBS (Hyclone), 200 mM Lglutamine (Gibco), 100 g/ml penicillin/streptomycin (Gibco), 0.1 mM β-mercaptoethanol (Sigma) and 10 ng/ml recombinant mouse Leukemia inhibitory Factor (LIF, Gibco). Human iPS$_{Yam}$ cells (a gift from Dr. Brian Davis, MD Anderson Cancer Center) were maintained on hESC qualified Matrigel (BD Biosciences) following manufacturer's protocol in mTeSR1 (Stemcell Technologies) media.

Immunofluorescence—Cell Culture.

Mouse iPS$_{Yam}$, mouse ES, and ΔNp63−/− epidermal cells were cultured in 24 well dish on feeder cells. These cells were fixed in 4% paraformaldehyde for 30 minutes and incubated with the following antibodies: SSEA-1 (1:200 Developmental Studies Hybridoma Bank), Oct4 (1:100 Santa Cruz), Nanog (1:100 Abcam) for 18 hours at 4° C. Visualization was performed using an anti-mouse secondary antibody conjugated to Texas-red (1:5000) (Jackson ImmunoResearch Laboratories), or an anti-rabbit secondary antibody conjugated to FITC (1:1000, Jackson ImmunoResearch Laboratories) for one hour, followed by counterstaining with DAPI (Vector Laboratory). Human iPS cells were fixed in 4% paraformaldehyde for 30 minutes at room temperature and incubated with SEEA-4 (1:200 Developmental Studies Hybridoma Bank), Tra-1-60 (1:200 Millipore), Oct4 (1:100 Santa Cruz), Sox2 (1:100 Santa Cruz), Nanog (1:100 Abcam) for 18 hours at 4° C. Secondary antibodies were used as mentioned above and DAPI was used for visualization. Cells were rinsed in PBS and photomicrographs were taken with a Zeiss AxioObserver A1 inverted fluorescence microscope.

Promoter Methylation Assay. Promoter methylation analysis was performed according to the manufacturer's protocol with the Epitect Methyl qPCR Array (Qiagen). DNA was isolated from mouse ES cells, iPS$_{Yam}$ cells, ΔNp63−/− epidermal cells and wild-type keratinocytes. 1 µg DNA from each cell type was digested with methyl-sensitive or methyl-dependent enzymes individually or together according to the manufacturer's instructions. Digested DNA was loaded onto the qPCR array plates with specific probes for CpG islands on various promoters of stem cell specific or differentiation specific genes. The PCR data was normalized using the company's software to generate a heat map.

Embryoid Body Generation. Embryoid bodies were cultured using the hanging drop method. Each drop of 30 µL of ES cell media without LIF contained 800 cells. Hanging drops were incubated for 48 hours at 37° C. Hanging drops were aggregated (20 drops per well) in a six well low attachment plate and maintained for 7 days at 37° C. Total RNA was isolated from these cultures and analyzed using quantitative real time RT-PCR for Nestin and NeuN (ectodermal genes), brachyury and MyoD (mesodermal genes), and AFP endodermal gene.

miR-SEQ. Two micrograms of total RNA was isolated from wild-type (ΔNp63fl/fl) mouse keratinocytes, ΔNp63−/− epidermal cells and ΔNp63−/− epidermal cells expressing DGCR8 and purified using the miRvana microRNA isolation kit (Ambion) in preparation for miR-SEQ.

Small RNA Sequencing and Analysis. For small RNA library construction, RNA samples were prepared using the DGE-Small RNA Sample Prep Kit (Illumina, San Diego, Calif.) as described previously (Creighton et al., 2010; Creighton et al., 2009). A total of two Solexa-ready small RNA templates were analyzed on an Illumina GA-IIx Genome Analyzer at University of Houston. Cluster generation was performed and clusters were sequenced. Initial sequence process and analysis was followed as described previously (Creighton et al., 2010; Creighton et al., 2009). Small RNA-Seq sequencing data was uploaded and processed using the Genboree Small RNA Toolset (http://genboree.org). The Illumina adapter was trimmed, and reads with length between 11 and 36, a copy number of at least 4, and finishing in monomers with length less than 10, were selected for further processing, similar to the processing described (Creighton et al., 2010; Creighton et al., 2009). The reads were mapped to the mouse genome and build UCSC mm9 (NCBI 37) using Pash (Coarfa et al., 2010). Reads mapping up to 100 locations were selected for further analysis. The miRNA definitions from miRBase (Griffiths-Jones, 2004; Griffiths-Jones et al., 2006; Griffiths-Jones et al., 2008; Kozomara and Griffiths-Jones, 2010) were used to construct a known miRNA profile for each sample; the abundance of the known miRNAs were normalized as a fraction of the usable reads. A combined profile of all samples was computed, and each miRNA was normalized to its corresponding z-score within the distribution of its normalized abundance across all samples under consideration. Heatmaps were generated using the R statistical analysis system.

RNA Sequencing and Analysis. Approximately 5 µg of polyA+RNA was used to construct RNA-Seq libraries using the standard Illumina protocol. Mouse and human mRNA sequencing yielded 30-40 million read pairs for each sample. The mouse mRNA-Seq reads were mapped using TopHat (Trapnell et al 2010) onto the mouse genome and build UCSC mm9 (NCBI 37) and the RefSeq mouse genes. The human mRNA-Seq reads were mapped using TopHat onto the human genome and build UCSC hg19 (NCBI 37) and the RefSeq human genes. Gene expression and gene expression differences were computed using Cufflinks (Trapnell et al 2012, Roberts et al 2011, Trapnell et al 2010). Heatmaps and hierarchical clustering were produced using the R statistical analysis system.

Generation of an Inducible DGCR8 Lentiviral Vector.

A tetracycline inducible DGCR8 lentiviral vector was generated by cloning a PCR amplified product from pFLAG/HA-DGCR8 (Landthaler et al., 2004). Primers used to amplify the DGCR8 cDNA were as follows:

```
                                        (SEQ ID NO: 19)
    FOR-       GGATCCCATGGAGACAGATGAGAGC (SEQ ID NO: 20)
    REV-       GAATTCGGTGCACAGGGGCTCAC
```

The resulting PCR product was cloned into the EcoRI sites in the pLVX-Tight-Puro vector (Clontech).

Teratoma Formation Assay. ΔNp63−/− epidermal cells were infected with the tet-inducible DGCR8 vector and the pTet-On Advanced vector (Clontech) as described previously (Su et al., 2010). Severe combined immunodeficiency disease (SCID) mice were injected subcutaneously in the dorsal flank with a wild-type mouse ES cells or ΔNp63−/− epidermal cells transduced with the tet-inducible DGCR8 vector as described previously (Takahashi and Yamanaka, 2006). Mice were administered 2 mg/mL doxycycline in the drinking water to induce expression of DGCR8 3 weeks post injection after palpable tumors had formed. Another group of mice were administered water without doxycycline as controls for the same amount of time. Tumors were harvested 6 weeks after injection and fixed in 10% formalin. Paraffin embedded cross-sections were analyzed by hematoxylin and eosin staining and IHC using antibodies for DGCR8 (1:250, Abcam), tubulin (1:400 Sigma), GATA6 (1:200, Santa Cruz), brachyury (1:50, Santa Cruz), and K5 (1:1000, Abcam). For immunofluorescence (IF), paraffin-embedded sections were rehydrated in xylene and decreasing concentrations of ethanol. Sections were subjected to antigen unmasking in citrate buffer unmasking solution (Vector Laboratory) followed by incubation with blocking solution, and 18 hour incubation at 4° C. with the following primary antibodies: Nestin (1:50 Millipore), AFP (1:100 Santa Cruz), Brachyury (1:50 Santa Cruz). Visualization was performed using an anti-mouse secondary antibody conjugated to Texas-red (1:5000) (Jackson ImmunoResearch Laboratories), an anti-rabbit secondary antibody conjugated to FITC (1:1000, Jackson ImmunoResearch Laboratories) or an anti-goat secondary antibody conjugated to Texasred (1:1000, R&D Systems) for one hour, followed by counterstaining and mounting in Vectashield with DAPI (Vector Laboratory). Teratomas from normal human epidermal keratinocytes (NHEK) transduced with shΔNp63 cells were performed by Applied StemCell, Inc. NHEK-shΔNp63 and NHEK-shDGCR8 cells were grown on feeders in ES cells media. $1 \times 10^6$ cells were injected into the testes or the kidney capsule of SCID mice. Tumors were then fixed in 10% formalin, embedded in paraffin, cross-sectioned, and analyzed by H&E. Immunofluorescence was performed on paraffin embedded sections following rehydration and antigen retrieval (Vector Laboratories) as mentioned earlier. The slides were blocked for an hour in blocking solution (Vector Laboratories) and incubated for 18 hours at 4° C. with the following primary antibodies:AFP (1:100, Santa Cruz), brachyury (1:50, Santa Cruz), K5, (1:200, Abcam), E-cadherin, (1:100, Abcam). Visualization was performed by the help of anti-mouse Texas red or FITC (1:1000, Vector Laboratories), anti-rabbit Texas red or FITC (1:5000, Vector Laboratories) and anti-goat Texas red antibody (1:1000, R&D Systems). Counterstaining and mounting was performed with the help of Vectashield with DAPI (Vector Laboratory).

Small RNA Sequencing and Analysis. For small RNA library construction, RNA samples were prepared using the DGE-Small RNA Sample Prep Kit (Illumina, San Diego, Calif.) as described previously (Creighton et al., 2010; Creighton et al., 2009). A total of two Solexa-ready small RNA templates were analyzed on an Illumina GA-2 Genome Analyzer at University of Houston. Cluster generation was performed and clusters were sequenced. Initial sequence process and analysis was followed as described previously (Creighton et al., 2010; Creighton et al., 2009). Small RNA-Seq sequencing data was uploaded and processed using the Genboree Small RNA Toolset (http://genboree.org). The Illumina adapter was trimmed, and reads with length between 11 and 36, a copy number of at least 4, and finishing in monomers with length less than 10, were selected for further processing, similar to the processing described (Creighton et al., 2010; Creighton et al., 2009). The reads were mapped to the mouse genome and built UCSC mm9 (NCBI 37) using Pash (Coarfa et al., 2010). Reads mapping up to 100 locations were selected for further analysis. The miRNA definitions from miRBase (Griffiths-Jones, 2004; Griffiths-Jones et al., 2006; Griffiths-Jones et al., 2008; Kozomara and Griffiths-Jones, 2010) were used to construct a known miRNA profile for each sample; the abundance of the known miRNAs were normalized as a fraction of the usable reads. A combined profile of all samples was computed, and each miRNA was normalized to its corresponding z-score within the distribution of its normalized abundance across all samples under consideration. Heatmaps were generated using the R statistical analysis system.

Generation and Analysis of Chimeric Mice. ΔNp63−/− cells (12-18) expressing pLenti-GFP (Vector Development Laboratory, Baylor College of Medicine) or iPS$_{Yam}$ (S3) cells (12-18) expressing eGFP (Ross et al., 2010) were injected into albino B6 blastocysts and implanted in CD-1 pseudopregnant mice. Embryos at E18.5 were analyzed for GFP expression using a Zeiss SteREO Lumar, V12 microscope, with fluorescent and bright field capability. Non-chimeric E18.5 embryos were used as controls. The embryos were fixed in 10% formalin, embedded in paraffin, and immunofluorescence was performed on cross-sections using an anti-GFP antibody, 1:200 (Abcam). Visualization was done with the help of anti-rabbit FITC (1:1000, Jackson ImmunoResearch Laboratories) and counterstained and mounted with Vectashield with DAPI (Vector Laboratories). Chimeric mice that were carried to term were mated and assayed for germline transmission of deleted ΔNp63 allele using PCR as described above.

Calculation of Timing and Efficiency of Reprogramming. $1 \times 10^5$ normal human epidermal keratinocytes (NHEK) were plated on 6 cm dishes coated with 0.1% gelatin and infected for 48 hours with the following lentiviruses: shTRP63-pGIPz (Open BioSystems), shDGCR8-pGIPz (Open BioSystems), or OKSIM (Addgene) (Ross et al., 2010). On day 3, ES cell media was added to the cells. The cells were fixed with 4% paraformaldehyde on day 6, 8, and 14 to determine the timing of reprogramming by immunofluorescence staining with Oct-4 (Santa Cruz; 1:100), Tra-1-60 (Millipore; 1:200) or Nanog (1:100; Abcam) antibodies. DAPI (Vector Laboratory) was used as counterstain. To determine percentage of reprogramming efficiency the cells were fixed at days 8 and 14 and visualized by immunofluorescence using the antibodies listed above. Photonmicrographs were taken with a Zeiss AxioObserver A1 inverted fluorescence microscope at 10× magnification. Percent efficiency was calculated by counting Tra-1-60 positive colonies, dividing by $1 \times 10_5$ cells, and multiplying by 100.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Andl, T., Murchison, E. P., Liu, F., Zhang, Y., Yunta-Gonzalez, M., Tobias, J. W., Andl, C. D., Seykora, J. T., Hannon, G. J., and Millar, S. E. (2006). The miRNA-processing enzyme dicer is essential for the morphogenesis and maintenance of hair follicles. Curr Biol 16, 1041-1049.

Anokye-Danso, F., Trivedi, C. M., Juhr, D., Gupta, M., Cui, Z., Tian, Y., Zhang, Y., Yang, W., Gruber, P. J., Epstein, J. A., et al. (2011). Highly efficient miRNA-mediated reprogramming of mouse and human somatic cells to pluripotency. Cell Stem Cell 8, 376-388.

Barrandon, Y., and Green, H. (1987). Three clonal types of keratinocyte with different capacities for multiplication. Proc Natl Acad Sci USA 84, 2302-2306.

Buganim, Y., Faddah, D. A., Cheng, A. W., Itskovich, E., Markoulaki, S., Ganz, K., Klemm, S. L., van Oudenaarden, A., and Jaenisch, R. (2012). Single-Cell Expression Analyses during Cellular Reprogramming Reveal an Early Stochastic and a Late Hierarchic Phase. Cell 150, 1209-1222.

Carroll, D. K., Brugge, J. S., and Attardi, L. D. (2007). p63, cell adhesion and survival. Cell Cycle 6, 255-261.

Cho, M. S., Chan, I. L., and Flores, E. R. (2010). DeltaNp63 transcriptionally regulates brachyury, a gene with diverse roles in limb development, tumorigenesis and metastasis. Cell Cycle 9.

Chong, M. M., Zhang, G., Cheloufi, S., Neubert, T. A., Hannon, G. J., and Littman, D. R. (2010). Canonical and alternate functions of the microRNA biogenesis machinery. Genes Dev 24, 1951-1960.

Coarfa, C., Yu, F., Miller, C. A., Chen, Z., Harris, R. A., and Milosavljevic, A. (2010). Pash 3.0: A versatile software package for read mapping and integrative analysis of genomic and epigenomic variation using massively parallel DNA sequencing. BMC Bioinformatics 11, 572.

Creighton, C. J., Benham, A. L., Zhu, H., Khan, M. F., Reid, J. G., Nagaraja, A. K., Fountain, M. D., Dziadek, O., Han, D., Ma, L., et al. (2010). Discovery of novel microRNAs in female reproductive tract using next generation sequencing. PLoS One 5, e9637.

Creighton, C. J., Reid, J. G., and Gunaratne, P. H. (2009). Expression profiling of microRNAs by deep sequencing. Brief Bioinform 10, 490-497.

Farley, F. W., Soriano, P., Steffen, L. S., and Dymecki, S. M. (2000). Widespread recombinase expression using FLPeR (flipper) mice. Genesis 28, 106-110.

Flores, E. R. (2007). The roles of p63 in cancer. Cell Cycle 6, 300-304.

Flores, E. R., Tsai, K. Y., Crowley, D., Sengupta, S., Yang, A., McKeon, F., and Jacks, T. (2002). p63 and p73 are required for p53-dependent apoptosis in response to DNA damage. Nature 416, 560-564.

Griffiths-Jones, S. (2004). The microRNA Registry. Nucleic Acids Res 32, D109-111.

Griffiths-Jones, S., Grocock, R. J., van Dongen, S., Bateman, A., and Enright, A. J. (2006). miRBase: microRNA sequences, targets and gene nomenclature. Nucleic Acids Res 34, D140-144.

Griffiths-Jones, S., Saini, H. K., van Dongen, S., and Enright, A. J. (2008). miRBase: tools for microRNA genomics. Nucleic Acids Res 36, D154-158.

Grinnell, K. L., Yang, B., Eckert, R. L., and Bickenbach, J. R. (2007). De-differentiation of mouse interfollicular keratinocytes by the embryonic transcription factor Oct-4. J Invest Dermatol 127, 372-380.

Han, J., Pedersen, J. S., Kwon, S. C., Belair, C. D., Kim, Y. K., Yeom, K. H., Yang, W. Y., Haussler, D., Blelloch, R., and Kim, V. N. (2009). Posttranscriptional crossregulation between Drosha and DGCR8. Cell 136, 75-84.

Hong, H., Takahashi, K., Ichisaka, T., Aoi, T., Kanagawa, O., Nakagawa, M., Okita, K., and Yamanaka, S. (2009). Suppression of induced pluripotent stem cell generation by the p53-p21 pathway. Nature 460, 1132-1135.

Houbaviy, H. B., Murray, M. F., and Sharp, P. A. (2003). Embryonic stem cell-specific MicroRNAs. Dev Cell 5, 351-358.

Hu, L. Y., Sun, Z. G., Wen, Y. M., Cheng, G. Z., Wang, S. L., Zhao, H. B., and Zhang, X. R. (2010). ATP-mediated protein kinase B Akt/mammalian target of rapamycin mTOR/p70 ribosomal S6 protein p70S6 kinase signaling pathway activation promotes improvement of locomotor function after spinal cord injury in rats. Neuroscience 169, 1046-1062.

Ihrie, R. A., Marques, M. R., Nguyen, B. T., Horner, J. S., Papazoglu, C., Bronson, R. T., Mills, A. A., and Attardi, L. D. (2005). Perp is a p63-regulated gene essential for epithelial integrity. Cell 120, 843-856.

Judson, R. L., Babiarz, J. E., Venere, M., and Blelloch, R. (2009). Embryonic stem cell-specific microRNAs promote induced pluripotency. Nat Biotechnol 27, 459-461.

Kawamura, T., Suzuki, J., Wang, Y. V., Menendez, S., Morera, L. B., Raya, A., Wahl, G. M., and Izpisua Belmonte, J. C. (2009). Linking the p53 tumour suppressor pathway to somatic cell reprogramming. Nature 460, 1140-1144.

Koster, M. I., Dai, D., Marinari, B., Sano, Y., Costanzo, A., Karin, M., and Roop, D. R. (2007). p63 induces key target genes required for epidermal morphogenesis. Proc Natl Acad Sci USA 104, 3255-3260.

Koster, M. I., Kim, S., Mills, A. A., DeMayo, F. J., and Roop, D. R. (2004). p63 is the molecular switch for initiation of an epithelial stratification program. Genes Dev 18, 126-131.

Kozomara, A., and Griffiths-Jones, S. (2010). miRBase: integrating microRNA annotation and deep-sequencing data. Nucleic Acids Res 39, D152-157.

Landthaler, M., Yalcin, A., and Tuschl, T. (2004). The human DiGeorge syndrome critical region gene 8 and Its *D. melanogaster* homolog are required for miRNA biogenesis. Curr Biol 14, 2162-2167.

Lewandoski, M., Wassarman, K. M., and Martin, G. R. (1997). Zp3-cre, a transgenic mouse line for the activation or inactivation of loxP-flanked target genes specifically in the female germ line. Curr Biol 7, 148-151.

Li, H., Collado, M., Villasante, A., Strati, K., Ortega, S., Canamero, M., Blasco, M. A., and Serrano, M. (2009). The Ink4/Arf locus is a barrier for iPS cell reprogramming. Nature 460, 1136-1139.

Li, Z., Yang, C. S., Nakashima, K., and Rana, T. M. (2010). Small RNA-mediated regulation of iPS cell generation. EMBO J. 30, 823-834.

Lin, C. H., Jackson, A. L., Guo, J., Linsley, P. S., and Eisenman, R. N. (2009a). Myc-regulated microRNAs attenuate embryonic stem cell differentiation. EMBO J. 28, 3157-3170.

Lin, S. L., Chang, D. C., Chang-Lin, S., Lin, C. H., Wu, D. T., Chen, D. T., and Ying, S. Y. (2008). Mir-302 reprograms human skin cancer cells into a pluripotent ES-cell-like state. RNA 14, 2115-2124.

Lin, Y. L., Sengupta, S., Gurdziel, K., Bell, G. W., Jacks, T., and Flores, E. R. (2009b). p63 and p73 transcriptionally regulate genes involved in DNA repair. PLoS Genet. 5, e1000680.

Liu, P., Jenkins, N. A., and Copeland, N. G. (2003). A highly efficient recombineering-based method for generating conditional knockout mutations. Genome Res 13, 476-484.

Marion, R. M., Strati, K., Li, H., Murga, M., Blanco, R., Ortega, S., Fernandez-Capetillo, O., Serrano, M., and Blasco, M. A. (2009). A p53-mediated DNA damage response limits reprogramming to ensure iPS cell genomic integrity. Nature 460, 1149-1153.

Mills, A. A., Zheng, B., Wang, X. J., Vogel, H., Roop, D. R., and Bradley, A. (1999). p63 is a p53 homologue required for limb and epidermal morphogenesis. Nature 398, 708-713.

Pattyn, F., Speleman, F., De Paepe, A., and Vandesompele, J. (2003). RTPrimerDB: the real-time PCR primer and probe database. Nucleic Acids Res 31, 122-123.

Peter, M. E. (2009). An interview with Dr. Marcus E. Peter on his highly cited paper published in Cell Cycle. Cell Cycle 8, 2325.

Romano, R. A., Smalley, K., Magraw, C., Serna, V. A., Kurita, T., Raghavan, S., and Sinha, S. (2012). DeltaNp63 knockout mice reveal its indispensable role as a master regulator of epithelial development and differentiation. Development 139, 772-782.

Ross, P. J., Suhr, S. T., Rodriguez, R. M., Chang, E. A., Wang, K., Siripattarapravat, K., Ko, T., and Cibelli, J. B. (2010). Human-induced pluripotent stem cells produced under xeno-free conditions. Stem Cells Dev 19, 1221-1229.

Senoo, M., Pinto, F., Crum, C. P., and McKeon, F. (2007). p63 Is essential for the proliferative potential of stem cells in stratified epithelia. Cell 129, 523-536.

Su, X., Chakravarti, D., Cho, M. S., Liu, L., Gi, Y. J., Lin, Y. L., Leung, M. L., El-Naggar, A., Creighton, C. J., Suraokar, M. B., et al. (2010). TAp63 suppresses metastasis through coordinate regulation of Dicer and miRNAs. Nature 467, 986-990.

Su, X., Cho, M. S., Gi, Y. J., Ayanga, B. A., Sherr, C. J., and Flores, E. R. (2009a). Rescue of key features of the p63-null epithelial phenotype by inactivation of Ink4a and Arf. EMBO J. 28, 1904-1915.

Su, X., Paris, M., Gi, Y. J., Tsai, K. Y., Cho, M. S., Lin, Y. L., Biernaskie, J. A., Sinha, S., Prives, C., Pevny, L. H., et al. (2009b). TAp63 prevents premature aging by promoting adult stem cell maintenance. Cell Stem Cell 5, 64-75.

Takahashi, K., and Yamanaka, S. (2006). Induction of pluripotent stem cells from mouse embryonic and adult fibroblast cultures by defined factors. Cell 126, 663-676.

Taube, J. H., Allton, K., Duncan, S. A., Shen, L., and Barton, M. C. (2010). Foxa1 functions as a pioneer transcription factor at transposable elements to activate Afp during differentiation of embryonic stem cells. J Biol Chem 285, 16135-16144.

Tay, Y., Zhang, J., Thomson, A. M., Lim, B., and Rigoutsos, I. (2008). MicroRNAs to Nanog, Oct4 and Sox2 coding regions modulate embryonic stem cell differentiation. Nature 455, 1124-1128.

Teta, M., Choi, Y. S., Okegbe, T., Wong, G., Tam, O. H., Chong, M. M., Seykora, J. T., Nagy, A., Littman, D. R., Andl, T., et al. (2012). Inducible deletion of epidermal Dicer and Drosha reveals multiple functions for miRNAs in postnatal skin. Development 139, 1405-1416.

Utikal, J., Polo, J. M., Stadtfeld, M., Maherali, N., Kulalert, W., Walsh, R. M., Khalil, A., Rheinwald, J. G., and Hochedlinger, K. (2009). Immortalizati Wang, Y., Medvid, R., Melton, C., Jaenisch, R., and Blelloch, R. (2007). DGCR8 is essential for microRNA biogenesis and silencing of embryonic stem cell self-renewal. Nat Genet. 39, 380-385.

Xu, N., Papagiannakopoulos, T., Pan, G., Thomson, J. A., and Kosik, K. S. (2009). MicroRNA-145 regulates OCT4, SOX2, and KLF4 and represses pluripotency in human embryonic stem cells. Cell 137, 647-658.

Yang, A., Schweitzer, R., Sun, D., Kaghad, M., Walker, N., Bronson, R. T., Tabin, C., Sharpe, A., Caput, D., Crum, C., et al. (1999). p63 is essential for regenerative proliferation in limb, craniofacial and epithelial development. Nature 398, 714-718.

Yang, A., Zhu, Z., Kapranov, P., McKeon, F., Church, G. M., Gingeras, T. R., and Struhl, K. (2006). Relationships between p63 binding, DNA sequence, transcription activity, and biological function in human cells. Mol Cell 24, 593-602.

Yi, R., O'Carroll, D., Pasolli, H. A., Zhang, Z., Dietrich, F. S., Tarakhovsky, A., and Fuchs, E. (2006). Morphogenesis in skin is governed by discrete sets of differentially expressed microRNAs. Nat Genet. 38, 356-362.

Yi, R., Pasolli, H. A., Landthaler, M., Hafner, M., Ojo, T., Sheridan, R., Sander, C., O'Carroll, D., Stoffel, M., Tuschl, T., et al. (2009). DGCR8-dependent microRNA biogenesis is essential for skin development. Proc Natl Acad Sci USA 106, 498-502.

The invention claimed is:

1. A method of generating a human induced pluripotent stem (iPS) cell, comprising:
   (a) introducing an inhibitory nucleic acid that downregulates expression of ΔNp63 or DGCR8 into an isolated human somatic cell, wherein the inhibitory nucleic acid is a siRNA, miRNA, shRNA, an antisense molecule or a ribozyme;
   (b) culturing the cell obtained in step a) in an embryonic stem cell (ES) media; and
   (c) isolating an iPS cell from the culture in step b).

2. The method of claim 1, wherein the somatic cell is an epidermal cell, fibroblast, blood cell, mammary epithelial cell, lung epithelial cell, or intestinal epithelial cell.

3. The method of claim 2, wherein the epidermal cell is a keratinocyte.

4. The method of claim 1, wherein the inhibitory nucleic acid is shRNA, siRNA, or miRNA.

5. The method of claim 1, wherein the inhibitory nucleic acid is present in an expression vector.

6. The method of claim 5, wherein the expression vector is a lentiviral vector, a retroviral vector, an adenoviral vector, an episomal vector or a plasmid.

7. The method of claim 1, further comprising the step of assaying expression of one or more genes in the cultured cell, said genes selected from the group consisting of Oct4, Sox2, Klf4, and Nanog.

8. The method of claim 1, further comprising the step of subjecting the induced pluripotent stem cell to conditions to produce a differentiated cell.

9. The method of claim 8, wherein the differentiated cell is a neuron, blood cell, muscle cell, skin cell, or bone cell.

10. The method of claim 1, wherein the inhibitory nucleic acid downregulates expression of ΔNp63 in the somatic cell.

11. The method of claim 1, wherein the inhibitory nucleic acid downregulates expression of DGCR8 in the somatic cell.

\* \* \* \* \*